US008945832B2

(12) United States Patent
Uhlen et al.

(10) Patent No.: US 8,945,832 B2
(45) Date of Patent: Feb. 3, 2015

(54) TREATMENT PREDICTION INVOLVING HMGCR

(75) Inventors: Mathias Uhlen, Stucksund (SE); Fredrik Ponten, Uppsala (SE); Karin Jirström, Limhamn (SE); Donal J. Brennan, Dublin (IE)

(73) Assignee: Atlas Antibodies AB, Stockholm (SE)

( * ) Notice: Subject to any disclaimer, the term of this patent is extended or adjusted under 35 U.S.C. 154(b) by 883 days.

(21) Appl. No.: 12/946,934

(22) Filed: Nov. 16, 2010

(65) Prior Publication Data

US 2011/0142828 A1     Jun. 16, 2011

Related U.S. Application Data

(63) Continuation-in-part of application No. PCT/SE2009/000066, filed on Jan. 30, 2009, and a continuation of application No. PCT/EP2008/056071, filed on May 16, 2008.

(51) Int. Cl.
| | | |
|---|---|---|
| C12Q 1/68 | (2006.01) | |
| G01N 33/53 | (2006.01) | |
| G01N 33/574 | (2006.01) | |
| C12Q 1/26 | (2006.01) | |
| G01N 33/573 | (2006.01) | |

(52) U.S. Cl.
CPC ............ *G01N 33/57415* (2013.01); *C12Q 1/26* (2013.01); *G01N 33/573* (2013.01); *G01N 2333/90209* (2013.01)
USPC ............................................ 435/6.1; 435/7.1

(58) Field of Classification Search
None
See application file for complete search history.

(56) References Cited

U.S. PATENT DOCUMENTS 7,504,214 B2    3/2009    Erlander et al.

FOREIGN PATENT DOCUMENTS

| CN | 1969047 A | 5/2007 |
|---|---|---|
| WO | WO 03/018833 A2 | 3/2003 |
| WO | WO 2004/097030 A2 | 11/2004 |
| WO | WO 2005/083429 A2 | 9/2005 |
| WO | WO 2007/094027 A2 | 8/2007 |
| WO | WO 2007/121459 A2 | 10/2007 |
| WO | WO 2008/019375 A2 | 2/2008 |

OTHER PUBLICATIONS

O'Driscoll et al (Cancer Genomics & Proteomics, 2008, 5: 95-104).*
Rody et al (Zentralbl Gynakol, 2006, 128(2): Abstract).*
Turashvili et al (BMC Cancer, 2007, 7(55): 1-20).*
Dressman et al (Clin Cancer Res, 2006, 12: 819-826).*
Celis et al (FEBS Letters, 2006, 2935-2944).*
Addeo et al., "Stimulation of Human Breast Cancer MCF-7 Cells with Estrogen Prevents Cell Cycle Arrest by HMG-CoA Reductase Inhibitors", Biochemical and Biophysical Research Communications, vol. 220, No. 3, pp. 864-870, Mar. 27, 1996, XP005176798.
Beenken et al., "Molecular Biomarkers for Breast Cancer Prognosis: Coexpression of c-erbB-2 and p53", Annals of Surgery, vol. 233, No. 5, pp. 630-638, XP002500033.
Borgquist et al., "HMG-CoA Reductase Expression in Breast Cancer is associated with a less Aggressive Phenotype and Influenced by Anthropometric Factors", International Journal of Cancer, vol. 123, No. 5, pp. 1146-1153, Sep. 1, 2008, XP002530265.
Borgquist et al., "Prognostic Impact of Tumour-Specific HMG-CoA Reductase Expression in Primary Breast Cancer", Breast Cancer Research, vol. 10, No. 5, pp. 1-11, Sep. 22, 2008, XP021046858.
Celis et al., "Apocrine Cysts of the Breast, Biomarkers, Origin, Enlargement, and Relation with Cancer Phenotype", Molecular & Cellular Proteomics, vol. 5, No. 3, pp. 462-483, Mar. 2006, XP002530215.
Celis et al., "Molecular pathology of breast apocrine carcinomas: A protein expression signature specific for benign apocrine metaplasia", FEBS Letters, vol. 580, No. 12, pp. 2935-2944, May 22, 2006, XP005445772.
Cypriani et al., "Effect of Estradiol and Antiestrogens on Cholesterol Biosynthesis in Hormone-Dependent and -independent Breast Cancer Cell Lines", Biochemical et Biophysica ACTA, vol. 972, No. 2, pp. 167-178, Nov. 18, 1988, XP023578601.
Denoyelle et al., "Cerivastatin, An Inhibitor of HMG-CoA Reductase, Inhibits the Signaling Pathways Involved in the Invasiveness and Metastatic Properties of Highly Invasive Breast Cancer Cell Lines: An in vitro Study", Carcinogenesis, vol. 22, No. 8, pp. 1139-1148, 2001.
Di Croce et al., "Independent Behavior of Rat Liver LDL Receptor and HMGCoA Reductase Under Estrogen Treatment", Biochemical and Biophysical Research Communications, vol. 224, pp. 345-350, Article No. 1031, 1996.
Di Croce et al., "The Promoter of the Rat 3-Hydroxy-3-Methylglutaryl Coenzyme A Reductase Gene Contains a Tissue-Specific Estrogen-Responsive Region", Molecular Endocrinology, vol. 13, pp. 1225-1236, 1999.
Duncan et al., "Dietary Factors and the Regulation of 3-Hydroxy-3-Methylglutaryl Coenzyme A Reductase: Implications for Breast Cancer Development", Mol. Nutr. Food Res., vol. 49, No. 2, pp. 93-100, Feb. 2005, XP002530216.

(Continued)

*Primary Examiner* — Sean Aeder
(74) *Attorney, Agent, or Firm* — Birch, Stewart, Kolasch & Birch, LLP

(57) ABSTRACT

The present invention provides a method for determining whether a mammalian subject having a breast cancer is likely to benefit from an endocrine treatment, comprising the steps of: providing a sample earlier obtained from said subject; evaluating the amount of HMGCR protein or HMGCR mRNA present in at least part of said sample, and determining a sample value corresponding to said amount; comparing the sample value obtained in step b) with a reference value; and, if said sample value is higher than said reference value, concluding that the subject is likely to benefit from an endocrine treatment. Further, a corresponding method of treatment is provided as well as further methods uses and means which may be employed in connection with breast cancer treatment or treatment prediction.

16 Claims, 13 Drawing Sheets

(56) References Cited

OTHER PUBLICATIONS

Fabian, "The What, Why and How of Aromatase Inhibitors: Hormonal Agents for Treatment and Prevention of Breast Cancer", International Journal of Clinical Practice, vol. 61, No. 12, pp. 2051-2063, Dec. 2007, XP002530212.

Farmer et al, "Identification of Molecular Apocrine Breast Tumours by Microarray Analysis", Oncogene, vol. 24, No. 29, pp. 4660-4671, Jul. 7, 2005, XP002530214.

Glinsky et al., "Classification of Human Breast Cancer Using Gene Expression Profiling as a Component of the Survival Predictor Algorithm", Clinical Cancer Research, vol. 10, No. 7, pp. 2272-2283, XP002309961.

Harrewijn et al., "Feedback Mechanisms, Natural Terpenoids as Messengers: A Multidisciplinary Study of Their Production, Biological Functions, and Practical Applications", Kluwer Academic Pub, Boston, MA, pp. 74-84, Jan. 1, 2001, XP008106721.

International Breast Cancer Study Group (IBCSG), "Endocrine Responsiveness and Tailoring Adjuvant Therapy for Postmenopausal Lymph Node-Negative Breast Cancer: A Randomized Trial", Journal of the National Cancer Institute, vol. 94, No. 14, pp. 1054-1065, Jul. 17, 2002, XP002501703.

International Search Report and Notification of Transmittal of the International Search Report and Written Opinion of the International Searching Authority, or the Declaration dated Aug. 13, 2009 for Application No. PCT/SE2009/000066 (Forms PCT/ISA/210 and PCT/ISA/220).

International Search Report and Notification of Transmittal of the International Search Report and Written Opinion of the International Searching Authority, or the Declaration dated Dec. 10, 2008 for Application No. PCT/EP2008/056071 (Forms PCT/ISA/210 and PCT/ISA/220).

Jordan et al., "Introducing a New Section to Breast Cancer Research: Endocrinology and Hormone Therapy", Breast Cancer Research, vol. 5, No. 6, pp. 281-283, 2003, XP002530218.

Marseille-Tremblay et al., "Impact of Maternal Circulating Cholesterol and Gestational Diabetes Mellitus on Lipid Metabolism in Human Term Placenta", Molecular Reproduction and Development, vol. 75, No. 6, pp. 1054-1062, Jun. 2008, XP002500031.

Maynard et al., "Antibody Engineering", Annual Review of Biomedical Engineering, vol. 2., pp. 339-376, Jan. 2000, XP009039750.

Notarnicola et al., "Effect of Genistein on Cholesterol Metabolism-Related Genes in a Colon Cancer Cell Line", Genes & Nutrition, vol. 3, No. 1, pp. 35-40, Apr. 2008, XP002530217.

Shachaf et at, "Inhibition of HMGco Reductase by Atorvastatin Prevents and Reverses MYC-Induced Lymphomagenesis", The American Society of Hematology, Blood, vol. 110, No. 7, pp. 2674-2684, Oct. 1, 2007.

Toth-Fejel et al., "Estrogen and Androgen Receptors as Comediators of Breast Cancer Cell Proliferation, Providing a New Therapeutic Tool", Archives of Surgery, vol. 139, No. 1, pp. 50-54, Jan. 2004, XP002530213.

Van Den Bossche et al., "Early Prediction of Endocrine Therapy Effect in Advanced Breast Cancer Patients Using 99mTc-Depreotide Scintigraphy", Journal of Nuclear Medicine, vol. 47, No. 1., pp. 6-13, Jan. 1, 2006, XP002530211.

Van Golen et al., "A Novel Putative Low-Affinity Insulin-like Growth Factory-binding Protein, LIBC (Lost in Inflammatory Breast Cancer), and RhoC GTPase Correlate with the Inflammatory Breast Cancer Phenotype", Clinical Cancer Research, vol. 5, No. 9, pp. 2511-2519, Sep. 1999, XP002500030.

Viale et al. "Prognostic and Predictive Value of Centrally Reviewed Expression of Estrogen and Progesterone Receptors in a Randomized Trial Comparing Letrozole and Tamoxifen Adjuvant Therapy etc.", Journal of Clinical Oncology, vol. 25, No. 25, pp. 3846-3852, Sep. 1, 2007, XP002501702.

Vogel, "Can Statin Therapy Reduce the Risk of Breast Cancer?", Journal of Clincal Oncology, vol. 23, No. 34, pp. 8553-8555, Dec. 1, 2005, XP002501701.

Yu et al. "A Transcriptional Fingerprint of Estrogen in Human Breast Cancer Predicts Patient Survival", Neoplasia, vol. 10, No. 1, pp. 79-88, Jan. 2008, XP002500032.

Dowsett et al., "Benefit from adjuvant tamoxifen therapy in primary breast cancer patients according oestrogen receptor, progesterone receptor, EGF receptor and HER2 status", Annals of Oncology: Official Journal of the ESMO, vol. 17, No. 5, May 2006, p. 818-826.

European Office Action for European Patent Application No. 09746841.7 dated Feb. 1, 2012.

English translation (only) of Japanese Office Action, dated Sep. 10, 2013, for Patent Application No. 2011-509434.

Office Action for Chinese Application No. 200980126851.8, dated Sep. 11, 2012, including an English translation.

English translation of Third Office Action, dated Oct. 22, 2013, for Chinese Application No. 200980126851.8.

Wang et al., "Present Status of Endocrine Therapy for Breast Cancer", Chinese Journal of Current Advances in General Surgery, vol. 7, No. 5, Oct. 2004, pp. 260-262.

\* cited by examiner

```
                          SEQUENCE LISTING

<160> NUMBER OF SEQ ID NOS: 4

<210> SEQ ID NO 1
<211> LENGTH: 140
<212> TYPE: PRT
<213> ORGANISM: Homo sapiens

<400> SEQUENCE: 1

Met Ala Gly Ser Ile Gly Gly Tyr Asn Ala His Ala Ala Asn Ile Val
1               5                   10                  15

Thr Ala Ile Tyr Ile Ala Cys Gly Gln Asp Ala Ala Gln Asn Val Gly
            20                  25                  30

Ser Ser Asn Cys Ile Thr Leu Met Glu Ala Ser Gly Pro Thr Asn Glu
        35                  40                  45

Asp Leu Tyr Ile Ser Cys Thr Met Pro Ser Ile Glu Ile Gly Thr Val
    50                  55                  60

Gly Gly Gly Thr Asn Leu Leu Pro Gln Gln Ala Cys Leu Gln Met Leu
65                  70                  75                  80

Gly Val Gln Gly Ala Cys Lys Asp Asn Pro Gly Glu Asn Ala Arg Gln
                85                  90                  95

Leu Ala Arg Ile Val Cys Gly Thr Val Met Ala Gly Glu Leu Ser Leu
            100                 105                 110

Met Ala Ala Leu Ala Ala Gly His Leu Val Lys Ser His Met Ile His
        115                 120                 125

Asn Arg Ser Lys Ile Asn Leu Gln Asp Leu Gln Gly
    130                 135                 140

<210> SEQ ID NO 2
<211> LENGTH: 888
<212> TYPE: PRT
<213> ORGANISM: Homo sapiens

<400> SEQUENCE: 2

Met Leu Ser Arg Leu Phe Arg Met His Gly Leu Phe Val Ala Ser His
1               5                   10                  15

Pro Trp Glu Val Ile Val Gly Thr Val Thr Leu Thr Ile Cys Met Met
            20                  25                  30

Ser Met Asn Met Phe Thr Gly Asn Asn Lys Ile Cys Gly Trp Asn Tyr
        35                  40                  45

Glu Cys Pro Lys Phe Glu Glu Asp Val Leu Ser Ser Asp Ile Ile Ile
    50                  55                  60
```

```
Leu Thr Ile Thr Arg Cys Ile Ala Ile Leu Tyr Ile Tyr Phe Gln Phe
 65                  70                  75                  80

Gln Asn Leu Arg Gln Leu Gly Ser Lys Tyr Ile Leu Gly Ile Ala Gly
                 85                  90                  95

Leu Phe Thr Ile Phe Ser Ser Phe Val Phe Ser Thr Val Val Ile His
            100                 105                 110

Phe Leu Asp Lys Glu Leu Thr Gly Leu Asn Glu Ala Leu Pro Phe Phe
        115                 120                 125

Leu Leu Leu Ile Asp Leu Ser Arg Ala Ser Thr Leu Ala Lys Phe Ala
    130                 135                 140

Leu Ser Ser Asn Ser Gln Asp Glu Val Arg Glu Asn Ile Ala Arg Gly
145                 150                 155                 160

Met Ala Ile Leu Gly Pro Thr Phe Thr Leu Asp Ala Leu Val Glu Cys
                165                 170                 175

Leu Val Ile Gly Val Gly Thr Met Ser Gly Val Arg Gln Leu Glu Ile
            180                 185                 190

Met Cys Cys Phe Gly Cys Met Ser Val Leu Ala Asn Tyr Phe Val Phe
        195                 200                 205

Met Thr Phe Phe Pro Ala Cys Val Ser Leu Val Leu Glu Leu Ser Arg
    210                 215                 220

Glu Ser Arg Glu Gly Arg Pro Ile Trp Gln Leu Ser His Phe Ala Arg
225                 230                 235                 240

Val Leu Glu Glu Glu Glu Asn Lys Pro Asn Pro Val Thr Gln Arg Val
                245                 250                 255

Lys Met Ile Met Ser Leu Gly Leu Val Leu Val His Ala His Ser Arg
            260                 265                 270

Trp Ile Ala Asp Pro Ser Pro Gln Asn Ser Thr Ala Asp Thr Ser Lys
        275                 280                 285

Val Ser Leu Gly Leu Asp Glu Asn Val Ser Lys Arg Ile Glu Pro Ser
    290                 295                 300

Val Ser Leu Trp Gln Phe Tyr Leu Ser Lys Met Ile Ser Met Asp Ile
305                 310                 315                 320

Glu Gln Val Ile Thr Leu Ser Leu Ala Leu Leu Ala Val Lys Tyr
                325                 330                 335

Ile Phe Phe Glu Gln Thr Glu Thr Glu Ser Thr Leu Ser Leu Lys Asn
            340                 345                 350

Pro Ile Thr Ser Pro Val Val Thr Gln Lys Lys Val Pro Asp Asn Cys
        355                 360                 365

Cys Arg Arg Glu Pro Met Leu Val Arg Asn Asn Gln Lys Cys Asp Ser
    370                 375                 380

Val Glu Glu Glu Thr Gly Ile Asn Arg Glu Arg Lys Val Glu Val Ile
385                 390                 395                 400

Lys Pro Leu Val Ala Glu Thr Asp Thr Pro Asn Arg Ala Thr Phe Val
                405                 410                 415

Val Gly Asn Ser Ser Leu Leu Asp Thr Ser Ser Val Leu Val Thr Gln
            420                 425                 430

Glu Pro Glu Ile Glu Leu Pro Arg Glu Pro Arg Pro Asn Glu Glu Cys
        435                 440                 445

Leu Gln Ile Leu Gly Asn Ala Glu Lys Gly Ala Lys Phe Leu Ser Asp
    450                 455                 460

Ala Glu Ile Ile Gln Leu Val Asn Ala Lys His Ile Pro Ala Tyr Lys
465                 470                 475                 480
```

```
Leu Glu Thr Leu Met Glu Thr His Glu Arg Gly Val Ser Ile Arg Arg
                485                 490                 495
Gln Leu Leu Ser Lys Lys Leu Ser Glu Pro Ser Ser Leu Gln Tyr Leu
            500                 505                 510
Pro Tyr Arg Asp Tyr Asn Tyr Ser Leu Val Met Gly Ala Cys Cys Glu
            515                 520                 525
Asn Val Ile Gly Tyr Met Pro Ile Pro Val Gly Val Ala Gly Pro Leu
            530                 535                 540
Cys Leu Asp Glu Lys Glu Phe Gln Val Pro Met Ala Thr Thr Glu Gly
545                 550                 555                 560
Cys Leu Val Ala Ser Thr Asn Arg Gly Cys Arg Ala Ile Gly Leu Gly
                565                 570                 575
Gly Gly Ala Ser Ser Arg Val Leu Ala Asp Gly Met Thr Arg Gly Pro
            580                 585                 590
Val Val Arg Leu Pro Arg Ala Cys Asp Ser Ala Glu Val Lys Ala Trp
            595                 600                 605
Leu Glu Thr Ser Glu Gly Phe Ala Val Ile Lys Glu Ala Phe Asp Ser
            610                 615                 620
Thr Ser Arg Phe Ala Arg Leu Gln Lys Leu His Thr Ser Ile Ala Gly
625                 630                 635                 640
Arg Asn Leu Tyr Ile Arg Phe Gln Ser Arg Ser Gly Asp Ala Met Gly
                645                 650                 655
Met Asn Met Ile Ser Lys Gly Thr Glu Lys Ala Leu Ser Lys Leu His
                660                 665                 670
Glu Tyr Phe Pro Glu Met Gln Ile Leu Ala Val Ser Gly Asn Tyr Cys
            675                 680                 685
Thr Asp Lys Lys Pro Ala Ala Ile Asn Trp Ile Glu Gly Arg Gly Lys
690                 695                 700
Ser Val Val Cys Glu Ala Val Ile Pro Ala Lys Val Val Arg Glu Val
705                 710                 715                 720
Leu Lys Thr Thr Thr Glu Ala Met Ile Glu Val Asn Ile Asn Lys Asn
                725                 730                 735
Leu Val Gly Ser Ala Met Ala Gly Ser Ile Gly Gly Tyr Asn Ala His
                740                 745                 750
Ala Ala Asn Ile Val Thr Ala Ile Tyr Ile Ala Cys Gly Gln Asp Ala
            755                 760                 765
Ala Gln Asn Val Gly Ser Ser Asn Cys Ile Thr Leu Met Glu Ala Ser
            770                 775                 780
Gly Pro Thr Asn Glu Asp Leu Tyr Ile Ser Cys Thr Met Pro Ser Ile
785                 790                 795                 800
Glu Ile Gly Thr Val Gly Gly Gly Thr Asn Leu Leu Pro Gln Gln Ala
                805                 810                 815
Cys Leu Gln Met Leu Gly Val Gln Gly Ala Cys Lys Asp Asn Pro Gly
                820                 825                 830
Glu Asn Ala Arg Gln Leu Ala Arg Ile Val Cys Gly Thr Val Met Ala
            835                 840                 845
Gly Glu Leu Ser Leu Met Ala Ala Leu Ala Ala Gly His Leu Val Lys
850                 855                 860
Ser His Met Ile His Asn Arg Ser Lys Ile Asn Leu Gln Asp Leu Gln
865                 870                 875                 880
Gly Ala Cys Thr Lys Lys Thr Ala
                885
```

<210> SEQ ID NO 3
<211> LENGTH: 4475
<212> TYPE: DNA
<213> ORGANISM: Homo sapiens

<400> SEQUENCE: 3

```
ttcggtggcc tctagtgaga tctggaggat ccaaggattc tgtagctaca atgttgtcaa      60 gacttttcg  aatgcatggc ctctttgtgg cctcccatcc ctgggaagtc atagtgggga     120
cagtgacact gaccatctgc atgatgtcca tgaacatgtt tactggtaac aataagatct     180
gtggttggaa ttatgaatgt ccaaagtttg aagaggatgt tttgagcagt gacattataa     240
ttctgacaat aacacgatgc atagccatcc tgtatattta cttccagttc cagaatttac     300
gtcaacttgg atcaaaatat attttgggta ttgctggcct tttcacaatt ttctcaagtt     360
ttgtattcag tacagttgtc attcacttct tagacaaaga attgacaggc ttgaatgaag     420
ctttgccctt tttcctactt ttgattgacc tttccagagc aagcacatta gcaaagtttg     480
ccctcagttc caactcacag gatgaagtaa gggaaaatat tgctcgtgga atggcaattt     540
taggtcctac gtttaccctc gatgctcttg ttgaatgtct tgtgattgga gttggtacca     600
tgtcaggggt acgtcagctt gaaattatgt gctgctttgg ctgcatgtca gttcttgcca     660
actacttcgt gttcatgact ttcttcccag cttgtgtgtc cttggtatta gagctttctc     720
gggaaagccg cgagggtcgt ccaatttggc agctcagcca ttttgcccga gttttagaag     780
aagaagaaaa taagccgaat cctgtaactc agagggtcaa gatgattatg tctctaggct     840
tggttcttgt tcatgctcac agtcgctgga tagctgatcc ttctcctcaa aacagtacag     900
cagatacttc taaggtttca ttaggactgg atgaaaatgt gtccaagaga attgaaccaa     960
gtgtttccct ctggcagttt tatctctcta aaatgatcag catggatatt gaacaagtta    1020
ttaccctaag tttagctctc cttctggctg tcaagtacat cttctttgaa caaacagaga    1080
cagaatctac actctcatta aaaaacccta tcacatctcc tgtagtgaca caaagaaag     1140 tcccagacaa ttgttgtaga cgtgaaccta tgctggtcag aaataaccag aaatgtgatt    1200
cagtagagga agagacaggg ataaaccgag aaagaaaagt tgaggttata aaacccttag    1260
tggctgaaac agataccca  aacagagcta catttgtggt tggtaactcc tccttactcg    1320
atacttcatc agtactggtg acacaggaac ctgaaattga acttcccagg gaacctcggc    1380
ctaatgaaga atgtctacag atacttggga atgcagagaa aggtgcaaaa ttccttagtg    1440
atgctgagat catccagtta gtcaatgcta agcatatccc agcctacaag ttggaaactc    1500
tgatggaaac tcatgagcgt ggtgtatcta ttcgccgaca gttactttcc aagaagcttt    1560
cagaaccttc ttctctccag tacctacctt acagggatta taattactcc ttggtgatgg    1620
gagcttgttg tgagaatgtt attggatata tgcccatccc tgttggagtg gcaggacccc    1680
tttgcttaga tgaaaaagaa tttcaggttc caatggcaac aacagaaggt tgtcttgtgg    1740
ccagcaccaa tagaggctgc agagcaatag gtcttgtgg  aggtgccagc agccgagtcc    1800
ttgcagatgg gatgactcgt ggcccagttg tgcgtcttcc acgtgcttgt gactctgcag    1860
aagtgaaagc ctggctcgaa acatctgaag ggttcgcagt gataaaggag gcatttgaca    1920
gcactagcag atttgcacgt ctacagaaac ttcatacaag tatagctgga cgcaaccttt    1980
atatccgttt ccagtccagg tcaggggatg ccatgggat  gaacatgatt tcaaagggta    2040
cagagaaagc actttcaaaa cttcacgagt atttccctga aatgcagatt ctagccgtta    2100
gtggtaacta ttgtactgac aagaaacctg ctgctataaa ttggatagag ggaagaggaa    2160
```

```
aatctgttgt ttgtgaagct gtcattccag ccaaggttgt cagagaagta ttaaagacta      2220
ccacagaggc tatgattgag gtcaacatta acaagaattt agtgggctct gccatggctg      2280
ggagcatagg aggctacaac gcccatgcag caaacattgt caccgccatc tacattgcct      2340
gtggacagga tgcagcacag aatgttggta gttcaaactg tattacttta atggaagcaa      2400
gtggtcccac aaatgaagat ttatatatca gctgcaccat gccatctata gagataggaa      2460
cggtgggtgg tgggaccaac ctactacctc agcaagcctg tttgcagatg ctaggtgttc      2520
aaggagcatg caaagataat cctggggaaa atgcccggca gcttgcccga attgtgtgtg      2580
ggaccgtaat ggctggggaa ttgtcactta tggcagcatt ggcagcagga catcttgtca      2640
aaagtcacat gattcacaac aggtcgaaga tcaatttaca agacctccaa ggagcttgca      2700
ccaagaagac agcctgaata gcccgacagt tctgaactgg aacatgggca ttgggttcta      2760
aaggactaac ataaaatctg tgaattaaaa aagctcaatg cattgtcttg tggaggatga      2820
atagatgtga tcactgagac agccacttgg ttttggctc tttcagagag gtctcaggtt      2880 cttttccatgc agactcctca gatctgaaca cagtttagtg ctttacatgc tgtgctcttt      2940
gaagagattt caacaagaat attgtatgtt aaagcatcag agatggtaat ctacagctca      3000
cctctgaagg caaatataag ctgggaaaaa agttttgatg aaattcttga agttcatggt      3060
gatcagtgca attgaccttc tccctcactc ctgccagttg aaaatggatt tttaaattat      3120
actgtagctg atgaaactcc tgattttgta gttaatttat taagtctggg atgtagaact      3180
tcaagaagta agagctaagt tctaagttca tgtttgtaaa ttaatacttc atttggtgct      3240
ggtctatttt gattttgggg ggtaatcagc attattcttc agaaggggac ctgttttctt      3300
caagggaaga aacactctta ttcccaaact acagaataat gtgttaaaca tgctaaatag      3360
ttctatcagg aaaacaaatc actgtattta tctccgcagg ctatttgttc agagaggcct      3420
tttgtttaaa tataaatgtt taaatataaa tgtttgtctg gattggctat aacatgtctt      3480
tcagcattag gcttttaaga aacacagggt tttgtattct ttactaaaga tatcagagct      3540
cttaatgttg cttagatgag ggtgactgtc aagtacaagc aagactggga ccttagaaat      3600
cattgtagaa acacagtttt gaaagaaaaa taccatgtct ctaagccaac tttaattgct      3660
taaaagacat ttttatttag ttgaaaaatc tagttttttt tgtaaactgt atcaaatctg      3720
tatatgttgt aataaaactt atgctagttt attggaagtg ttcaagaaat aaaaatcaac      3780
ttgtgtactg ataaaatact ctagcctggg ccagagaaga taatgttctt taatgttgtc      3840
caggaaaccc tggcttgctt gccgagccta atgaaaggga aagtcagctt tcagagccag      3900
tgaaggagcc acgtgaatgg ccctagaact gtgcctagtt cctgtggcca ggaggttggt      3960
gactgaaaca ttcacacagg gctctttgat ggacccacga acgctcttag ctttctcagg      4020
gggtcagcag agttattgaa tcttaatttt ttttaatgta caagttttgt ataaataata      4080
aagaactcct tattttgtat tacatctaat gcttcaagtg ttgctcttgg aaagctgatg      4140
atgtctcttg tagaagatgg actctgaaaa acattccagg aaaccatggc agcatggaga      4200
gcctcttagt gattgtgtct gcattgttat tgtggaagat ttacctttc tgttgtacgt      4260 aaagcttaaa ttgcttttgt tgtgactttt tagccagtga ctttttctga gcttttcatg      4320
gaagtggcag tgaaaaatat gttgagtgtt cattttagtg actgtaatta atatcttgct      4380
ggattaatgt tttgtacaat tactaaattg tatacatttt gttatagaat actttttttct      4440 agtttcagta aataatgaaa aggaagttaa tacca                                 4475
```

```
<210> SEQ ID NO 4
<211> LENGTH: 14
<212> TYPE: PRT
<213> ORGANISM: Homo sapiens

<400> SEQUENCE: 4

Cys Lys Asp Asn Pro Gly Glu Asn Ala Arg Gln Leu Ala Arg
1               5                   10
```

TREATMENT PREDICTION INVOLVING HMGCR

This application is a Continuation-In-Part of PCT/SE2009/000066, filed Jan. 30, 2009 for which priority is claimed under 35 U.S.C. §120. This application is also a Continuation of PCT/EP2008/056071, filed on May 16, 2008 for which priority is claimed under 35 U.S.C. §120. The entire contents of each of the above applications is herein incorporated by reference.

TECHNICAL FIELD

The present disclosure relates to the field of breast cancer treatment and treatment prediction. It also relates to means which may be employed in such a treatment or treatment prediction.

BACKGROUND

Cancer

Cancer is one of the most common causes of disease and death in the western world. In general, incidence rates increase with age for most forms of cancer. As human populations continue to live longer, due to an increase of the general health status, cancer may affect an increasing number of individuals. The cause of most common cancer types is still largely unknown, although there is an increasing body of knowledge providing a link between environmental factors (dietary, tobacco smoke, UV radiation etc) as well as genetic factors (germ line mutations in "cancer genes" such as p53, APC, BRCA1, XP etc) and the risk for development of cancer.

No definition of cancer is entirely satisfactory from a cell biological point of view, despite the fact that cancer is essentially a cellular disease and defined as a transformed cell population with net cell growth and anti-social behavior. Malignant transformation represents the transition to a malignant phenotype based on irreversible genetic alterations. Although this has not been formally proven, malignant transformation is believed to take place in one cell, from which a subsequently developed tumor originates (the "clonality of cancer" dogma). Carcinogenesis is the process by which cancer is generated and is generally accepted to include multiple events that ultimately lead to growth of a malignant tumor. This multi-step process includes several rate-limiting steps, such as addition of mutations and possibly also epigenetic events, leading to formation of cancer following stages of precancerous proliferation. The stepwise changes involve accumulation of errors (mutations) in vital regulatory pathways that determine cell division, asocial behavior and cell death. Each of these changes may provide a selective Darwinian growth advantage compared to surrounding cells, resulting in a net growth of the tumor cell population. A malignant tumor does not only necessarily consist of the transformed tumor cells themselves but also surrounding normal cells which act as a supportive stroma. This recruited cancer stroma consists of connective tissue, blood vessels and various other normal cells, e.g., inflammatory cells, which act in concert to supply the transformed tumor cells with signals necessary for continued tumor growth.

The most common forms of cancer arise in somatic cells and are predominantly of epithelial origin, e.g., prostate, breast, colon, urothelial and skin, followed by cancers originating from the hematopoetic lineage, e.g., leukemia and lymphoma, neuroectoderm, e.g., malignant gliomas, and soft tissue tumors, e.g., sarcomas.

Cancer Diagnostics and Prognostics

Microscopic evaluation of a tissue section taken from a tumor remains the golden standard for determining a diagnosis of cancer. For example, for microscopic diagnosis, biopsy material from suspected tumors is collected and examined under the microscope. To obtain a firm diagnosis, the tumor tissue is fixated in formalin, histo-processed and paraffin embedded. From the resulting paraffin block, tissue sections can be produced and stained using both histochemical, i.e., hematoxylin-eosin staining, and immunohistochemical methods. The surgical specimen is then evaluated with pathology techniques, including gross and microscopic analysis. This analysis often forms the basis for assigning a specific diagnosis, i.e., classifying the tumor type and grading the degree of malignancy, of a tumor.

Malignant tumors can be categorized into several stages according to classification schemes specific for each cancer type. The most common classification system for solid tumors is the tumor-node-metastasis (TNM) staging system. The T stage describes the local extent of the primary tumor, i.e., how far the tumor has invaded and imposed growth into surrounding tissues, whereas the N stage and M stage describe how the tumor has developed metastases, with the N stage describing spread of tumor to lymph nodes and the M stage describing growth of tumor in other distant organs. Early stages include: T0-1, N0, M0, representing localized tumors with negative lymph nodes. More advanced stages include: T2-4, N0, M0, localized tumors with more widespread growth and T1-4, N1-3, M0, tumors that have metastasized to lymph nodes and T1-4, N1-3, M1, tumors with a metastasis detected in a distant organ. Staging of tumors is often based on several forms of examination, including surgical, radiological and histopathological analyses. In addition to staging, there is also a classification system to grade the level of malignancy for most tumor types. The grading systems rely on morphological assessment of a tumor tissue sample and are based on the microscopic features found in a given tumor. These grading systems may be based on the degree of differentiation, proliferation and atypical appearance of the tumor cells. Examples of generally employed grading systems include Gleason grading for prostatic carcinomas and the Nottingham Histological Grade (NHG) grading for breast carcinomas.

Accurate staging and grading is crucial for a correct diagnosis and may provide an instrument to predict a prognosis. The diagnostic and prognostic information for a specific tumor subsequently determines an adequate therapeutic strategy for a given cancer patient. A commonly used method, in addition to histochemical staining of tissue sections, to obtain more information regarding a tumor is immunohistochemical staining. IHC allows for the detection of protein expression patterns in tissues and cells using specific antibodies. The use of IHC in clinical diagnostics allows for the detection of immunoreactivity in different cell populations, in addition to the information regarding tissue architecture and cellular morphology that is assessed from the histochemically stained tumor tissue section. IHC can be involved in supporting the accurate diagnosis, including staging and grading, of a primary tumor as well as in the diagnostics of metastases of unknown origin. The most commonly used antibodies in clinical practice today include antibodies against cell type "specific" proteins, e.g., PSA (prostate), MelanA (melanocytes) and Thyroglobulin (thyroid gland), and antibodies recognizing intermediate filaments (epithelial, mesenchymal, glial), cluster of differentiation (CD) antigens (hematopoetic, sub-classification of lympoid cells) and markers of malignant potential, e.g., Ki67 (proliferation), p53 (commonly mutated tumor suppressor gene) and HER-2 (growth factor receptor).

Aside from IHC, the use of in situ hybridization for detecting gene amplification and gene sequencing for mutation analysis are evolving technologies within cancer diagnostics. In addition, global analysis of transcripts, proteins or metabolites all add relevant information. However, most of these analyses still represent basic research and have yet to be evaluated and standardized for the use in clinical medicine.

Breast Cancer

Breast cancer is the second most common form of cancer worldwide and by far the most frequent cancer of women. Data from the GLOBOCAM 2002 database presented by Parkin et al. reveal 1.15 million new cases in 2002 and 0.41 million deaths during the same period (Parkin D M et al. (2005) CA Cancer J Clin 55, 74-108). If detected at an early stage, the prognosis is relatively good for a patient living in a developed country, with a general five-year survival rate of 73%, compared to 57% in a developing country. The incidence is slowly increasing and about one in every nine women in the developed world is believed to get breast cancer in her lifetime. Although lifestyle changes related to female steroid hormones, including exposure to exogenous hormones, affect the risk of developing breast cancer, these factors only make up for a small fraction of the etiology, and the benefit of preventive manipulation is believed to be low. The decreased mortality is mainly due to earlier detection by mammography screening and the use of modern adjuvant systemic treatment.

Treatment of Breast Cancer

Since its introduction in the late seventies, breast-conserving therapy, combining breast conserving surgery and post-operative radiotherapy, has become the primary treatment of choice in women where radical removal of the tumor can be combined with a good cosmetic result. Mastectomy is still preferable in some patients, i.e., women with small breasts, large tumors (>4 cm) or multifocal/multicentric disease.

Axillary dissection is primarily performed for diagnostic purposes and removal of at least 10 lymph nodes gives a good staging guidance with 97-98% sensitivity (Axelsson C K et al. (1992) Eur J Cancer 28A:1415-8; Recht A and Houlihan M J (1995) Cancer 6(9):1491-1512). However, the next step towards minimal surgery in the treatment of primary cancer has been the introduction of the sentinel node biopsy technique with mapping of axillary lymph nodes instead of axillary lymph node clearance, which is associated with a high complication rate. This technique was introduced as a consequence of the knowledge that most of the lymphatic drainage to the axilla from the breast initially passes through one (or a few) lymph node(s)—the sentinel node(s)—supporting that analysis of this lymph node may be a sufficient indicator of axillary node status (Veronesi U et al. (2003) New Engl J Med 349(6): 546-53.)

The concept of breast cancer as a systemic disease, i.e., the presence of disseminating micro-metastases at the time of diagnosis that may explain treatment failure after locoregional therapy, paved the way for adjuvant randomized trials in the 1970s, including endocrine therapy and chemotherapy. Adjuvant polychemotherapy is standard treatment for hormone-receptor negative patients with high risk of recurrence, irrespective of nodal status. A beneficial effect on both overall- and relapse-free survival has been demonstrated, especially in premenopausal patients (EBCTCG (1998) Lancet 352(9132): 930-42). For patients with hormone-responsive disease, e.g., estrogen receptor (ER) and/or progesterone receptor (PR) positive disease, adjuvant polychemotherapy has been delivered in combination with endocrine therapy as sequential chemo-endocrine therapy. Also, adjuvant chemotherapy generally induces amenorrhea, causing a secondary endocrine effect in addition to the cytotoxic (Pagani O et al. (1998) Eur J Cancer 34(5):632-40).

Endocrine therapy has been recommended for patients with hormone receptor positive tumors irrespective of age, stage and menopausal status.

In hormone-responsive premenopausal patients, ovarian ablation by surgery or irradiation, or ovarian suppression by LHRH agonists is efficient adjuvant treatment modalities (Emens L A and Davidson N A (2003) Clin Ca Res (1 Pt 2): 468S-94S). In postmenopausal patients, ovarian ablation has no place, since the primary source of estrogen is not from ovarian synthesis but from the conversion of androstenedione to estrone and estradiol in peripheral tissues including the breast.

Tamoxifen is a selective estrogen receptor modulator (SERM) with an agonistic effect on the ER, making it a suitable treatment for advanced breast cancer in both pre- and postmenopausal women. Studies have shown that five years of tamoxifen as adjuvant treatment after primary surgery reduces the breast cancer mortality in patients with ER positive (ER+) tumors, irrespective of lymph node status (EBCTCG (1998) Lancet 351(9114):1451-67). While tamoxifen has a protective effect against cardiovascular disease, the risk of developing endometrial cancer is increased, due to an agonistic effect on the ER in the endometrium (EBCTCG (2005) Lancet 365(9472):1687-717)

Aromatase inhibitors (AIs) function by inhibiting aromatase, the enzyme converting androgens into estrogens. For example, AIs can be given as adjuvant treatment to postmenopausal women, either alone or following tamoxifen treatment and they have been shown to significantly reduce the mortality, possibly even more if given alone (Howell A et al. (1995) Lancet 345(8941):29-30; Ellis M J and Rigden C E (2006) Curr Med Res Opin 22(12):2479-87; Coates A S et al. (2007) J Clin Oncol 25(5):486-92). However, this therapy is relatively new and the long-term side effects are not yet fully known (Buzdar A et al. (2006) Lancet Oncol 7(8):633-43), but the most important are cardiovascular complications and osteoporosis.

Newly developed pure anti-estrogens such as fulvestrant, which completely blocks the ER, are currently only used in advanced breast cancer and not in the adjuvant setting (Rutqvist L E (2004) Best Pract Res Clin Endocrinol Metab 18(1): 81-95).

Adjuvant endocrine therapy is believed to have no place in hormone receptor negative breast cancer, although some studies indicate that some ER negative i.e., ERα negative (ERα−), tumors respond to tamoxifen treatment (EBCTCG (1998) Lancet 351:1451-1467)

The HER2/neu gene is overexpressed in about 20% of all, and in up to 70% of lowly differentiated, breast cancers (Berger M S et al. (1988) Cancer Res 48(5):1238-43; Borg A et al. (1990) Cancer Res 50(14): 4332-7). Patients with HER2 overexpressing tumors may benefit from treatment with the monoclonal antibody trastuzumab. Experimental data support a relationship between HER2 overexpression and resistance to endocrine treatment (Shou J et al. (2004) J Natl Cancer Inst 96(12):926-35) while clinical data are not consistent (Borg Å et al. (1994) Cancer Lett 81(2):137-44, De Placido S et al. (2003) Clin Ca Res 9(3):1039-46, Rydén L et al. (2005) J Clin Oncol 23(21):4695-704).

Breast Cancer Diagnostics

Morphologic criteria are still generally considered important in the establishment of a breast cancer diagnosis, both in situ and invasive cancer. Among invasive breast carcinomas, invasive ductal carcinoma is the most common tumor type (~80%) and lobular carcinoma is the second largest entity (~10-15%). Tubular and medullary carcinomas are other distinct types with lower prevalence (WHO, Histological typing of breast tumors, in International histological classification of tumors no:2, 1981, WHO, Geneva).

Breast Cancer Prognostics and Treatment Predictive Factors

A correct histological classification of the tumor type may be of prognostic relevance, since certain subtypes, such as medullary carcinomas, in general have a more favorable prognosis. Nevertheless, assessment of the histological grade using the Nottingham Histological Grade (NHG) system is still a prognostic tool (Elston C W and Ellis I O (1991) 19(5):403-10; Sundquist Metal. (1999) *Breast Cancer Res Treat* 53(1):1-8).

The majority of breast cancers are hormone receptor responsive, i.e., express the ER and/or PR. The action of estrogen is mediated by the two receptors ERα and ERβ. ERα and PR are routinely assessed in order to select patients for endocrine therapy, and according to one standard, tumors with >10% nuclear positivity are considered positive. ERα is today considered a predictor of tamoxifen response. However, there are studies that indicate that PR positivity may even be a more powerful predictor of tamoxifen response than ERα. A study of premenopausal patients randomized to tamoxifen or no adjuvant endocrine treatment revealed that a high expression (>75% nuclear fraction) of PR was significantly associated with an increased recurrence-free and overall survival in tamoxifen treated patients, irrespectively of ERα status. At a lower PR level, <75%, no positive effect from tamoxifen treatment was observed (Stendahl M et al. (2006) *Clin Cancer Res* 12:4614-18). Yu et al. recently studied the predictive value of PR for adjuvant endocrine therapy, and found that older patients (≥60 years) with ERα+/PR+ tumors had a significantly longer disease free survival when treated with tamoxifen than patients that received no adjuvant treatment. In younger patients (<60 years), no significant effect was observed (Yu K D et al. (2007) The Breast 16:307-315). Interestingly, a report from the ATAC trial (postmenopausal women treated with arimidex, tamoxifen or in combination), showed that the recurrence rate was halved for anastrozole-treated patients with ERα+/PR− tumors over the follow-up period of 6 years, compared to patients treated with tamoxifen (Dowsett M et al. (2005) J Clin Oncol 23(30): 7512-7).

The role of ERβ in breast cancer is not yet fully clarified, although recent studies implicate that ERβ-expression may be associated with a better tamoxifen response (Borgquist S et al, (2008) J Clin Pathol 61(2):197-203), particularly in ERα− tumors (Gruvberger-Saal S K et al. (2007) Clin Cancer Res 13:1987-1994). However, determination of ERβ is today generally not considered clinically relevant.

A major problem to day is that 30-40% of the ERα positive (ERα+) patients do not respond to tamoxifen treatment (Riggins R B et al. (2007) Cancer Letters 1:1-24, Gruvberger-Saal S K et al. (2007) Clin Cancer Res 13:1987-1994), which results in unnecessary treatment. In addition, a fraction of the ERα− patients do respond to tamoxifen treatment, and the reason for that is currently not known. Gruvberger-Saal suggests that ERβ expression may be a positive predictor of tamoxifen response in ERα− patients (Gruvberger-Saal S K et al. (2007) Clin Cancer Res 13:1987-1994).

HER2 status is also assessed routinely, primarily by IHC and in cases with moderate expression (2+), gene amplification status is determined by fluorescence in situ hybridization (FISH) analysis. Patients with a HER2 positive tumor may benefit from treatment with trastuzumab.

Breast cancer is a truly heterogeneous disease and despite the increasing understanding of its nature, the arsenal of available prognostic and treatment predictive markers is still not sufficient and some patients may therefore receive unnecessary treatment while others may get insufficient or even ineffective treatment. Additional molecular markers are needed in order to better define different subgroups of breast cancer and increase the options for tailored therapies.

Endpoint Analysis

Endpoint analysis is used to evaluate trials with adjuvant treatments for cancer as this gives information on how the patients respond to a certain therapy. Endpoint analysis may also be useful for studies of a potential biomarker.

Overall survival (OS) has been considered the standard primary endpoint. OS takes in to account time to death, irrespective of cause, e.g., if the death is due to cancer or not. Loss to follow-up is censored and regional recurrence, distant metastases, second primary breast cancers, and second other primary cancers are ignored.

To date, an increasing number of effective treatments available in many types of cancer have resulted in the need for surrogate endpoints to allow for a better evaluation of the effect of adjuvant treatments. Thus, the much longer follow-up required to demonstrate that adjuvant treatments improve OS is often complemented with other clinical endpoints that give an earlier indication on how successful the treatment is. For these observations, recurrence-free survival (RFS) and breast cancer-specific survival (BCSS) may be analyzed. RFS includes time to any event related to the same cancer, i.e., all cancer recurrences and deaths from the same cancer are events. Distant, local and regional metastases as well as breast cancer specific death are considered. On the other hand, second primary same cancers and other primary cancers are ignored, as well as contralateral breast cancer. Deaths from other cancers, non-cancer-related deaths, treatment-related deaths, and loss to follow-up are censored observations. Breast cancer-specific survival (BCSS) includes time to death caused by breast cancer due to the original tumor. Both endpoints are relevant, since similarities or differences may reflect different tumor biological behaviors. Biomarkers associated with a locally aggressive behavior may for instance have greater impact on RFS than BCSS, while biomarkers associated with the development of distant metastases may be reflected in both RFS and BCSS.

SUMMARY

The present disclosure can be summarized in the following itemized embodiments:

1. Method for determining whether a mammalian subject having a breast cancer is likely to benefit from an endocrine treatment, comprising the steps of:
   a) providing a sample earlier obtained from said subject;
   b) evaluating the amount of HMGCR protein or HMGCR mRNA present in at least part of said sample, and determining a sample value corresponding to said amount;
   c) comparing the sample value obtained in step b) with a reference value; and,
      if said sample value is higher than said reference value,
   d) concluding that the subject is likely to benefit from an endocrine treatment.

2. Non-treatment strategy method for a mammalian subject having a breast cancer, comprising:
   a) providing a sample earlier obtained from said subject;
   b) evaluating the amount of HMGCR protein or HMGCR mRNA present in at least part of said sample, and determining a sample value corresponding to said amount;

c) comparing the sample value obtained in step b) with a reference value; and,
   if said sample value is lower than or equal to said reference value,
d) refraining from treating said subject with an endocrine treatment.

3. Method according to any one of items 1 and 2, wherein said breast cancer is ER negative or PR negative.

4. Method according to item 3, wherein said breast cancer is ER negative.

5. Method for determining whether a mammalian subject having a breast cancer is likely to benefit from an endocrine treatment, comprising the steps of:
   a) providing a sample earlier obtained from said subject;
   b) evaluating the amount of HMGCR protein or HMGCR mRNA present in at least part of said sample, and determining a sample value corresponding to said amount;
   c) comparing the sample value obtained in step c) with a reference value and thereby determining the HMGCR status of said subject;
   d) obtaining the ER status for said subject; and
      if said ER status or said HMGCR status is positive,
   e1) concluding that the subject is likely to benefit from an endocrine treatment, or
      if said ER status and said HMGCR status are negative,
   e2) concluding that the subject is not likely to benefit from the endocrine treatment.

6. Method according to item 5, wherein the ER status is obtained from the sample of step a).

7. Method according to any one of the preceding items, wherein said endocrine treatment is selected from a SERM treatment, an aromatase inhibitor treatment, and a steroidal estrogen receptor antagonist treatment.

8. Method according to any one of the preceding items, wherein said endocrine treatment is a SERM treatment and said SERM is selected from toremifene, raloxifene, droloxifene, arzoxifene and tamoxifen.

9. Method according to any one of the preceding items, wherein said endocrine treatment is tamoxifen treatment.

10. Method according to any one of the preceding items, wherein said sample is a body fluid sample.

11. Method according to item 10, wherein the body fluid is selected from the group consisting of blood, plasma, serum, cerebral fluid, urine and exudate.

12. Method according to any one of items 1-9, wherein said sample is a cytology sample.

13. Method according to any one of items 1-9, wherein said sample is a stool sample.

14. Method according to any one of the preceding items, wherein said sample comprises cells from said subject.

15. Method according to any one of the preceding items, wherein said sample comprises tumor cells from said subject.

16. Method according to any one of items 1-9, wherein said sample is a tissue sample.

17. Method according to item 16, wherein said tissue sample is a breast cancer tissue sample.

18. Method according to any one of items 14-17, wherein the evaluation of step b) is limited to the cytoplasms of cells of said sample.

19. Method according to item 18, wherein said cells of said sample are tumor cells.

20. Method according to any one of the preceding items, wherein said subject is a human female.

21. Method according to any one of the preceding items, wherein said subject is a premenopausal female.

22. Method according to any one of the preceding items, wherein said breast cancer is a stage II breast cancer.

23. Method according any one of the preceding items, wherein said breast cancer is a node positive breast cancer.

24. Method according to any one of the preceding items, wherein said reference value is a value corresponding to an amount of HMGCR protein or HMGCR mRNA in a reference sample.

25. Method according to any one of the preceding items, wherein said sample value of step b) is determined as being either 1, corresponding to detectable HMGCR protein or HMGCR mRNA in said sample, or 0, corresponding to no detectable HMGCR protein or HMGCR mRNA in said sample.

26. Method according to any one of the preceding items, wherein said reference value of step c) corresponds to a reference sample having no detectable HMGCR protein or HMGCR mRNA.

27. Method according to any one of the preceding items, wherein said reference value of step c) is 0.

28. Method according to any one of the preceding items, wherein said reference value is selected from the group consisting of a cytoplasmic fraction, a cytoplasmic intensity, a function of a cytoplasmic fraction and a cytoplasmic intensity, a nuclear fraction, a nuclear intensity and a function of a nuclear fraction and a nuclear intensity.

29. Method according to any one of the preceding items, wherein said reference value is selected from the group consisting of a cytoplasmic fraction, a cytoplasmic intensity and a function of a cytoplasmic fraction and a cytoplasmic intensity.

30. Method according to any one of the preceding items, wherein said reference value is a cytoplasmic fraction of 50% HMGCR protein positive cells, or lower.

31. Method according to any one of the preceding items, wherein said reference value is a cytoplasmic fraction of 25% HMGCR protein positive cells, or lower.

32. Method according to any one of the preceding items, wherein said reference value is a cytoplasmic fraction of 10% HMGCR protein positive cells, or lower.

33. Method according to any one of items 1-29, wherein said reference value is a weak cytoplasmic intensity of HMGCR protein expression, or lower.

34. Method according to any one of items 1-29 and 33, wherein said reference value is an absent cytoplasmic intensity of HMGCR protein expression.

35. Method according to any one of items 1-29, wherein said reference value is a cytoplasmic fraction of 25% HMGCR protein or lower or a weak cytoplasmic intensity of HMGCR protein expression or lower.

36. Method according to any one of the preceding items, wherein the amino acid sequence of the HMGCR protein comprises a sequence selected from:
   i) SEQ ID NO:1; and
   ii) a sequence which is at least 85% identical to SEQ ID NO:1.

37. Method according to any one of the preceding items, wherein the amino acid sequence of the HMGCR protein comprises a sequence selected from:
   i) SEQ ID NO:2; and
   ii) a sequence which is at least 85% identical to SEQ ID NO:2.

38. Method according to any one of the preceding items, wherein step b) comprises:
   b1) applying to said sample a quantifiable affinity ligand capable of selective interaction with the HMGCR protein to be evaluated, said application being performed under conditions that enable binding of said affinity ligand to any HMGCR protein present in said sample;

b2) removing non-bound affinity ligand; and
b3) quantifying the affinity ligand remaining in association with said sample to evaluate said amount.

39. Method according to item 38, wherein said quantifiable affinity ligand is selected from the group consisting of antibodies, fragments thereof and derivatives thereof.

40. Method according to item 39, wherein said quantifiable affinity ligand is obtainable by a process comprising a step of immunizing an animal with a protein whose amino acid sequence comprises the sequence SEQ ID NO:1.

41. Method according to item 40, wherein said quantifiable affinity ligand is obtainable by a process comprising a step of immunizing an animal with a protein whose amino acid sequence consists of the amino acid sequence SEQ ID NO:1.

42. Method according to item 38, wherein said quantifiable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

43. Method according to item 38, wherein said quantifiable affinity ligand is an oligonucleotide molecule.

44. Method according to any one of items 38-43, wherein said quantifiable affinity ligand is capable of selective interaction with an HMGCR protein whose amino acid sequence consists of the sequence of SEQ ID NO:1 or SEQ ID NO:4.

45. Method according to any one of items 38-44, wherein said quantifiable affinity ligand comprises a label selected from the group consisting of fluorescent dyes and metals, chromophoric dyes, chemiluminescent compounds and bioluminescent proteins, enzymes, radioisotopes, particles and quantum dots.

46. Method according to any one of items 38-45, wherein said quantifiable affinity ligand is detected using a secondary affinity ligand capable of recognizing said quantifiable affinity ligand.

47. Method according to item 46, wherein said secondary affinity ligand is capable of recognizing said quantifiable affinity ligand comprises a label selected from the group consisting of fluorescent dyes and metals, chromophoric dyes, chemiluminescent compounds and bioluminescent proteins, enzymes, radioisotopes, particles and quantum dots.

48. Kit for carrying out the method according to any one of the preceding items, which comprises
a) a quantifiable affinity ligand capable of selective interaction with an HMGCR protein; and
b) reagents necessary for quantifying the amount of said quantifiable affinity ligand.

49. Kit according to item 48, in which said quantifiable affinity ligand is selected from the group consisting of antibodies, fragments thereof and derivatives thereof.

50. Kit according to item 49, in which said quantifiable affinity ligand is obtainable by a process comprising a step of immunizing an animal with a protein whose amino acid sequence comprises the sequence SEQ ID NO:1.

51. Kit according to item 49, in which said quantifiable affinity ligand is obtainable by a process comprising a step of immunizing an animal with a protein whose amino acid sequence consists of the sequence SEQ ID NO:1.

52. Kit according to any of one of items 48, in which said quantifiable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

53. Kit according to any of one of items 48, in which said quantifiable affinity ligand is an oligonucleotide molecule.

54. Kit according to any one of items 48-53, in which said quantifiable affinity ligand is capable of selective interaction with an HMGCR protein comprising, or consisting of, a sequence selected from:
i) SEQ ID NO:1; and
ii) a sequence which is at least 85% identical to SEQ ID NO:1.

55. Kit according to any one of items 48-54, in which said quantifiable affinity ligand is capable of selective interaction with an HMGCR protein comprising, or consisting of, a sequence selected from:
i) SEQ ID NO:2; and
a sequence which is at least 85% identical to SEQ ID NO:2.

56. Kit according to any one of items 48-55, in which said quantifiable affinity ligand is capable of selective interaction with an HMGCR protein comprising, or consisting of, the sequence SEQ ID NO:4.

57. Kit according to any one of items 48-56, in which said quantifiable affinity ligand comprises a label selected from the group consisting of fluorescent dyes and metals, chromophoric dyes, chemiluminescent compounds and bioluminescent proteins, enzymes, radioisotopes, particles and quantum dots.

58. Kit according to any one of items 48-57, in which said reagents necessary for quantifying said amount of said quantifiable affinity ligand comprise a secondary affinity ligand capable of recognizing said quantifiable affinity ligand.

59. Kit according to item 58, in which said secondary affinity ligand comprises a label selected from the group consisting of fluorescent dyes or metals, chromophoric dyes, chemiluminescent compounds and bioluminescent proteins, enzymes, radioisotopes, particles and quantum dots.

60. Kit according to any one of items 48-59, further comprising at least one reference sample for provision of a reference value.

61. Kit according to item 60, in which at least one reference sample is a tissue sample comprising no detectable HMGCR protein.

62. Kit according to item 60 or 61, in which at least one reference sample comprises HMGCR protein.

63. Kit according to any one of items 60-62, in which at least one reference sample comprises an amount of HMGCR protein corresponding to a cytoplasmic fraction of 50%, or lower.

64. Kit according to item 63, in which at least one reference sample comprises an amount of HMGCR protein corresponding to a cytoplasmic fraction of 25%, or lower.

65. Kit according to item 64, in which at least one reference sample comprises an amount of HMGCR protein corresponding to a cytoplasmic fraction of 10%, or lower.

66. Kit according to item 65, in which at least one reference sample comprises an amount of HMGCR protein corresponding to a cytoplasmic fraction of 1%, or lower.

67. Kit according to any one of items 60-66, in which at least one reference sample comprises an amount of HMGCR protein corresponding to a weak cytoplasmic intensity, or lower.

68. Kit according to item 67, in which at least one reference sample comprises an amount of HMGCR protein corresponding to an absent cytoplasmic intensity.

69. Kit according to any one of items 60-68, in which at least one reference sample comprises an amount of HMGCR protein corresponding to a value being higher than said reference value.

70. Kit according to item 69, in which at least one reference sample comprises an amount of HMGCR protein corresponding to a strong cytoplasmic intensity.

71. Kit according to item 69 or 70, in which at least one reference sample comprises an amount of HMGCR protein corresponding to a cytoplasmic fraction of 75% or higher.

72. Kit according to any one of items 60-71 comprising:
a first reference sample comprising an amount of HMGCR protein corresponding to a value (positive reference value) being higher than a reference value; and
a second reference sample comprising an amount of HMGCR protein corresponding to a value (negative reference value) being lower than or equal to said reference value.

73. Kit according to any one of items 60-72, in which said reference sample(s) is/are tissue sample(s).

74. Kit according to any one of items 48-73, further comprising
a') a quantifiable affinity ligand capable of selective interaction with an estrogen receptor; and
b') reagents necessary for quantifying the amount of the quantifiable affinity ligand of a').

75. Kit according to any one of items 48-74, further comprising
a") a quantifiable affinity ligand capable of selective interaction with a progesterone receptor; and
b") reagents necessary for quantifying the amount of the quantifiable affinity ligand of a").

76. Use of a HMGCR protein or HMGCR mRNA as an endocrine treatment indicating marker for a mammalian subject having a breast cancer.

77. Use of a HMGCR protein, or an antigenically active fragment thereof, in the manufacture of an endocrine treatment indicating agent for a mammalian subject having a breast cancer.

78. Use of a HMGCR protein, or an antigenically active fragment thereof, for the production, selection or purification of an endocrine treatment indicating agent for a mammalian subject having a breast cancer.

79. Use according to item 78, wherein said endocrine treatment indicating agent is an affinity ligand capable of selective interaction with the HMGCR protein, or an antigenically active fragment thereof.

80. Use according to item 79, wherein the affinity ligand is capable of selective interaction with a protein consisting of the sequence SEQ ID NO:1.

81. Use according to anyone of items 76-80, wherein the amino acid sequence of the HMGCR protein comprises, or consists of, a sequence selected from:
i) SEQ ID NO:1; and
ii) a sequence which is at least 85% identical to SEQ ID NO:1.

82. Use according to anyone of items 76-80, wherein the amino acid sequence of the HMGCR protein comprises, or consists of, a sequence selected from:
i) SEQ ID NO:2; and
ii) a sequence which is at least 85% identical to SEQ ID NO:2.

83. Affinity ligand, capable of selective interaction with an HMGCR protein, for in vivo use as an endocrine treatment indicating agent in a mammalian subject having a breast cancer 84. Affinity ligand, capable of selective interaction with an HMGCR protein, for in vivo evaluation an amount of HMGCR protein in a subject having a breast cancer.

85. Affinity ligand according to any one of items 83-84, which is obtainable by a process comprising a step of immunizing an animal with a protein whose amino acid sequence comprises the sequence SEQ ID NO:1.

86. Affinity ligand according to item 85, which is obtainable by a process comprising a step of immunizing an animal with a protein whose amino acid sequence consists of the sequence SEQ ID NO:1.

87. Affinity ligand according to any one of items 83-86, capable of selective interaction with a polypeptide consisting of the sequence SEQ ID NO:1.

88. Affinity ligand according to any one of items 83-86, capable of selective interaction with a polypeptide consisting of the sequence SEQ ID NO:4.

89. Use in vitro of an affinity ligand according to any one of items 83-88 as an endocrine treatment indicating agent for a mammalian subject having a breast cancer.

90. Use in vitro of an affinity ligand according to any one of items 83-88 for indicating whether a mammalian subject having a breast cancer would benefit from an endocrine treatment.

91. Use of the affinity ligand according to any one of items 83-88 in the manufacture of an endocrine treatment indicating agent for a mammalian subject having a breast cancer.

92. Endocrine treatment product for use in treatment of a mammalian subject having a breast cancer, wherein said subject is HMGCR positive.

93. Endocrine treatment product according to item 92, wherein said breast cancer is ER negative or PR negative.

94. Endocrine treatment product according to item 92 or 93 being tamoxifen.

95. Use of an endocrine treatment product in the manufacture of a medicament for treatment of a mammalian subject having a breast cancer, wherein said subject is HMGCR positive.

96. Use according to item 95, wherein said breast cancer is ER negative or PR negative.

97. Use according to item 95 or 96, wherein the endocrine treatment product is tamoxifen.

98. Kit-of-parts including an endocrine treatment product and a statin.

99. Kit-of-parts according to item 98 for use in therapy.

100. Kit-of-parts according to item 99 for use in breast cancer therapy.

101. Products including an endocrine treatment product and a statin as a combined preparation for simultaneous, separate or sequential use in therapy.

102. Products including an endocrine treatment product and a statin as a combined preparation for simultaneous, separate or sequential use in breast cancer therapy.

103. Method of treatment of a mammalian subject in need thereof, wherein said subject has a breast cancer, comprising the steps of:
a) providing a sample from said subject;
b) evaluating the amount of HMGCR protein or HMGCR mRNA present in at least part of said sample, and determining a sample value corresponding to said amount;
c) comparing the sample value obtained in step b) with a reference value; and,
if said sample value is higher than said reference value,
d) treating said subject with an endocrine treatment regimen.

104. Method according to item 103, wherein said breast cancer is ER negative or PR negative.

105. Method according to item 104, wherein said breast cancer is ER negative.

106. Method of treatment of a mammalian subject in need thereof, wherein said subject has a breast cancer, comprising the steps of:
   a) providing a sample from said subject;
   b) evaluating the amount of HMGCR protein or HMGCR mRNA present in at least part of said sample, and determining a sample value corresponding to said amount;
   c) comparing the sample value obtained in step c) with a reference value and thereby determining the HMGCR status of said subject;
   d) obtaining the ER status for said subject; and
      if said ER status or said HMGCR status is positive,
   e1) treating said subject with an endocrine treatment regimen, or
      if said ER status and said HMGCR status are negative,
   e2) treating said subject with a non-endocrine treatment regimen.

107. Method according to item 106, wherein the ER status is obtained from the sample of step a).

108. Method according to any one of items 103-107, wherein said endocrine treatment is selected from a SERM treatment, an aromatase inhibitor treatment, and a steroidal estrogen receptor antagonist treatment.

109. Method according to any one of items 103-108, wherein said endocrine treatment is a SERM treatment and said SERM is selected from toremifene, raloxifene, droloxifene, arzoxifene and tamoxifen.

110. Method according to any one of items 103-109, wherein said endocrine treatment is tamoxifen treatment.

111. Method according to any one of items 103-110, wherein said sample is a body fluid sample.

112. Method according to item 111, wherein the body fluid is selected from the group consisting of blood, plasma, serum, cerebral fluid, urine and exudate.

113. Method according to any one of items 103-110, wherein said sample is a cytology sample.

114. Method according to any one of items 103-110, wherein said sample is a stool sample.

115. Method according to any one of items 103-114, wherein said sample comprises cells from said subject.

116. Method according to any one of items 103-115, wherein said sample comprises tumor cells from said subject.

117. Method according to any one of items 103-110, wherein said sample is a tissue sample.

118. Method according to item 117, wherein said tissue sample is a breast cancer tissue sample.

119. Method according to any one of items 115-118, wherein the evaluation of step b) is limited to the cytoplasms of cells of said sample.

120. Method according to item 119, wherein said cells of said sample are tumor cells.

121. Method according to any one of items 103-120, wherein said subject is a human female.

122. Method according to any one of items 103-121, wherein said subject is a premenopausal female.

123. Method according to any one of items 103-122, wherein said breast cancer is a stage II breast cancer.

124. Method according to any one of items 103-123, wherein said breast cancer is a node positive breast cancer.

125. Method according to any one of items 103-124, wherein said reference value is a value corresponding to an amount of HMGCR protein or HMGCR mRNA in a reference sample.

126. Method according to any one of items 103-125, wherein said sample value of step b) is determined as being either 1, corresponding to detectable HMGCR protein or HMGCR mRNA in said sample, or 0, corresponding to no detectable HMGCR protein or HMGCR mRNA in said sample.

127. Method according to any one of items 103-126, wherein said reference value of step c) corresponds to a reference sample having no detectable HMGCR protein or HMGCR mRNA.

128. Method according to any one of items 103-127, wherein said reference value of step c) is 0.

129. Method according to any one of items 103-128, wherein said reference value is selected from the group consisting of a cytoplasmic fraction, a cytoplasmic intensity, a function of a cytoplasmic fraction and a cytoplasmic intensity, a nuclear fraction, a nuclear intensity and a function of a nuclear fraction and a nuclear intensity.

130. Method according to any one of items 103-129, wherein said reference value is selected from the group consisting of a cytoplasmic fraction, a cytoplasmic intensity and a function of a cytoplasmic fraction and a cytoplasmic intensity.

131. Method according to any one of items 103-130, wherein said reference value is a cytoplasmic fraction of 50% HMGCR protein positive cells, or lower.

132. Method according to any one of items 103-131, wherein said reference value is a cytoplasmic fraction of 25% HMGCR protein positive cells, or lower.

133. Method according to any one of items 103-132, wherein said reference value is a cytoplasmic fraction of 10% HMGCR protein positive cells, or lower.

134. Method according to any one of items 103-130, wherein said reference value is a weak cytoplasmic intensity of HMGCR protein expression, or lower.

135. Method according to any one of items 103-130 and 134, wherein said reference value is an absent cytoplasmic intensity of HMGCR protein expression.

136. Method according to any one of items 103-130, wherein said reference value is a cytoplasmic fraction of 25% HMGCR protein or lower or a weak cytoplasmic intensity of HMGCR protein expression or lower.

137. Method according to any one of items 103-136, wherein the amino acid sequence of the HMGCR protein comprises a sequence selected from:
   i) SEQ ID NO:1; and
   ii) a sequence which is at least 85% identical to SEQ ID NO:1.

138. Method according to any one of items 103-136, wherein the amino acid sequence of the HMGCR protein comprises a sequence selected from:
   i) SEQ ID NO:2; and
   ii) a sequence which is at least 85% identical to SEQ ID NO:2.

139. Method according to any one of items 103-138, wherein step b) comprises:
   b1) applying to said sample a quantifiable affinity ligand capable of selective interaction with the HMGCR protein to be evaluated, said application being performed under conditions that enable binding of said affinity ligand to any HMGCR protein present in said sample;
   b2) removing non-bound affinity ligand; and
   b3) quantifying the affinity ligand remaining in association with said sample to evaluate said amount.

140. Method according to item 139, wherein said quantifiable affinity ligand is selected from the group consisting of antibodies, fragments thereof and derivatives thereof.

141. Method according to item 140, wherein said quantifiable affinity ligand is obtainable by a process comprising a step of immunizing an animal with a protein whose amino acid sequence comprises the sequence SEQ ID NO:1.

142. Method according to item 141, wherein said quantifiable affinity ligand is obtainable by a process comprising a step of immunizing an animal with a protein whose amino acid sequence consists of the amino acid sequence SEQ ID NO:1.

143. Method according to item 139, wherein said quantifiable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

144. Method according to item 139, wherein said quantifiable affinity ligand is an oligonucleotide molecule.

145. Method according to any one of items 139-144, wherein said quantifiable affinity ligand is capable of selective interaction with an HMGCR protein whose amino acid sequence consists of the sequence of SEQ ID NO:1 or SEQ ID NO:4.

146. Method according to any one of items 139-145, wherein said quantifiable affinity ligand comprises a label selected from the group consisting of fluorescent dyes and metals, chromophoric dyes, chemiluminescent compounds and bioluminescent proteins, enzymes, radioisotopes, particles and quantum dots.

147. Method according to any one of items 139-146, wherein said quantifiable affinity ligand is detected using a secondary affinity ligand capable of recognizing said quantifiable affinity ligand.

148. Method according to item 147, wherein said secondary affinity ligand is capable of recognizing said quantifiable affinity ligand comprises a label selected from the group consisting of fluorescent dyes and metals, chromophoric dyes, chemiluminescent compounds and bioluminescent proteins, enzymes, radioisotopes, particles and quantum dots.

149. Method of treatment of a mammalian subject in need thereof, wherein said subject has a breast cancer, comprising simultaneous, separate or sequential administration of a statin and an endocrine treatment product.

150. Method according to item 149, wherein the endocrine treatment product is a SERM.

151. Method according to item 149 or 150, wherein the endocrine treatment product is tamoxifen.

152. Method according to any one of items 149-151, wherein said statin is a lipophilic/hydrophobic statin or a hydrophobic statin.

153. Method according to item 152, wherein said statin is a lipophilic/hydrophobic statin selected from fluvastatin, lovastatin, simvastatin, atorvastatin and cerivastatin.

DETAILED DESCRIPTION

It is an object of some aspects of the present disclosure to provide means, methods and/or uses useful in treatment prediction, in particular breast cancer treatment prediction, regarding a mammalian subject having a breast cancer.

An object of some other aspects of the present disclosure is to provide means, methods and/or uses useful in the treatment of such a subject.

Thus, as a first configuration of a first aspect of the present invention, there is provided a method for determining whether a mammalian subject having a breast cancer is likely to benefit from an endocrine treatment, comprising the steps of:
a) providing a sample earlier obtained from said subject;
b) evaluating the amount of HMGCR protein or HMGCR mRNA present in at least part of said sample, and determining a sample value corresponding to said amount;
c) comparing the sample value obtained in step b) with a reference value; and,
   if said sample value is higher than said reference value,
d) concluding that the subject is likely to benefit from an endocrine treatment.

Regarding step b) of the methods of the present disclosure, an increase in the amount of HMGCR protein or HMGCR mRNA typically results in an increase in the sample value, and not the other way around. However, in some embodiments, the evaluated amount may correspond to any of a predetermined number of discrete sample values. In such embodiments, a first amount and a second, increased, amount may correspond to the same sample value. In any case, an increase in the amount of HMGCR protein or HMGCR mRNA will not result in a decrease in the sample value in the context of the present disclosure.

However inconvenient, but in an equivalent fashion, the evaluated amounts may be inversely related to sample values if the qualification between step c) and d) is "if the sample value is lower than the reference value" (see the method above). This applies mutatis mutandis to the other method aspects, configurations and embodiments of the present disclosure.

In the context of the present disclosure, "likely to benefit from an endocrine treatment" refers to a having a higher probability of survival or recovery if undergoing an endocrine treatment than if not undergoing an endocrine treatment. In this context, "recovery" refers to return from a breast cancer state to a breast cancer free state. The "survival" may be a recurrence free survival or a breast cancer specific survival. Further, the "recovery" may be a recurrence free recovery. Also, the "higher probability" may be a probability benefit at five years, ten years or 15 years of at least 5%, such as at least 10%.

This first aspect of the present disclosure is based on the previously unrecognized fact that the expression of HMGCR protein or HMGCR mRNA in a sample obtained from a subject having a breast cancer may serve as an indicator of response to endocrine treatment in the subject. More particularly, the inventors have identified that, in patients suffering from breast cancer, a correlation between values of HMGCR protein or HMGCR mRNA on the one hand and the survival after endocrine treatment on the other. Typically, high HMGCR values are shown herein to correlate with responsiveness to endocrine treatment. The present disclosure, based on HMGCR protein or HMGCR mRNA expression as a breast cancer treatment indicator, provides for a number of benefits. Firstly, it provides an additional, or alternative, tool for predicting whether a patient is likely to respond to endocrine treatment. Secondly it identifies a subgroup of hormone receptor negative patients that, contrary to earlier beliefs, benefit from to endocrine treatment. Consequently, the present disclosure may provide for accurate treatment of a previously undertreated group. Thirdly, the present disclosure identifies a subgroup of breast cancer patient which generally do not benefit from endocrine treatment. The analysis of the level of HMGCR protein or HMGCR mRNA according to the present disclosure may also be included in a panel analysis.

Traditionally, subjects with hormone receptor negative breast cancers, especially ER– breast cancers, have not received systemic endocrine treatment. However, as shown in the present disclosure, the survival rates in the subgroup of subjects with hormone receptor negative, e.g. ER– or PR–, ER–, PR–, or ER– and PR–, breast cancers having high HMGCR values were improved with endocrine treatment. Consequently, the inventors have identified new subgroups of subjects that may be treated with an endocrine treatment. Accordingly, various aspects of the present disclosure may be particularly relevant for the subjects having hormone receptor negative cancers.

As a second configuration of the first aspect, there is provided a method for determining whether a mammalian subject having a breast cancer should undergo an endocrine treatment, comprising the steps of:
a) providing a sample earlier obtained from said subject;
b) evaluating the amount of HMGCR protein or HMGCR mRNA present in at least part of said sample, and determining a sample value corresponding to said amount;
c) comparing the sample value obtained in step b) with a reference value; and,
if said sample value is higher than said reference value,
d) concluding that the subject should undergo an endocrine treatment.

As a third configuration of the first aspect of the present invention, there is provided a non-treatment strategy method for a mammalian subject having a breast cancer, comprising:
a) providing a sample earlier obtained from said subject;
b) evaluating the amount of HMGCR protein or HMGCR mRNA present in at least part of said sample, and determining a sample value corresponding to said amount;
c) comparing the sample value obtained in step b) with a reference value; and,
if said sample value is lower than or equal to said reference value,
d) refraining from treating said subject with an endocrine treatment.

For example, the refraining of step d) may be refraining during at least one week from the completion of steps a)-c), such as at least one month from the completion of steps a)-c), such as at least three months from the completion of steps a)-c), such as at least six months from the completion of steps a)-c), such as at least one year from the completion of steps a)-c), such as at least two years from the completion of steps a)-c).

Alternatively, the refraining of step d) may be refraining until the next time the method is performed or until recurrence of a breast cancer tumor.

In embodiments of configurations one to three of the first aspect, the breast cancer may be a hormone receptor negative breast cancer, such as an ER– or PR– breast cancer, an ER– breast cancer, a PR– breast cancer, or an ER– and PR– breast cancer. For example, the breast cancer may be previously diagnosed as hormone receptor negative.

In general, hormone receptor status, e.g. ER status or PR status, may be assessed according to any method known to the skilled artisan and the person skilled in the art knows how to obtain the ER and/or PR status of a patient. For example, such information may be obtained from the result of a test using the commercially available ER/PR pharmDX kit (DakoCytomation). As another example, the method disclosed by Allred et al. (Allred et al. (1998) Mod Pathol 11(2), 155) may be used to obtain a total score (Allred score), and, for both ER and PR, an Allred score of higher than two is considered positive and an Allred score of two or lower is considered negative. Alternatively, when classifying a sample as being positive or negative for ER or PR, a cutoff of 10% positive cells may be used, which is a recognized limit within the art.

The person skilled in the art knows how to obtain the ER and/or PR status of a patient. For example, such information may be obtained from the result of a test using the commercially available ER/PR pharmDX kit (DakoCytomation). As another example, the method disclosed by Allred et al. (Allred et al. (1998) Mod Pathol 11(2), 155) may be used to obtain a total score (Allred score), and, for both ER and PR, an Allred score of higher than two is considered positive and an Allred score of two or lower is considered negative. Alternatively, when classifying a sample as being positive or negative for ER or PR, a cutoff of 10% positive cells may be used, which is a recognized limit within the art.

If not otherwise stated, "ER" refers to "ERα" in the context of the present disclosure.

As a fourth configuration of the first aspect of the present invention, there is provided a method for determining whether a mammalian subject having a breast cancer is likely to benefit from an endocrine treatment, comprising the steps of:
a) providing a sample earlier obtained from said subject;
b) evaluating the amount of HMGCR protein or HMGCR mRNA present in at least part of said sample, and determining a sample value corresponding to said amount;
c) comparing the sample value obtained in step c) with a reference value and thereby determining the HMGCR status of said subject;
d) obtaining the ER status for said subject; and
if said ER status or said HMGCR status is positive,
e1) concluding that the subject is likely to benefit from an endocrine treatment, or
if said ER status and said HMGCR status are negative,
e2) concluding that the subject is not likely to benefit from the endocrine treatment.

However closely related and covered by the same concept, e1) and e2) provide two alternative conclusion options. Accordingly, the method of the fourth configuration of the first aspect may answer the question whether the subject having a breast cancer is likely to benefit from an endocrine treatment or the question whether the subject having a breast cancer is not likely to benefit from an endocrine treatment. Thus, the method of the fourth configuration of the first aspect may, but does not have to, comprise both step e1), together with its adherent qualification ("if phrase"), and step e2), together with its adherent qualification ("if phrase").

For example, in step c), the HMGCR status may be considered positive if the sample value is higher than the reference value and negative if the reference value is lower than, or equal to, the reference value.

A single sample from the subject may provide both the ER status and the HMGCR status, for example by means of immunohistochemistry. Thus, in embodiments of the method aspects of the present disclosure, the ER status may be obtained from the sample of step a). Also, the ER status may be obtained from a tissue material from which the sample of step a) was also obtained. Consequently, the required number of biopsies or amount of biological material from the subject may be kept low.

As a fifth configuration of the first aspect of the present disclosure, there is provided a method for determining whether a sample value corresponding to an amount of HMGCR protein or HMGCR mRNA present in at least part of a sample earlier obtained from a mammalian subject having a breast cancer is in favor of a decision to apply an endocrine treatment to the subject, comprising the steps of:

a) providing the sample earlier obtained from the subject;
b) evaluating the amount of HMGCR protein or HMGCR mRNA present in at least part of the sample, and determining the sample value corresponding to the amount;
c) comparing the sample value obtained in step b) with a reference value; and,
    if the sample value is higher than the reference value,
d1) concluding that the sample value is in favor of a decision to treat the subject with an endocrine treatment, and/or
    if the sample value is lower than or equal to the reference value,
d2) concluding that the sample value is in favor of a decision to refrain from treating the subject with an endocrine treatment.

However closely related and covered by the same concept, d1) and d2) of the fifth configuration of the first aspect provide two alternative conclusion options. Accordingly, the method may answer the question whether the sample value is in favor of a decision to refrain from treating the subject with an endocrine treatment or the question whether the sample value is in favor of a decision to treat the subject with an endocrine treatment. Thus, the method of the fifth configuration of the first aspect may, but does not have to, comprise both step d1), together with its adherent qualification ("if phrase"), and step d2), together with its adherent qualification ("if phrase").

When deciding on a suitable treatment strategy for a patient having breast cancer, the physician responsible for the treatment may take several parameters into account, such as the result of an immunohistochemical evaluation, patient age, hormone receptor status, general condition, medical history, such as breast cancer history and hereditary characteristics, e.g. whether there is a history of breast cancer in the subject's family. To be guided in such decision, the physician may perform a HMGCR test, or order an HMGCR test performed, according to the first aspect. In such case, a method according to the fifth configuration of the first aspect may be particularly relevant.

Also, the physician may instruct someone else, such as lab staff, to perform part of a method according to the present disclosure, such as steps a) to c), and perform the remaining, such as step d) or e), himself.

As a sixth configuration of the first aspect, there is provided a method for determining an endocrine treatment prediction regarding a mammalian subject having a breast cancer:
a) providing a sample from the subject;
b) evaluating the amount of HMGCR protein or HMGCR mRNA present in at least part of the sample, and determining a sample value corresponding to the evaluated amount;
c) correlating the sample value of step b) to the endocrine treatment prediction for the subject.

In an embodiment of the above method, the sample may be an earlier obtained sample.

The correlating of step c) refers to any way of associating survival data to the obtained sample value so as to establish the treatment prediction.

The identified correlation between high HMGCR protein or HMGCR mRNA expression and responsiveness to endocrine treatment may also form a basis for the application of a specific regimen for treatment of the subject. Thus, a first configuration of a second aspect of the present disclosure, there is provided a method of treatment of a mammalian subject in need thereof, wherein said subject has a breast cancer, comprising the steps of:

a) providing a sample from said subject;
b) evaluating the amount of HMGCR protein or HMGCR mRNA present in at least part of said sample, and determining a sample value corresponding to said amount;
c) comparing the sample value obtained in step b) with a reference value; and,
    if said sample value is higher than said reference value,
d) treating said subject with an endocrine treatment regimen.

In embodiments of the first configuration of the second aspect, the breast cancer may be a hormone receptor negative breast cancer, such as an ER– or PR– breast cancer, an ER– breast cancer, a PR– breast cancer, or an ER– and PR– breast cancer. For example, the breast cancer may be previously diagnosed as hormone receptor negative.

As a second configuration of the second aspect, there is provided a method of treatment of a mammalian subject in need thereof, wherein said subject has a breast cancer, comprising the steps of:
a) providing a sample from said subject;
b) evaluating the amount of HMGCR protein or HMGCR mRNA present in at least part of said sample, and determining a sample value corresponding to said amount;
c) comparing the sample value obtained in step c) with a reference value and thereby determining the HMGCR status of said subject;
d) obtaining the ER status for said subject; and
    if said ER status or said HMGCR status is positive,
e1) treating said subject with an endocrine treatment regimen, or
    if said ER status and said HMGCR status are negative,
e2) treating said subject with a non-endocrine treatment regimen.

However closely related and covered by the same concept, e1) and e2) of the second configuration of the second aspect provide two alternative conclusion options. Accordingly, the method may involve an endocrine treatment regimen or a non-endocrine treatment regimen. Thus, the method of the second configuration of the second aspect may, but does not have to, comprise both step e1), together with its adherent qualification ("if phrase"), and step e2), together with its adherent qualification ("if phrase").

Generally regarding the method of treatment aspects of the present disclosure, the physician responsible for the treatment of the subject may perform steps a) to c) himself or instruct someone else, such as lab staff, to perform them.

In the context of the present disclosure, an "endocrine treatment" refers to a systemic treatment with an anti-estrogenic effect. Further, "anti-estrogenic effect" refers to suppression of estrogen production or inhibition of estrogen effects in the body. In the art, an endocrine treatment is sometimes referred to as an anti-hormonal treatment.

The "endocrine treatment" of the present disclosure may be selected from the group consisting of a selective estrogen receptor modulator (SERM) treatment, an aromatase inhibitor treatment, and a steroidal estrogen receptor antagonist treatment. The SERM treatment may for example be a treatment selected from a toremifene, raloxifene, droloxifene, arzoxifene and tamoxifen treatment. The aromatase inhibitor treatment may for example be selected from anastrozole, letrozole and exemestane treatment. Further, the steroidal estrogen receptor antagonist treatment may be a treatment with fulvestrant.

A SERM may have either an agonistic or antagonistic effect depending on the target tissue. For example, a SERM may act as an antagonist in breast and as an agonist in uterus.

In the Examples section of the present disclosure, various results of treatment with the SERM tamoxifen are presented. The results show that the level of HMGCR protein or HMGCR mRNA expression is relevant for predicting whether the subjects are responsive to tamoxifen treatment. Thus, in preferred embodiments of the present disclosure, the endocrine treatment is tamoxifen treatment.

For example, the "non-endocrine treatment" of the present disclosure may be selected from chemotherapies, radiation therapies and combinations thereof. The chemotherapies comprise mono- or polychemotherapy, such as treatment with CMF (cyclophosphamide, methotrexate, 5-fluorouracil), FEC (fluorouracil, epirubicin, cyclofosfamid) and/or taxanes. Also, if the breast cancer is HER2 positive (HER2+), the non-endocrine treatment may be an anti-HER2 treatment, such as a treatment with an anti-HER2 antibody, e.g., trastuzumab.

In the context of the present disclosure, "a mammalian subject having a breast cancer" refers to a mammalian subject having a primary or secondary breast tumor or a mammalian subject which has had such tumor removed from the breast, wherein the removal of the tumor refers to killing or removing the tumor by any type of surgery or therapy. In the latter case, the tumor may for example have been removed less than one year ago. For example, a subject who has had a breast tumor removed by surgery and is about to get adjuvant therapy is considered "having a breast cancer" in the context of the present disclosure. "Breast tumor" includes ductal carcinoma in situ (DCIS). In the method and use aspects of the present disclosure, "a mammalian subject having a breast cancer" also includes the case wherein the mammalian subject is suspected of having a breast cancer at the time of the performance of the use or method and the breast cancer diagnosis is established later.

In the context of the method aspects of the present disclosure, "earlier obtained" refers to obtained before the method is performed. Consequently, if a sample earlier obtained from a subject is provided in a method, the method does not involve obtaining the sample from the subject, i.e., the sample was previously obtained from the subject in a step separate from the method.

Accordingly, all methods and uses of the present disclosure, may be performed entirely in vitro unless otherwise stated.

Step b) of the methods of the above aspects involve evaluating the amount of HMGCR protein or HMGCR mRNA present in at least part of the sample, and determining a sample value corresponding to the amount. The "at least part of the sample" refers to a relevant part, or relevant parts, of the sample for establishing a treatment prediction or drawing conclusions regarding suitable treatments. The person skilled in the art understands which part or parts that are relevant under the circumstances present when performing the method. For example, if the sample comprises tumor and non-tumor cells, the skilled person may only consider the tumor cells, and only the cytoplasms of the tumor cells, of the sample.

Further, in step b) an amount is evaluated and a sample value corresponding to the amount is determined. Consequently, an exact measurement of the amount of HMGCR protein or HMGCR mRNA is not required for obtaining the sample value. For example, the amount of HMGCR protein may be evaluated by visual inspection of a stained tissue sample and the sample value may then be categorized, e.g., as high or low based on the evaluated amount. The person skilled in the art understands how to perform such evaluation and determination.

Still further, in the context of the present disclosure, the "reference value" refers to a predetermined value which is relevant for making decisions, or drawing conclusions, regarding the treatment or treatment prediction.

The data of the present disclosure is based on groups of human females. Thus, in embodiments of the present disclosure, the "mammalian subject" may be a human. Also, in embodiments of the present disclosure, the "mammalian subject" may be a female, such as a premenopausal or postmenopausal female. Endocrine treatment is given to both premenopausal and postmenopausal subjects. Premenopausal females are generally considered to be more responsive to tamoxifen treatment. Thus, in some embodiments, in particular those wherein tamoxifen is selected as the endocrine treatment, premenopausal human female subjects may be a particularly relevant group.

The diagnosed or treated tumors of the present disclosure may be in any stage. However, the subjects studied as described in Examples, section 4 had stage II invasive breast cancers. Stage II refers to pT2 N0 M0 or pT1-2 N1 M0 according to the TNM staging system. Thus, in embodiments of the present disclosure, the "breast cancer" may be a stage II breast cancer.

Also, in embodiments of the present disclosure, the "breast cancer" may be a node negative or a node positive breast cancer (see e.g. FIGS. 4A and 4B). "Node negative cancer" and "node positive cancer" refers to a cancer that has and has not spread to the lymph nodes, respectively.

A seen in FIGS. 4A-7B, 9A and 9B, the treatment predictive role of HMGCR expression is particularly accentuated in node positive breast cancer. Thus, in embodiments of the present disclosure, the breast cancer may be node positive.

In embodiments of the methods of the above aspects, the sample may be a body fluid sample, such as a sample of blood, plasma, serum, cerebral fluid, lymph, urine or exudate. Preferably, the body fluid sample is sample of blood, plasma, serum or lymph. Alternatively, the sample may be a cytology sample or a stool sample.

The level of HMGCR protein expression may preferably be measured intracellularly. Thus, the body fluid, cytology or stool sample may for example comprise cells, such as tumor cells.

In further embodiments of the methods of the above aspects, the sample may be a tissue sample, such as a tumor tissue sample. As an example, the tissue sample may be derived from a primary breast tumor, such as an in situ or invasive carcinoma, or a secondary tumor (metastasis). Tissue samples facilitate HMGCR protein expression analysis by means of immunohistochemistry.

The inventors have found that the relevant HMGCR protein expression is primarily cytoplasmic. Thus, in embodiments of the methods of the present disclosure, the evaluation of step b) may be limited to the cytoplasms of cells, such as tumor cells, of the sample. When the evaluation is limited to the cytoplasms, only the characteristics, such as the HMGCR protein expression, of the cytoplasms are considered in the evaluation. Such evaluation may for example by aided by immunohistochemical staining.

The inventors have found that subjects who suffer from breast cancer and show essentially no HMGCR protein expression generally have poor survival after endocrine treatment (see Examples, section 4 and the figures). Consequently, the "cut-off value" determining whether the subject is "HMGCR high" or "HMGCR low" may be zero.

Thus, in embodiments of the methods of the present disclosure, the sample value of step b) may be either 1, corresponding to detectable HMGCR protein or HMGCR mRNA in the sample, or 0, corresponding to no detectable HMGCR protein or HMGCR mRNA in the sample. Consequently, in such embodiments, the evaluation of the sample is digital: HMGCR protein or HMGCR mRNA is considered to be either present or not. In the context of the present disclosure, "no detectable HMGCR protein or HMGCR mRNA" refers to an amount of HMGCR protein or HMGCR mRNA that is so small that it is not, during normal operational circumstances, detectable by a person or an apparatus performing the method according to any one of the above aspects. The "normal operational circumstances" refer to the laboratory methods and techniques a person skilled in the art would find appropriate for performing the invention.

Accordingly, in embodiments of the methods of the present disclosure, the reference value of step c) may be 0. And it follows that, in further embodiments of the methods of the present disclosure, the reference value of step c) may correspond to a reference sample having no detectable HMGCR protein or HMGCR mRNA (see below).

A sample value of HMGCR protein or HMGCR mRNA being higher than the reference value, or a subject from which such sample value is obtained, is sometimes referred to herein as "HMGCR high". Further, a sample value of HMGCR protein or HMGCR mRNA being lower than, or equal to, the reference value, or a subject from which such sample value is obtained, is sometimes referred to herein as "HMGCR low".

In the context of the present disclosure, the terms "sample value" and "reference value" are to be interpreted broadly. The quantification of HMGCR protein or HMGCR mRNA to obtain these values may be done via automatic means, via a scoring system based on visual or microscopic inspection of samples, or via combinations thereof. However, it is also possible for a skilled person, such as a person skilled in the art of histopathology, to determine the sample and reference values merely by inspection, e.g., of tissue slides that have been stained for HMGCR protein expression. The determination of the sample value being higher than the reference value may thus correspond to the determination, upon visual or microscopic inspection, that a sample tissue slide is more densely stained and/or exhibit a larger fraction of stained cells than is the case for a reference tissue slide. The sample value may also be compared to a reference value given by a literal reference, such as a reference value described in wording or by a reference picture. Consequently, the sample and/or reference values may in some cases be mental values that the skilled person determines upon inspection and comparison.

For example, the skilled person may categorize a sample as being HMGCR high or low, wherein the sample is categorized as high if it contains more HMGCR than a previously inspected reference sample and low if it contains less or equally much. Such evaluation may be assisted by staining the sample, and, if necessary, a reference sample, with a staining solution comprising e.g., antibodies selective for HMGCR protein.

A reference value, found to be relevant for making treatment decisions regarding breast cancer subjects, for use as comparison with the sample value from the subject, may be provided in various ways. With the knowledge of the teachings of the present disclosure, the skilled artisan can, without undue burden, provide relevant reference values for performing the methods of the present disclosure.

The person performing the methods of the above aspects may, for example, adapt the reference value to desired information. For example, the reference value may be adapted to yield the most significant treatment predictive information, e.g., the largest separation between the HMGCR high survival curve and the HMGCR low survival curve (see e.g., FIGS. 1A and 1B). An example of a reference value that may yield a large separation is an absent cytoplasmic intensity.

In embodiments of the methods of the above aspects, the reference value may correspond to the amount of HMGCR protein expression in a healthy tissue, such as healthy breast tissue, or stroma tissue of the subject of the method. As another example, the reference value may be provided by the amount of HMGCR protein or HMGCR mRNA expression measured in a standard sample of normal tissue from another, comparable subject. As another example, the reference value may be provided by the amount of HMGCR protein or HMGCR mRNA expression measured in a reference sample comprising (or being derived from) tumor cells, such as a reference sample of (or being derived from) tumor tissue, e.g., breast cancer tissue. The amount of protein or mRNA expression of the reference sample may preferably be previously established. Consequently, the reference value may be provided by the amount of HMGCR protein or HMGCR mRNA measured in a reference sample comprising cells expressing a predetermined amount of HMGCR protein or HMGCR mRNA.

Further, the reference value may for example be provided by the amount of HMGCR protein expression measured in a reference sample comprising cell lines, such as cancer cell lines, expressing a predetermined, or controlled, amount of HMGCR protein. The person skilled in the art understands how to provide such cell lines, for example guided by the disclosure of Rhodes et al. (2006) *The biomedical scientist*, p 515-520.

Consequently, in embodiments of the methods of the present disclosure, the reference value may be a predetermined value corresponding to the amount of HMGCR protein or HMGCR mRNA expression in a reference sample.

However, as discussed further below, the amount of HMGCR protein or HMGCR mRNA in the reference sample does not have to directly correspond to the reference value. The reference sample may also provide an amount of HMGCR protein or HMGCR mRNA that helps a person performing the method to assess various reference values. For example, the reference sample(s) may help in creating a mental image of the reference value by providing a "positive" reference value and/or a "negative" reference value.

One alternative for the quantification of HMGCR protein expression in a sample, such as the sample earlier obtained from the subject or the reference sample, is the determination of the fraction of cells in the sample that exhibit HMGCR protein expression over a certain level. The fraction may for example be: a "cellular fraction", wherein the HMGCR protein expression of the whole cells is taken into account; a "cytoplasmic fraction", wherein the HMGCR protein expression of only the cytoplasms of the cells is taken into account; or a "nuclear fraction", wherein the HMGCR protein expression of only the nuclei of the cells is taken into account. The cytoplasmic fraction may for example be classified as <2%, 2-25%, >25-75% or >75% immunoreactive cells of the relevant cell population. The "cytoplasmic fraction" corresponds to the percentage of relevant cells in a sample that exhibits a positive staining in the cytoplasm, wherein a medium or distinct and strong immunoreactivity in the cytoplasm is considered positive and no or faint immunoreactivity in the cytoplasm is considered negative. The person skilled in the art of pathology understands which cells that are relevant under the conditions present when performing the method and may determine a cytoplasmic fraction based on his general knowledge and the teachings of the present disclosure. The relevant cells may for example be tumor cells. Further, the skilled artisan understands how to perform corresponding measurements employing the "cellular fraction" or the "nuclear fraction".

Another alternative for the quantification of HMGCR protein expression in a sample, such as the sample earlier obtained from the subject or the reference sample, is the determination of the overall staining intensity of the sample. The intensity may for example be: a "cellular intensity", wherein the HMGCR protein expression of the whole cells is taken into account; a "cytoplasmic intensity", wherein the HMGCR protein expression of only the cytoplasms of the cells is taken into account, or a "nuclear intensity", wherein the HMGCR protein expression of only the nuclei of the cells is taken into account. Cytoplasmic intensity is subjectively evaluated in accordance with standards used in clinical histopathological diagnostics. Outcome of a cytoplasmic intensity determination may be classified as: absent=no overall immunoreactivity in the cytoplasms of relevant cells of the sample, weak=faint overall immunoreactivity in the cytoplasms of relevant cells of the sample, moderate=medium overall immunoreactivity in the cytoplasms of relevant cells of the sample, or strong=distinct and strong overall immunoreactivity in the cytoplasms of relevant cells of the sample. The person skilled in the art understands which cells that are relevant under the conditions present when performing the method and may determine a cytoplasmic intensity based on his general knowledge and the teachings of the present disclosure. The relevant cells may for example be tumor cells. The determination of cytoplasmic intensity may for example be performed as described below in the Examples, Section 4, definition of "cytoplasmic intensity". Further, the skilled artisan understands how to perform corresponding measurements employing the "cellular intensity" or the "nuclear intensity".

The inventors have found that the cytoplasmic expression of HMGCR protein is particularly relevant for making the treatment predictions. Thus, in embodiments of the methods of the above aspects, the reference value may be a cytoplasmic fraction, a cytoplasmic intensity or a combination thereof. Accordingly, the sample value may be a cytoplasmic fraction, a cytoplasmic intensity or a combination thereof.

Preferably, the sample value and the reference value are both the same type of value.

In embodiments of the methods of the above aspects, the criterion for the conclusion in step d) is a sample value for the cytoplasmic fraction of HMGCR protein positive cells, i.e., a "cytoplasmic fraction", which is higher than 0%, such as higher than 1%, such as higher than 2%, such as higher than 5%, such as higher than 10%, such as higher than 15%, such as higher than 20%, such as higher than 25%, such as higher than 30%, such as higher than 35%, such as higher than 40%, such as higher than 50%, such as higher than 60%, such as higher than 70%, such as higher than 75%, such as higher than 80%, such as higher than 90%.

In alternative or complementing embodiments of the methods of the above aspects, the reference value of step c) is a cytoplasmic fraction of 95% or lower, such as 90% or lower, such as 85% or lower, such as 80% or lower, such as 75% or lower, such as 70% or lower, such as 65% or lower, such as 60% or lower, such as 55% or lower, such as 50% or lower, such as 45% or lower, such as 40% or lower, such as 35% or lower, such as 30% or lower, such as 25% or lower, such as 20% or lower, such as 15% or lower, such as 10% or lower, such as 5% or lower, such as 2% or lower, such as 1% or lower, such as 0%.

The inventors have realized that low cut-off values, such as a value of 0, are particularly relevant for the treatment prediction. However, they have further noted that the examined tumor samples generally show either a cytoplasmic fraction of higher than 50% or a cytoplasmic fraction of 1% or lower, wherein the former group is associated with response to tamoxifen. Thus, if the reference value is a cytoplasmic fraction, it is preferably 50% or lower, such as 25% or lower, such as 20% or lower, such as 15% or lower. Most preferred is 10% or lower, such as 5% or lower, such as 2% or lower, such as 1% or lower, such as 0%.

Further, in embodiments of the methods of the above aspects, the criterion for the conclusion in step d) may be a sample value for staining intensity of a sample, i.e., a cytoplasmic intensity, which is higher than absent cytoplasmic intensity, such as higher than weak cytoplasmic intensity, such as higher than moderate cytoplasmic intensity. In alternative or complementing embodiments of the methods of the above aspects, the reference value of step c) may be a moderate cytoplasmic intensity of HMGCR protein expression or lower, such as a weak cytoplasmic intensity of HMGCR protein expression or lower, such as an absent cytoplasmic intensity.

In the examples section, the cut-off value "absent" cytoplasmic intensity is employed. Thus, if the reference value is a cytoplasmic intensity, it is preferably low, such as weak or lower. Most preferred is absent.

Further, in embodiments of the methods of the above aspects, the reference value may be constituted of two values, wherein the criterion for the conclusion in step d) is a sample value being higher than any one of these two values. An example of such a reference value is a cytoplasmic fraction of 25% or lower and a weak cytoplasmic intensity or lower.

Alternatively, in embodiments of the methods of the above aspects, the reference value may be a combination of a fraction value and an intensity value, such as a cytoplasmic fraction value and a cytoplasmic intensity value.

Also, in embodiments of the methods of the above aspects, the reference value may be a function of a cytoplasmic fraction value and a cytoplasmic intensity value. For example, such a function may be a staining score. The "staining score" is calculated as described in Examples, Section 3 and table 1 below. For example, the reference value may be a staining score of 2 or lower, such as 1 or lower, such as 0.

The person skilled in the art realizes that other reference values being an intensity value or a fraction value also fall within the scope of the present invention. Likewise, the person skilled in the art realizes that other combinations of fractions and intensities also fall within the scope of the present invention. Consequently, the reference value may involve two, and possibly even more, criteria.

In general, the selection of a cytoplasmic intensity value and/or a cytoplasmic fraction value as the reference value may depend on the staining procedure, e.g., on the employed anti-HMGCR antibody and on the staining reagents.

Guided by the present disclosure, a person skilled in the art, e.g., a pathologist, understands how to perform the evaluation yielding a fraction, such as a cellular, cytoplasmic or nuclear fraction, or an intensity, such as a cellular, cytoplasmic or nuclear intensity. For example, the skilled artisan may use a reference sample comprising a predetermined amount of HMGCR protein for establishing the appearance of a certain fraction or intensity.

However, a reference sample may not only be used for the provision of the actual reference value, but also for the provision of an example of a sample with an amount of HMGCR protein or HMGCR mRNA that is higher than the amount corresponding to the reference value. As an example, in histochemical staining, such as in immunohistochemical staining, the skilled artisan may use a reference sample for establishing the appearance of a stained sample having a high amount of HMGCR protein, e.g., a positive reference. Subsequently, the skilled artisan may assess the appearances of samples having lower amounts of HMGCR protein, such as the appearance of a sample with an amount of HMGCR protein corresponding to the reference value. In other words, the skilled artisan may use a reference sample to create a mental image of a reference value corresponding to an amount of HMGCR protein which is lower than that of the reference sample. Alternatively, or as a complement, in such assessments, the skilled artisan may use another reference sample having a low amount of HMGCR protein, or lacking detectable HMGCR protein, for establishing the appearance of such sample, e.g., as a "negative reference".

For example, if a reference value of 10% cytoplasmic fraction is used, two reference samples may be employed: a first reference sample having no detectable HMGCR protein, and thus corresponding to a cytoplasmic fraction of 0, which is lower than the reference value; and a second reference sample having an amount of HMGCR protein corresponding to a cytoplasmic fraction of 75% or higher, which is higher than the reference value.

Consequently, in the evaluation, the skilled artisan may use a reference sample for establishing the appearance of a sample with a high amount of HMGCR protein or HMGCR mRNA. Such reference sample may be a sample comprising tissue expressing a high amount of HMGCR protein or HMGCR mRNA, such as a sample comprising breast tumor tissue having a pre-established high expression of HMGCR protein or HMGCR mRNA.

Accordingly, the reference sample may provide an example of a strong cytoplasmic intensity (CI). With the knowledge of the appearance of a sample with strong CI, the skilled artisan may then divide samples into the CI categories absent, weak, moderate and strong. This division may be further assisted by a reference sample lacking detectable HMGCR protein (negative reference), i.e., a reference sample providing an absent cytoplasmic intensity. Also, the reference sample may provide an example of a sample with a cytoplasmic fraction (CF) of 75% or higher. With the knowledge of the appearance of a sample with more than 75% positive cells, the skilled artisan may then evaluate the cytoplasmic fraction of other samples having e.g., a lower percentage of positive cells. This division may be further assisted by a reference sample essentially lacking HMGCR protein (negative reference), i.e., a reference sample providing a low CF (e.g., <5%, such as <2%), or a CF of 0.

As mentioned above, cell lines expressing a controlled amount of HMGCR protein may be used as the reference, in particular as a positive reference.

On or more pictures may also be provided as the "reference sample". For example, such a picture may be of an example of a tumor tissue slide stained with a certain antibody during certain conditions that show a certain cellular intensity and/or fraction. The above discussion about the "reference sample" applies mutatis mutandis to pictures.

Further, the skilled person should recognize that the usefulness of the methods according to the above aspects is not limited to the quantification of any particular variant of the HMGCR protein or HMGCR mRNA present in the subject in question, as long as the protein is encoded by the relevant gene and presents the relevant pattern of expression.

As a non-limiting example, the HMGCR protein comprises, or consists of, a sequence selected from:

i) SEQ ID NO:1; and
ii) a sequence which is at least 85% identical to SEQ ID NO:1.

In some embodiments, sequence ii) above is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:1.

As another non-limiting example, the HMGCR protein comprises, or consists of, a sequence selected from:

i) SEQ ID NO:2; and
ii) a sequence which is at least 85% identical to SEQ ID NO:2.

In some embodiments, sequence ii) above is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:2.

The term "% identical", as used in the context of the present disclosure, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). The amino acid residues at each position are compared, and the percentage of positions in the query sequence that have identical correspondences in the target sequence is reported as % identical. Also, the target sequence determines the number of positions that are compared. Consequently, in the context of the present disclosure, a query sequence that is shorter than the target sequence can never be 100% identical to the target sequence. For example, a query sequence of 85 amino acids may at the most be 85% identical to a target sequence of 100 amino acids.

In embodiments of the methods of the aspects above, the HMGCR protein may be detected and/or quantified through the application to the sample of a detectable and/or quantifiable affinity ligand, which is capable of selective interaction with the HMGCR protein. The application of the affinity ligand is performed under conditions that enable binding of the affinity ligand to any HMGCR protein in the sample.

To concretize, in embodiments of the methods of the aspects above, step b) may comprise:

b1) applying to said sample a quantifiable affinity ligand capable of selective interaction with the HMGCR protein to be evaluated, said application being performed under conditions that enable binding of said affinity ligand to HMGCR protein present in said sample;

b2) removing non-bound affinity ligand; and b3) quantifying the affinity ligand remaining in association with said sample to evaluate said amount.

"Affinity ligand remaining in association with the sample" refers to affinity ligand which was not removed in step b2), e.g., the affinity ligand bound to the sample. Here, the binding may for example be the interaction between antibody and antigen.

However, in some embodiments, the removal of non-bound affinity ligand according to b2), e.g. the washing, may not be necessary. Thus, in some embodiments of the methods of the aspects above, step b) may comprise:

bI) applying to said sample a quantifiable affinity ligand capable of selective interaction with the HMGCR protein to be evaluated, said application being performed under conditions that enable binding of said affinity ligand to HMGCR protein present in said sample;

bII) quantifying the affinity bound to said sample to evaluate said amount.

It is regarded as within the capabilities of those of ordinary skill in the art to select or manufacture the proper affinity ligand and to select the proper format and conditions for detection and/or quantification, once the connection between HMGCR protein and treatment prediction for breast cancer is known through the teaching of the present disclosure. Nevertheless, examples of affinity ligands that may prove useful, as well as examples of formats and conditions for detection and/or quantification, are given below for the sake of illustration.

Thus, in embodiments of the present disclosure, the affinity ligand may be selected from the group consisting of antibodies, fragments thereof and derivatives thereof, i.e., affinity ligands based on an immunoglobulin scaffold. The antibodies and the fragments or derivatives thereof may be isolated and/or mono-specific. Antibodies comprise monoclonal and polyclonal antibodies of any origin, including murine, rabbit, human and other antibodies, as well as chimeric antibodies comprising sequences from different species, such as partly humanized antibodies, e.g., partly humanized mouse antibodies. Polyclonal antibodies are produced by immunization of animals with the antigen of choice. Monoclonal antibodies of defined specificity can be produced using the hybridoma technology developed by Köhler and Milstein (Köhler G and Milstein C (1976) Eur. J. Immunol. 6:511-519). The antibody fragments and derivatives of the present disclosure are capable of selective interaction with the same antigen (e.g. HMGCR protein) as the antibody they are fragments or derivatives of. Antibody fragments and derivatives comprise Fab fragments, consisting of the first constant domain of the heavy chain (CH1), the constant domain of the light chain (CL), the variable domain of the heavy chain (VH) and the variable domain of the light chain (VL) of an intact immunoglobulin protein; Fv fragments, consisting of the two variable antibody domains VH and VL (Skerra A and Plückthun A (1988) Science 240:1038-1041); single chain Fv fragments (scFv), consisting of the two VH and VL domains linked together by a flexible peptide linker (Bird R E and Walker B W (1991) Trends Biotechnol. 9:132-137); Bence Jones dimers (Stevens F J et al. (1991) Biochemistry 30:6803-6805); camelid heavy-chain dimers (Hamers-Casterman C et al., (1993) Nature 363:446-448) and single variable domains (Cai X and Garen A (1996) Proc. Natl. Acad. Sci. U.S.A. 93:6280-6285; Masat L et al. (1994) Proc. Natl. Acad. Sci. U.S.A. 91:893-896), and single domain scaffolds like e.g., the New Antigen Receptor (NAR) from the nurse shark (Dooley H et al. (2003) Mol. Immunol. 40:25-33) and minibodies based on a variable heavy domain (Skerra A and Plückthun A (1988) Science 240:1038-1041).

SEQ ID NO:1 was designed for immunizations, e.g., designed to lack transmembrane regions to ensure efficient expression in *E. coli*, and to lack any signal peptide, since those are cleaved off in the mature protein. Consequently, an antibody or fragment or derivative thereof according to the present disclosure may for example be one that is obtainable by a process comprising a step of immunizing an animal, such as a rabbit, with a protein whose amino acid sequence comprises, preferably consists of, the sequence SEQ ID NO:1. For example, the immunization process may comprise primary immunization with the protein in Freund's complete adjuvant. Also, the immunization process may further comprise boosting at least two times, in intervals of 2-6 weeks, with the protein in Freund's incomplete adjuvant. Processes for the production of antibodies or fragments or derivatives thereof against a given target are known in the art, and may be applied in connection with this aspect of the present disclosure.

In the context of the present disclosure, a "mono-specific antibody" is one of a population of polyclonal antibodies which has been affinity purified on its own antigen, thereby separating such mono-specific antibodies from other antiserum proteins and non-specific antibodies. This affinity purification results in antibodies that bind selectively to its antigen. In the case of the present disclosure, the polyclonal antisera are purified by a two-step immunoaffinity based protocol to obtain mono-specific antibodies selective for the target protein. Antibodies directed against generic affinity tags of antigen fragments are removed in a primary depletion step, using the immobilized tag protein as the capturing agent. Following the first depletion step, the serum is loaded on a second affinity column with the antigen as capturing agent, in order to enrich for antibodies specific for the antigen (see also Nilsson P et al. (2005) Proteomics 5:4327-4337).

Polyclonal and monoclonal antibodies, as well as their fragments and derivatives, represent the traditional choice of affinity ligands in applications requiring selective biomolecular recognition, such as in the detection and/or quantification of HMGCR protein according to the method aspects above. However, those of skill in the art know that, due to the increasing demand of high throughput generation of selective binding ligands and low cost production systems, new biomolecular diversity technologies have been developed during the last decade. This has enabled a generation of novel types of affinity ligands of both immunoglobulin as well as non-immunoglobulin origin that have proven equally useful as binding ligands in biomolecular recognition applications and can be used instead of, or together with, immunoglobulins.

The biomolecular diversity needed for selection of affinity ligands may be generated by combinatorial engineering of one of a plurality of possible scaffold molecules, and specific and/or selective affinity ligands are then selected using a suitable selection platform. The scaffold molecule may be of immunoglobulin protein origin (Bradbury A R and Marks J D (2004) J. Immunol. Meths. 290:29-49), of non-immunoglobulin protein origin (Nygren P A and Skerra A (2004) J. Immunol. Meths. 290:3-28), or of an oligonucleotide origin (Gold L et al. (1995) Annu. Rev. Biochem. 64:763-797).

A large number of non-immunoglobulin protein scaffolds have been used as supporting structures in development of novel binding proteins. Non-limiting examples of such structures, useful for generating affinity ligands against HMGCR protein for use according to the present disclosure, are staphylococcal protein A and domains thereof and derivatives of these domains, such as protein Z (Nord K et al. (1997) Nat. Biotechnol. 15:772-777); lipocalins (Beste G et al. (1999) Proc. Natl. Acad. Sci. U.S.A. 96:1898-1903); ankyrin repeat domains (Binz H K et al. (2003) J. Mol. Biol. 332:489-503); cellulose binding domains (CBD) (Smith G P et al. (1998) J. Mol. Biol. 277:317-332; Lehtiö J et al. (2000) Proteins 41:316-322); γ crystallines (Fiedler U and Rudolph R, WO01/04144); green fluorescent protein (GFP) (Peelle B et al. (2001) Chem. Biol. 8:521-534); human cytotoxic T lymphocyte-associated antigen 4 (CTLA-4) (Hufton S E et al. (2000) FEBS Lett. 475:225-231; Irving R A et al. (2001) J. Immunol. Meth. 248:31-45); protease inhibitors, such as Knottin proteins (Wentzel A et al. (2001) J. Bacteriol. 183:7273-7284; Baggio R et al. (2002) J. Mol. Recognit. 15:126-134) and Kunitz domains (Roberts B L et al. (1992) Gene 121:9-15; Dennis M S and Lazarus R A (1994) J. Biol. Chem. 269: 22137-22144); PDZ domains (Schneider S et al. (1999) Nat. Biotechnol. 17:170-175); peptide aptamers, such as thioredoxin (Lu Z et al. (1995) Biotechnology 13:366-372; Klevenz B et al., (2002) Cell. Mol. Life Sci. 59:1993-1998); staphylococcal nuclease (Norman T C et al. (1999) Science 285:

591-595); tendamistats (McConell S J and Hoess R H (1995) J. Mol. Biol. 250:460-479; Li R et al. (2003) Protein Eng. 16:65-72); trinectins based on the fibronectin type III domain (Koide A et al. (1998) J. Mol. Biol. 284:1141-1151; Xu L et al. (2002) Chem. Biol. 9:933-942); and zinc fingers (Bianchi E et al. (1995) J. Mol. Biol. 247:154-160; Klug A (1999) J. Mol. Biol. 293:215-218; Segal D J et al. (2003) Biochemistry 42:2137-2148).

The above-mentioned examples of non-immunoglobulin protein scaffolds include scaffold proteins presenting a single randomized loop used for the generation of novel binding specificities, protein scaffolds with a rigid secondary structure where side chains protruding from the protein surface are randomized for the generation of novel binding specificities, and scaffolds exhibiting a non-contiguous hyper-variable loop region used for the generation of novel binding specificities.

In addition to non-immunoglobulin proteins, oligonucleotides may also be used as affinity ligands. Single stranded nucleic acids, called aptamers or decoys, fold into well-defined three-dimensional structures and bind to their target with high affinity and specificity. (Ellington A D and Szostak J W (1990) Nature 346:818-822; Brody E N and Gold L (2000) J. Biotechnol. 74:5-13; Mayer G and Jenne A (2004) BioDrugs 18:351-359). The oligonucleotide ligands can be either RNA or DNA and can bind to a wide range of target molecule classes.

For selection of the desired affinity ligand from a pool of variants of any of the scaffold structures mentioned above, a number of selection platforms are available for the isolation of a specific novel ligand against a target protein of choice. Selection platforms include, but are not limited to, phage display (Smith G P (1985) Science 228:1315-1317), ribosome display (Hanes J and Plückthun A (1997) Proc. Natl. Acad. Sci. U.S.A. 94:4937-4942), yeast two-hybrid system (Fields S and Song O (1989) Nature 340:245-246), yeast display (Gai S A and Wittrup K D (2007) Curr Opin Struct Biol 17:467-473), mRNA display (Roberts R W and Szostak J W (1997) Proc. Natl. Acad. Sci. U.S.A. 94:12297-12302), bacterial display (Daugherty P S (2007) Curr Opin Struct Biol 17:474-480, Kronqvist N at al. (2008) Protein Eng Des Sel 1-9, Harvey B R et al. (2004) PNAS 101(25):913-9198), microbead display (Nord O et al. (2003) J Biotechnol 106:1-13, WO01/05808), SELEX (System Evolution of Ligands by Exponential Enrichment) (Tuerk C and Gold L (1990) Science 249:505-510) and protein fragment complementation assays (PCA) (Remy I and Michnick S W (1999) Proc. Natl. Acad. Sci. U.S.A. 96:5394-5399).

Thus, in embodiments of the present disclosure, the affinity ligand may be a non-immunoglobulin affinity ligand derived from any of the protein scaffolds listed above, or an oligonucleotide molecule.

The HMGCR protein SEQ ID NO:1 was designed to consist of a unique sequence with low homology with other human proteins and to minimize cross reactivity of generated affinity reagents. Consequently, in embodiments of the present disclosure, the affinity ligand may be capable of selective interaction with a polypeptide consisting of the sequence SEQ ID NO:1.

In Examples below, an antibody binding to an HMGCR epitope having the sequence SEQ ID NO:4 is employed. SEQ ID NO:4 refers to the amino acid sequence CKDNPGENAR-QLAR (i.e. amino acids 827-840 of EnsEMBL entry no. ENSP00000287936). This antibody resulted in strong staining. Consequently, in further embodiments of the present disclosure, the quantifiable affinity ligand may be capable of selective interaction with an HMGCR protein comprising, or consisting of, the sequence SEQ ID NO:4.

In some embodiments of present disclosure, an affinity ligand capable of selective interaction with the HMGCR protein is detectable and/or quantifiable. The detection and/or quantification of such an affinity ligand may be accomplished in any way known to the skilled person for detection and/or quantification of binding reagents in assays based on biological interactions. Thus, any affinity ligand, as described above, may be used quantitatively or qualitatively to detect the presence of the HMGCR protein. These "primary" affinity ligands may be labeled themselves with various markers or may in turn be detected by secondary, labeled affinity ligands to allow detection, visualization and/or quantification. This can be accomplished using any one or more of a multitude of labels, which can be conjugated to the affinity ligand capable of interaction with HMGCR protein or to any secondary affinity ligand, using any one or more of a multitude of techniques known to the skilled person, and not as such involving any undue experimentation.

Non-limiting examples of labels that can be conjugated to primary and/or secondary affinity ligands include fluorescent dyes or metals (e.g., fluorescein, rhodamine, phycoerythrin, fluorescamine), chromophoric dyes (e.g., rhodopsin), chemiluminescent compounds (e.g., luminal, imidazole) and bioluminescent proteins (e.g., luciferin, luciferase), haptens (e.g., biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g., horseradish peroxidase, alkaline phosphatase, beta-lactamase), radioisotopes (e.g., $^3$H, $^{14}$C, $^{32}$P, $^{35}$S or $^{125}$I) and particles (e.g., gold). In the context of the present disclosure, "particles" refer to particles, such as metal particles, suitable for labeling of molecules. Further, the affinity ligands may also be labeled with fluorescent semiconductor nanocrystals (quantum dots). Quantum dots have superior quantum yield and are more photostable compared to organic fluorophores and are therefore more easily detected (Chan et al. (2002) *Curr Opi Biotech.* 13: 40-46). The different types of labels can be conjugated to an affinity ligand using various chemistries, e.g., the amine reaction or the thiol reaction. However, other reactive groups than amines and thiols can be used, e.g., aldehydes, carboxylic acids and glutamine.

The method aspects above may be put to use in any of several known formats and set-ups, of which a non-limiting selection is discussed below.

In a set-up based on histology, the detection, localization and/or quantification of a labeled affinity ligand bound to its HMGCR protein target may involve visualizing techniques, such as light microscopy or immunofluoresence microscopy. Other methods may involve the detection via flow cytometry or luminometry.

A biological sample, such as a tumor tissue sample (biopsy), for example from breast tissue, which has'been removed from the subject may be used for detection and/or quantification of HMGCR protein or HMGCR mRNA. The biological sample, such as the biopsy, may be an earlier obtained sample. If using an earlier obtained sample in a method, no steps of the method are practiced on the human or animal body. The affinity ligand may be applied to the biological sample for detection and/or quantification of the HMGCR protein. This procedure enables not only detection of HMGCR protein, but may in addition show the distribution and relative level of expression thereof.

The method of visualization of labels on the affinity ligand may include, but is not restricted to, fluorometric, luminometric and/or enzymatic techniques. Fluorescence is detected and/or quantified by exposing fluorescent labels to light of a specific wavelength and thereafter detecting and/or quantifying the emitted light in a specific wavelength region. The presence of a luminescently tagged affinity ligand may be detected and/or quantified by luminescence developed during a chemical reaction. Detection of an enzymatic reaction is due to a color shift in the sample arising from chemical reaction. Those of skill in the art are aware that a variety of different protocols can be modified in order for proper detection and/or quantification.

In embodiments of the methods of the above aspects, a biological sample may be immobilized onto a solid phase support or carrier, such as nitrocellulose or any other solid support matrix capable of immobilizing HMGCR protein present in the biological sample applied to it. Some well-known solid state support materials useful in the present invention include glass, carbohydrate (e.g., Sepharose), nylon, plastic, wool, polystyrene, polyethene, polypropylene, dextran, amylase, films, resins, cellulose, polyacrylamide, agarose, alumina, gabbros and magnetite. After immobilization of the biological sample; Primary affinity ligand specific to HMGCR protein may be applied, e.g., as described in Examples, Sections 3, 4 or 5, of the present disclosure. If the primary affinity ligand is not labeled in itself, the supporting matrix may be washed with one or more appropriate buffers known in the art, followed by exposure to a secondary labeled affinity ligand and washed once again with buffers to remove unbound affinity ligands. Thereafter, selective affinity ligands may be detected and/or quantified with conventional methods. The binding properties for an affinity ligand may vary from one solid state support to the other, but those skilled in the art should be able to determine operative and optimal assay conditions for each determination by routine experimentation.

Consequently, in embodiments of the methods of the above aspects, the quantifiable affinity ligand of b1) may be detected using a secondary affinity ligand capable of recognizing the quantifiable affinity ligand. The quantification of b3) may thus be carried out by means of a secondary affinity ligand with affinity for the quantifiable affinity ligand. As an example, the secondary affinity ligand may be an antibody or a fragment or a derivative thereof.

As an example, one available method for detection and/or quantification of the HMGCR protein is by linking the affinity ligand to an enzyme that can then later be detected and/or quantified in an enzyme immunoassay (such as an EIA or ELISA). Such techniques are well established, and their realization does not present any undue difficulties to the skilled person. In such methods, the biological sample is brought into contact with a solid material or with a solid material conjugated to an affinity ligand against the HMGCR protein, which is then detected and/or quantified with an enzymatically labeled secondary affinity ligand. Following this, an appropriate substrate is brought to react in appropriate buffers with the enzymatic label to produce a chemical moiety, which for example is detected and/or quantified using a spectrophotometer, fluorometer, luminometer or by visual means.

As stated above, primary and any secondary affinity ligands can be labeled with radioisotopes to enable detection and/or quantification. Non-limiting examples of appropriate radiolabels in the present disclosure are $^3$H, $^{14}$C, $^{32}$P, $^{35}$S or $^{125}$I. The specific activity of the labeled affinity ligand is dependent upon the half-life of the radiolabel, isotopic purity, and how the label has been incorporated into the affinity ligand. Affinity ligands are preferably labeled using well-known techniques (Wensel T G and Meares C F (1983) in: *Radioimmunoimaging and Radioimmunotherapy* (Burchiel S W and Rhodes B A eds.) Elsevier, New York, pp 185-196). A thus radiolabeled affinity ligand can be used to visualize HMGCR protein by detection of radioactivity in vivo or in vitro. Radionuclear scanning with e.g., gamma camera, magnetic resonance spectroscopy or emission tomography function for detection in vivo and in vitro, while gamma/beta counters, scintillation counters and radiographies are also used in vitro.

Methods for detecting and quantifying biomarkers on the mRNA level are well known within the art.

According to one such method, total cellular RNA is purified from cells by homogenization in the presence of nucleic acid extraction buffer, followed by centrifugation. Nucleic acids is then precipitated, in order to remove DNA by treatment with DNase and precipitation. The RNA molecules are then separated by gel electrophoresis on agarose gels according to standard techniques, and transferred to nitrocellulose filters by, e.g., the so-called "Northern" blotting technique. The RNA is then immobilized on the filters by heating. Detection and quantification of specific RNA is accomplished using appropriately labeled DNA or RNA probes complementary to the RNA in question. See, for example, Molecular Cloning: A Laboratory Manual (Sambrook J. et al., (1989) 2nd edition, Cold Spring Harbor Laboratory Press). Methods for the preparation of labeled DNA and RNA probes, and the conditions for hybridization thereof to target nucleotide sequences, are described in Molecular Cloning: A Laboratory Manual (Sambrook J. et al., (1989) 2nd edition, Cold Spring Harbor Laboratory Press). For example, the nucleic acid probe may be labeled with, e.g., a radionuclide such as $^3$H, $^{32}$P, $^{33}$P, $^{14}$C, or $^{35}$S; a heavy metal; or a ligand capable of functioning as a specific binding pair member for a labeled ligand (e.g., biotin, avidin, or an antibody), a fluorescent molecule, a chemiluminescent molecule, an enzyme, or the like.

Probes may be labeled to high specific activity by either the nick translation method (Rigby et al., (1977) J. Mol Biol, 113: 237-251), or by the random priming method (Fienberg, (1983) Anal. Biochem., 132: 6-13). The latter can be a method for synthesizing $^{32}$P-labeled probes of high specific activity from RNA templates. For example, by replacing preexisting nucleotides with highly radioactive nucleotides according to the nick translation method, it is possible to prepare $^{32}$P-labeled nucleic acid probes with a specific activity well in excess of 10 cpm/microgram. Autoradiographic detection of hybridization then can be performed by exposing hybridized filters to photographic film. Densitometric scanning of the photographic films exposed by the hybridized filters provides an accurate measurement of biomarker levels. Using another approach, biomarker levels can be quantified by computerized imaging systems, such as the Molecular Dynamics 400-B 2D Phosphorimager (Amersham Biosciences, Piscataway, N.J., USA).

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA blotting hybridization techniques, determining the levels of RNA transcript may be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects.

The relative number of RNA transcripts in cells can also be determined by reverse transcription of RNA transcripts, followed by amplification of the reverse-transcribed transcripts by polymerase chain reaction (RT-PCR). The levels of RNA transcripts can be quantified in comparison with an internal standard, for example, the level of mRNA from a standard gene present in the same sample. The person skilled in the art is capable of selecting suitable genes for use as an internal standard. The methods for quantitative RT-PCR and variations thereof are within the skill in the art.

Any suitable primers can be used for the quantitative RT-PCR. Preferably, the primers are specific to HMGCR. It is within the skill in the art to generate primers specific to HMGCR (e.g. starting from SEQ ID NO:3). Primers can be of any suitable length, but are preferably between 19 and 23 (e.g., 19, 20, 21, 22, or 23) nucleotides. Ideally, amplicon length should be 50 to 150 (up to 250 may be necessary but then optimization of the thermal cycling protocol and reaction components may be necessary) bases for optimal PCR efficiency. Designing primers that generate a very long amplicon may lead to poor amplification efficiency. Information about primer design and optimal amplicon size may for example be found at www.ambion.com.

In some instances, it may be desirable to use microchip technology to detect biomarker expression. The microchip can be fabricated by techniques known in the art. For example, probe oligonucleotides of an appropriate length, e.g., 40 nucleotides, are 5'-amine modified at position C6 and printed using commercially available microarray systems, e.g., the GENEMACHINE OmniGrid 100 Microarrayer and Amersham CODELINK activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6 times SSPE/30% formamide at 25° C. for 18 hours, followed by washing in 0.75 times TNT at 37° C. for 40 minutes. At positions on the array, where the immobilized probe DNA recognizes a complementary target cDNA in the sample, hybridization occurs. The labeled target cDNA marks the exact position on the array where binding occurs, thereby allowing automatic detection and quantification. The output consists of a list of hybridization events, which indicate the relative abundance of specific cDNA sequences, and therefore the relative abundance of the corresponding complementary biomarker, in the subject sample. According to one embodiment, the labeled cDNA oligomer is a biotin-labeled cDNA prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding biomarker in the subject sample.

The use of the array has one or more advantages for mRNA expression detection. First, the global expression of several to thousands of genes can be identified in a single sample at one time. Second, through careful design of the oligonucleotide probes, the expression of both mature and precursor molecules can be identified. Third, in comparison with Northern blot analysis, the chip requires a small amount of RNA.

The HMGCR mRNA (as well as the HMGCR protein) may for example be extracted from formalin-fixed, paraffin-embedded tumor tissue. Accordingly, the sample of the methods of the present disclosure may be formalin-fixed and/or paraffin-embedded breast tumor tissue.

The inventors have realized that HMGCR mRNA analysis of the present disclosure may be incorporated in an oncotypeDX® assay, such as the oncotypeDX® breast cancer assay, which is designed to support individualized treatment planning and employs RT-PCR to analyze the expression of several genes.

As explained herein, HMGCR is a relevant biomarker for breast cancer subjects. Thus, as a configuration of the present disclosure, there is provided a method in which, in a sample from a subject having or suspected of having a breast cancer, the levels of expression of the HMGCR gene and at least one of the following genes are analyzed:

KI-67, STK15, Survivin, Cyclin B1, MYBL2, Stromelysin 3, Cathepsin L2, GRB7, HER2, ER, PR, Bcl2, SCUBE2, Beta-actin, GAPDH, RPLPO, GUS, TFRC, GSTM1, CD68 and BAG1.

All these genes are included in the gene panel of the OncotypeDX® breast cancer assay.

In an embodiment, the other gene of the configuration is selected from the group consisting of ER, PR, Bcl2 and SCUBE2, which are "Estrogen genes".

As a third aspect of the present disclosure, there is provided a kit for carrying out a method according to the above aspects, which comprises:

a) a quantifiable affinity ligand capable of selective interaction with an HMGCR protein; and b) reagents necessary for quantifying the amount of the affinity ligand.

Various components of the kit according to the third aspect may be selected and specified as described above in connection with the method aspects of the present disclosure.

Thus, the kit according to the present disclosure comprises an affinity ligand against an HMGCR protein, as well as other means that help to quantify the specific and/or selective affinity ligand after it has bound specifically and/or selectively to the HMGCR protein. For example, the kit may contain a secondary affinity ligand for detecting and/or quantifying a complex formed by the HMGCR protein and the affinity ligand capable of selective interaction with the HMGCR protein. The kit may also contain various auxiliary substances other than affinity ligands, to enable the kit to be used easily and efficiently. Examples of auxiliary substances include solvents for dissolving or reconstituting lyophilized protein components of the kit, wash buffers, substrates for measuring enzyme activity in cases where an enzyme is used as a label, target retrieval solution to enhance the accessibility to antigens in cases where paraffin or formalin-fixed tissue samples are used, and substances such as reaction arresters, e.g., endogenous enzyme block solution to decrease the background staining and/or counterstaining solution to increase staining contrast, that are commonly used in immunoassay reagent kits.

In embodiments of the kit aspect, the affinity ligand may be selected as described above in connection with the method aspects.

Further, in accordance with what is described above in connection with the method aspects, the detectable affinity ligand may in embodiments of the kit aspect comprise a label selected from the group consisting of fluorescent dyes and metals, chromophoric dyes, chemiluminescent compounds and bioluminescent proteins, enzymes, radioisotopes, particles and quantum dots. Alternatively, the reagents necessary for quantifying the amount of the affinity ligand comprise a secondary affinity ligand capable of recognizing the quantifiable affinity ligand. As an example, the secondary affinity ligand capable of recognizing the quantifiable affinity ligand comprises a label selected from the group consisting of fluorescent dyes or metals, chromophoric dyes, chemiluminescent compounds and bioluminescent proteins, enzymes, radioisotopes, particles and quantum dots.

The kit according to the kit aspect may also advantageously comprise a reference sample for provision of, or yielding, the reference value to be used for comparison with the sample value. For example, the reference may sample comprise a predetermined amount of HMGCR protein. Such a reference sample may for example be constituted by a tissue sample having the predetermined amount of HMGCR protein. The tissue reference sample may then be used by the person of skill in the art in the determination of the HMGCR expression status in the sample being studied, by manual, such as ocular, or automated comparison of expression levels in the reference tissue sample and the subject sample. As another example, the reference sample may comprise cell lines, such as cancer cell lines, expressing a predetermined, or controlled, amount of HMGCR protein. The person skilled in the art understands how to provide such cell lines, for example guided by the disclosure of Rhodes et al. (2006) The biomedical scientist, p 515-520. As an example, the cell lines may be formalin fixed. Also, such formalin fixed cell lines may be paraffin embedded.

The wording "reference sample for provision of the reference value" is to be interpreted broadly in the context of the present disclosure. The reference sample may comprise an amount of HMGCR protein actually corresponding to the reference value, but it may also comprise an amount of HMGCR protein corresponding to a value being higher than the reference value. In the latter case, the "high" value may be used by a person performing the method as an upper reference (positive reference) for assessing, e.g., the appearance of, a reference value which is lower than the "high" value. The person skilled in the art of immunohistochemistry understands how to do such an assessment. Further, as an alternative or a complementing example, the skilled person may use another reference sample comprising a low amount of HMGCR protein for provision of a "low" value in such an assessment, e.g., as a negative reference. This is further discussed above in connection with the method aspects.

Consequently, in embodiments of the kit aspect, the reference sample may comprise an amount of HMGCR protein corresponding to the reference value. As an example, the reference sample may comprise an amount of HMGCR protein corresponding to a cytoplasmic fraction of 95% or lower, such as 90% or lower, such as 85% or lower, such as 80% or lower, such as 75% or lower, such as 70% or lower, such as 65% or lower, such as 60% or lower, such as 55% or lower, such as 50% or lower, such as 45% or lower, such as 40% or lower, such as 35% or lower, such as 30% or lower, such as 25% or lower, such as 20% or lower, such as 15% or lower, such as 10% or lower, such as 5% or lower, such as 2% or lower, such as 1% or lower, such as 0%.

As mentioned above, the inventors have realized that low cut-off values, such as a value of 0, are particularly relevant for the treatment prediction. However, they have further noted that the examined tumor samples generally show either a cytoplasmic fraction of higher than 50% or a cytoplasmic fraction of 1% or lower, wherein the former group is associated with response to tamoxifen.

Thus, in preferred embodiments, the reference sample may comprise an amount of HMGCR protein corresponding to a cytoplasmic fraction of 50% or lower, such as 25% or lower, such as 20% or lower, such as 15% or lower, such as 10% or lower, such as 5% or lower, such as 2% or lower, such as 1% or lower, such as 0%.

Alternatively, or as a complement, the reference sample may comprise an amount of HMGCR protein corresponding to a moderate cytoplasmic intensity of HMGCR protein expression or lower, such as a weak cytoplasmic intensity of HMGCR protein expression or lower. As shown in the attached figures, a low cytoplasmic intensity, such as an absent cytoplasmic intensity, is a relevant cut-off. Thus, in an embodiment, the reference sample may comprise an amount of HMGCR protein corresponding to weak cytoplasmic intensity or lower, such as an absent cytoplasmic intensity.

Further, the reference sample may comprise an amount of HMGCR protein corresponding to a staining score of 0, 1 or 2, preferably 0.

The provision of cytoplasmic fraction values or cytoplasmic intensity values is discussed above in connection with the method aspects.

Further, in alternative or complementing embodiments of the kit aspect, the kit may comprise a reference sample comprising an amount of HMGCR protein corresponding to a value being higher than the reference value. In these embodiments, the reference sample may for example comprise an amount of HMGCR protein corresponding to a cytoplasmic fraction of 75% or higher and/or a strong cytoplasmic intensity of nuclear expression.

In other alternative or complementing embodiments of the kit aspect, the kit may comprise a reference sample comprising an amount of HMGCR protein corresponding to a value being lower than or equal to the reference value, e.g., an absent cytoplasmic intensity and/or a cytoplasmic fraction of ≤1% HMGCR protein positive cells, such as 0% HMGCR protein positive cells.

The kit may thus comprise: a reference sample comprising an amount of HMGCR protein corresponding to a predetermined reference value; a reference sample comprising an amount of HMGCR protein corresponding to a value being higher than a predetermined reference value; and/or a reference sample comprising an amount of HMGCR protein corresponding to a value being lower than or equal to a predetermined reference value.

Consequently, embodiments of the kit may comprise: a first reference sample comprising an amount of HMGCR protein being higher than a predetermined reference value; and a second reference sample comprising an amount of HMGCR protein being lower than or equal to the predetermined reference value.

In embodiments of the kit aspect, the reference sample may be a tissue sample, such as a tissue sample adapted to ocular or microscopic evaluation. As an example, the tissue reference sample may be fixated in paraffin or buffered formalin and/or histo-processed to μm-thin sections that are mounted on microscopic glass-slides. The tissue reference sample may be further adapted to staining with affinity ligands, such as antibodies, against an HMGCR protein.

Consequently, in embodiments of the kit aspect, the reference sample may be adapted to directly, or indirectly, provide any relevant reference value, such as any one of the reference values discussed above.

Accordingly, further embodiments of the reference sample of the kit aspect are discussed above in connection with the reference values and reference samples of the method aspects.

As further discussed above, the combination of a level of HMGCR protein expression and hormone receptor status may provide information relevant for drawing conclusions regarding a treatment prediction breast cancer subject.

For the reasons described above, the "breast cancer" of the third aspect and the further aspects described below may be a hormone receptor negative breast cancer, such as an ER− or PR− breast cancer, an ER− breast cancer, a PR− breast cancer, or an ER− and PR− breast cancer. For example, the breast cancer may be previously diagnosed as hormone receptor negative.

Thus, the kit may also include means for establishing the hormone receptor status of a subject.

Accordingly, in embodiments of the kit aspect, the kit may further comprise:

a') a quantifiable affinity ligand capable of selective interaction with the estrogen receptor and b') reagents necessary for quantifying the amount of such affinity ligand; and/or a") a quantifiable affinity ligand capable of selective interaction with the progesterone receptor and b") reagents necessary for quantifying the amount of such affinity ligand.

The quantifiable affinity ligands of a') and a") are provided for the determination of the ER status and PR status, respectively.

The reagents of b), b') and b"), may be the same or different.

Quantifiable affinity ligands appropriate for steps a') and a"), respectively, are well known to the skilled person and commercially available.

Consequently, the kit may include means for provision of the hormonal status information necessary for drawing conclusions according to some embodiments of the method aspects of the present disclosure.

HMGCR may also be detected on the mRNA level. Such detection may for example be an in situ mRNA analysis or a quantitative RT-PCR mRNA analysis. Further, the mRNA of a sample may be copied into cDNA to increase stability prior to detection.

Thus, as a configuration of the third aspect, there is provided a kit comprising at least one probe or primer for detection and/or quantification of HMGCR mRNA or HMGCR cDNA.

As described herein, a more refined treatment prediction may be obtained if the levels of both HMGCR and ER or PR in the sample are analyzed. Thus, in an embodiment, the kit of the configuration of the third aspect may further comprise:

a probe or primer for detection and/or quantification of ER mRNA or ER cDNA and/or a probe or primer for detection and/or quantification of PR mRNA or PR cDNA.

A probe or primer according to the configuration of the third aspect may for example be a single or double stranded oligonucleotide that is complementary to a part of the mRNA or cDNA in question. The HMGCR cDNA is represented by SEQ ID NO:3. If the probe is double stranded, it is denaturated prior to detection/hybridization to become single stranded, e.g. by means of heating.

The length of the probe(s) or primer(s) may for example be at least 5, such as at least 10, such as at least 15, such as at least 20, such as at least 25, such as at least 30, such as at least 50, such as at least 75, such as at least 100, such as at least 150 consecutive nucleotides.

A primer is normally shorter than a probe.

The kit may comprise further auxiliary products. Examples of such products are described above in connection with the discussion about mRNA analysis. Thus, the kit of the configuration of the third aspect may for example comprise one or more auxilliary products selected from the group consisting of a pre-treatment solution (for preparing the sample), a proteolytic enzyme such as pepsin, a second probe (to be used as a reference), a buffer such as a wash buffer and a fluorescence mounting medium (if fluorescent labels are used). The probes of the configuration of the third aspect may be labeled or conjugated to other chemical moieties. This is also exemplified above in connection with the discussion about mRNA analysis.

Further, the probes of the configuration of the third aspect may for example be arranged on a solid phase, optionally together with probes for other targets. Examples of such other probes are those capable of detecting the mRNA of KI-67, STK15, Survivin, Cyclin B1, MYBL2, Stromelysin 3, Cathepsin L2, GRB7, HER2, Bcl2, SCUBE2, Beta-actin, GAPDH, RPLPO, GUS, TFRC, GSTM1, CD68 and BAG1. The analysis of HMGCR may for example be included in a MammaPrint® test. Accordingly, the HMGCR probe may be arranged on a solid phase together with probe(s) for one or more of the other genes of the MammaPrint® test.

Following the findings presented above, the inventors have realized several uses for the HMGCR protein or HMGCR mRNA.

Thus, as a first configuration of a fourth aspect of the present disclosure, there is provided a use of a HMGCR protein or HMGCR mRNA as an endocrine treatment indicating marker for a mammalian subject having a breast cancer.

In the context of the present disclosure, "endocrine treatment indicating marker" refers to a something material which presence indicates a suitability of an endocrine treatment. The marker may thus be a biomarker, such as a human protein.

As a second configuration of the fourth aspect, there is provided a use of a HMGCR protein, or an antigenically active fragment thereof, for the production, selection or purification of an endocrine treatment indicating agent for a mammalian subject having a breast cancer.

In the context of the present disclosure, "endocrine treatment indicating agent" refers to an agent having at least one property being valuable in an establishment of a treatment prediction for an endocrine treatment, e.g., of a mammalian subject having a breast cancer. For example, the indicating agent may be capable of selective interaction with the indicating marker.

The endocrine treatment indicating agent may be an affinity ligand capable of selective interaction with the HMGCR protein, or an antigenically active fragment thereof. Examples of such affinity ligands are discussed above in connection with the method aspects.

Guided by the teachings of the present disclosure, the person skilled in the art understands how to use HMGCR protein in the production, selection or purification of the endocrine treatment indicating agent. For example, the use may comprise affinity purification on a solid support onto which the HMGCR protein has been immobilized. The solid support may for example be arranged in a column. Further, the use may comprise selection of affinity ligands having specificity for the HMGCR protein using a solid support onto which the polypeptide has been immobilized. Such solid support may be well plates (such as 96 well plates), magnetic beads, agarose beads or sepharose beads. Further, the use may comprise analysis of affinity ligands on a soluble matrix, for example using a dextran matrix, or use in a surface plasmon resonance instrument, such as a Biacore™ instrument, wherein the analysis may for example comprise monitoring the affinity for the immobilized HMGCR protein of a number of potential affinity ligands.

Also, for the production of the endocrine treatment indicating agent or the treatment predictive agent, the HMGCR protein may be used in an immunization of an animal.

Such use may be involved in a method comprising the steps:
i) immunizing an animal using the HMGCR protein as the antigen;
ii) obtaining serum comprising the endocrine treatment indicating agent from the immunized animal; and, optionally,
iii) isolating the endocrine treatment indicating agent from the serum.

Alternatively the steps following the first step may be:
ii') obtaining cells from the immunized animal, which cells comprise DNA encoding the endocrine treatment indicating agent,
iii') fusing the cells with myeloma cells to obtain at least one clone, and
iv') obtaining the endocrine treatment indicating agent expressed by the clone.

In embodiments of the fourth aspect, the amino acid sequence of the HMGCR protein may comprise a sequence selected from:
i) SEQ ID NO:1; and
ii) a sequence which is at least 85% identical to SEQ ID NO:1.

In some embodiments, sequence ii) is at least 90% identical, at least 91% identical, at least 92% identical, at least 93% identical, at least 94% identical, at least 95% identical, at least 96% identical, at least 97 identical, at least 98% identical or at least 99% identical to SEQ ID NO:1.

Further, in embodiments of the fourth aspect the amino acid sequence of the HMGCR protein may comprise a sequence selected from:
i) SEQ ID NO:2; and
ii) a sequence which is at least 85% identical to SEQ ID NO:2.

In some embodiments, sequence ii) is at least 90% identical, at least 91% identical, at least 92% identical, at least 93% identical, at least 94 identical, at least 95% identical, at least 96% identical, at least 97% identical, at least 98% identical or at least 99% identical to SEQ ID NO:2.

As a fifth aspect of the present disclosure, there is provided an affinity ligand capable of selective interaction with an HMGCR protein.

Examples of such affinity ligands are discussed above in connection with the method aspects.

The affinity ligand may be used for in vivo diagnosis, such as in vivo imaging.

Thus, as a first configuration of the fifth aspect, there is provided an affinity ligand capable of selective interaction with an HMGCR protein, for in vivo use as an endocrine treatment indicating agent in a mammalian subject having a breast cancer.

Accordingly, in an embodiment, the affinity ligand may be for use in an in vivo method for establishing a prediction of an outcome of an endocrine treatment, such as a tamoxifen treatment, of a mammalian subject having a breast cancer, such as an ER negative breast cancer. The establishment of a prediction of the outcome of an endocrine treatment of a subject may for example be a determination of whether the subject is likely to benefit from the endocrine treatment. In such embodiments the affinity ligand may for example be labeled for enabling imaging, i.e. labeled with a detectable label. Appropriate labels for labeling affinity ligands such as antibodies are well known to the skilled person. The in vivo method for establishing a treatment prediction for a mammalian subject having a breast cancer may for example reveal HMGCR protein expression in a tumor in vivo, which in turn may form the basis of a treatment decision. Various in vivo methods, labels and detection techniques that may be used in the context of this embodiment are further discussed above.

In a similar configuration of the fifth aspect, there is provided an affinity ligand, capable of selective interaction with an HMGCR protein, for in vivo evaluation an amount of HMGCR protein in a subject having a breast cancer. For example, the level of HMGCR expression in the breast cancer tumor may be evaluated.

As a sixth aspect of the present disclosure, there is provided a use of an affinity ligand according to the fifth aspect as an endocrine treatment indicating agent for a mammalian subject having a breast cancer. Consequently, the affinity ligand may be used for indicating whether a mammalian subject having a breast cancer would benefit from an endocrine treatment. Such use may for example be performed in vitro, e.g., involving the determination of the amount of HMGCR in at least part of a sample earlier obtained from the subject.

In the present disclosure, endocrine treatment, in particular SERM treatment, such as tamoxifen treatment, is shown to be particularly beneficial for those subjects who are HMGCR positive (see Examples, section 4 and the figures). The breast cancer subjects who are HMGCR positive are a previously unrecognized subgroup in the context of endocrine treatment.

Thus, as a seventh aspect of the present disclosure, there is provided an endocrine treatment product for use in treatment of a mammalian subject having a breast cancer, wherein said subject is HMGCR positive.

As an eighth aspect of the present disclosure, there is provided a use of an endocrine treatment product in the manufacture of a medicament for treatment of a mammalian subject having a breast cancer, wherein said subject is HMGCR positive.

The subject is "HMGCR positive" if any HMGCR protein or HMGCR mRNA parameter derived from said subject indicates that the subject is likely to benefit from an endocrine treatment. For example, the subject may be considered HMGCR positive if a relevant biological sample from the subject has been found to contain an amount of HMGCR protein or HMGCR mRNA corresponding to a sample value being higher than a relevant reference value. Relevant sample and reference values are discussed above in connection with the method aspects. Thus, the breast cancer subject may for example be considered HMGCR positive if a relevant sample, such as a tissue sample from a primary or secondary tumor, shows detectable HMGCR protein or HMGCR mRNA expression in relevant parts of the sample, such in the tumor cells. Further, the breast cancer subject may for example be considered HMGCR positive if such sample contains an amount of HMGCR protein corresponding to a cytoplasmic intensity which is higher than absent or a cytoplasmic fraction which is higher than 1%. From the present disclosure, the person skilled in the art, such as a pathologist, understands how to determine whether the subject is HMGCR positive of not.

In embodiments of the present disclosure, the "endocrine treatment product" may be selected from the group consisting of a selective estrogen receptor modulator (SERM), an aromatase inhibitor, and a steroidal estrogen receptor antagonist. The SERM may for example be selected from toremifene, raloxifene, droloxifene, arzoxifene and tamoxifen. The aromatase inhibitor may for example be selected from anastrozole, letrozole and exemestane. The steroidal estrogen receptor antagonist may for example be fulvestrant. In preferred embodiments, the endocrine treatment product is a SERM, such as tamoxifen.

Even though HMGCR expression is a powerful (independent) indicator of response to endocrine treatment in all groups of breast cancer subjects, it may be considered particularly relevant for the subjects having ER− breast cancers, since they have traditionally been considered non-responsive to such treatment.

Thus, in embodiments of the seventh and eighth aspect, the breast cancer may be ER−.

Tamoxifen has been the mainstay of adjuvant endocrine therapy for the last 25 years and a wealth of evidence exists supporting its role in the treatment of breast cancer, irrespective of menopausal status. The results of a meta-analysis have demonstrated significant reductions in both disease recurrence (41%), and breast cancer specific mortality (34%) when comparing 5 years tamoxifen to no adjuvant treatment (EBCTG: (2005) Lancet 365:1687-717).

HMGCR protein acts as a rate-limiting enzyme in the mevalonate pathway. Although cholesterol represents the main product of this pathway, it also produces a number of non-sterol isoprenoid side products, which have been shown to be important regulators of angiogenesis, proliferation, and migration (Liao J K (2002) J Clin Invest 110:285-8, Wejde J, et al (1992) Anticancer Res 12:317-24).

Despite an ever-growing body of literature describing the anti-neoplastic properties of statins, epidemiologic data regarding their preventive effect against cancer in general and breast cancer in particular remain inconclusive. Partly in view of the teachings of the present disclosure, the inventors believe that the mevalonate pathway plays a key role in certain breast cancers, in particular in ER negative and/or lymph node positive tumors.

In vitro studies have demonstrated that statin induced mevalonate depletion results in an adaptive induction of HMGCR protein expression in chinese hamster ovary cells (Goldstein J L and Brown M S (1990) Nature 343:425-30) and MCF-7 breast cancer cells (Duncan R E, et al (2005) Cancer Lett 224:221-8). Treatment of MCF-7 cells with mevastatin resulted in a 10- to 15-fold induction of HMGCR activity in association with a 2.5- to 3.5-fold induction of HMGCR mRNA expression.

Based on the fact and that statins have been shown to induce HMGCR protein expression and the finding that increased levels of HMGCR expression are associated with an improved response to tamoxifen in both ER positive and ER negative tumors, the inventors conclude that a combination of an endocrine treatment product and one or more statins is a new therapeutic option.

Thus, as ninth aspect of the present disclosure, there are provided products including an endocrine treatment product and a statin as a combined preparation for simultaneous, separate or sequential use in therapy, such as breast cancer therapy.

The combination of the two products may be provided in a "kit-of parts" or an article of manufacture, which may comprise instruction for the simultaneous, separate or sequential use in therapy, such as breast cancer therapy.

Thus, as a tenth aspect of the present disclosure, the is a provided a kit-of-parts including an endocrine treatment product and a statin.

For example, such a kit-of-parts may be for use in therapy, such as breast cancer therapy.

In embodiments of the ninth or tenth aspect, the breast cancer therapy may be therapy of a ER− and/or lymph node positive breast cancer.

Further, as an eleventh aspect of the present disclosure, there is provided a method of treatment of a mammalian subject in need thereof, wherein said subject has a breast cancer, comprising simultaneous, separate or sequential administration of a statin and an endocrine treatment product.

In embodiments of the eleventh aspect, the breast cancer may be a ER− and/or lymph node positive breast cancer.

The statin of the present disclosure may be selected from lipophilic/hydrophobic statins and hydrophobic statins. The lipophilic/hydrophobic statins comprise fluvastatin, lovastatin, simvastatin, atorvastatin and cerivastatin. The hydrophobic statins comprise pravastatin and rosuvastatin.

BRIEF DESCRIPTION OF THE FIGURES

With regard to FIGS. 1A-7B, tumor tissue was scored for high or low HMGCR level, wherein a high HMGCR level is CI=weak, moderate and strong and a low HMGCR level is a CI=absent. In FIGS. 1A-2B, 4A-5B, 7A and 7B a solid line represents HMGCR high subjects, and a dotted line represents HMGCR low subjects.

FIGS. 1A and 1B show the results of a survival analysis based on immunohistochemical staining of subjects diagnosed with invasive breast carcinoma. FIG. 1A shows recurrence free survival in patients treated with adjuvant tamoxifen. FIG. 1B shows recurrence free survival in patients who received no adjuvant endocrine treatment.

FIGS. 2A and 2B show the results of a survival analysis based on immunohistochemical staining of ER positive subjects diagnosed with invasive breast carcinoma. A fraction score of ER>10% was considered positive. FIG. 2A shows recurrence free survival in patients treated with adjuvant tamoxifen. FIG. 2B shows recurrence free survival in patients who received no adjuvant endocrine treatment.

FIG. 3A shows recurrence free survival in patients treated with adjuvant tamoxifen. FIG. 3B shows recurrence free survival in patients who received no adjuvant endocrine treatment.

FIGS. 4A and 4B show the results of a survival analysis based on immunohistochemical staining of subjects diagnosed with invasive breast carcinoma. FIG. 4A shows recurrence free survival in of node positive subjects treated with adjuvant tamoxifen. FIG. 4B shows recurrence free survival in node negative subjects treated with adjuvant tamoxifen.

FIGS. 5A and 5B show the results of a survival analysis based on immunohistochemical staining of ER positive subjects diagnosed with invasive breast carcinoma. A fraction score of ER>10% was considered positive. FIG. 5A shows recurrence free survival in of node positive subjects treated with adjuvant tamoxifen. FIG. 5B shows recurrence free survival in of node negative subjects treated with adjuvant tamoxifen.

FIG. 6A shows recurrence free survival in node positive subjects treated with adjuvant tamoxifen. FIG. 6B shows recurrence free survival in node negative subjects treated with adjuvant tamoxifen.

FIGS. 7A and 7B show the results of a survival analysis based on immunohistochemical staining of ER negative subjects diagnosed with breast invasive carcinoma. A fraction score of ER expression >10% was considered positive. FIG. 7A shows recurrence free survival in subjects treated with adjuvant tamoxifen. FIG. 7B shows recurrence free survival in subjects treated with adjuvant tamoxifen.

With regard to FIGS. 8A-12, tissue cores were scored for high or low HMGCR level, wherein a high HMGCR level is CI>absent and a low HMGCR level is a CI=absent. Further, a solid line represents a group of subjects given adjuvant tamoxifen, and a dotted line represents patients who received no adjuvant endocrine treatment.

Figure 8B:
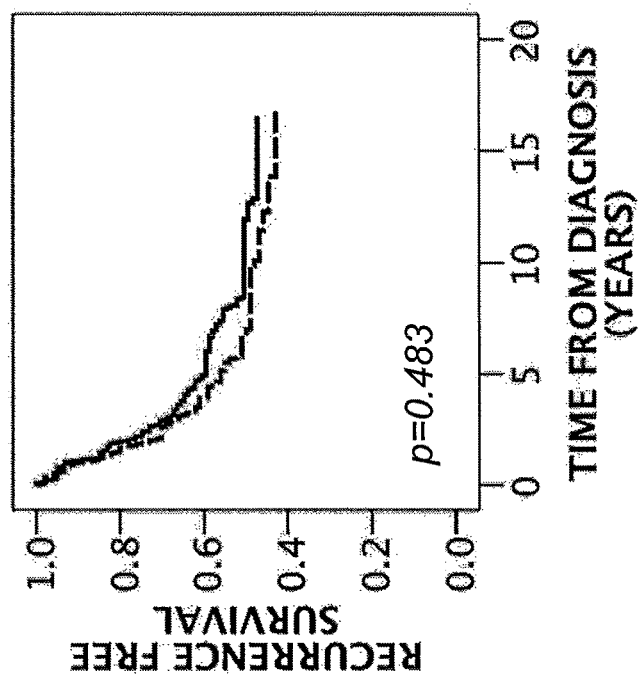
Figure 8A:
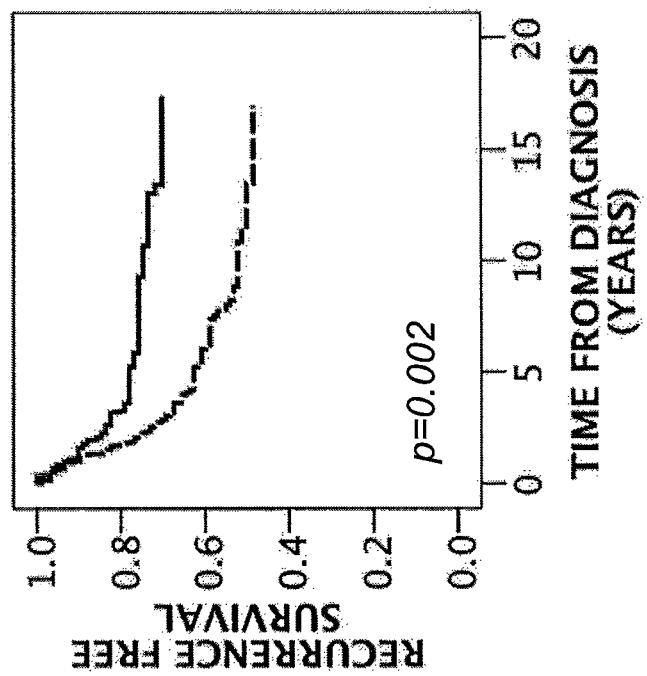

FIGS. 8A and 8B show the results of a survival analysis based on immunohistochemical staining of subjects diagnosed with invasive breast carcinoma. FIG. 8A shows recurrence free survival in HMGCR high patients. FIG. 8B shows recurrence free survival in HMGCR low patients.

Figure 9A:
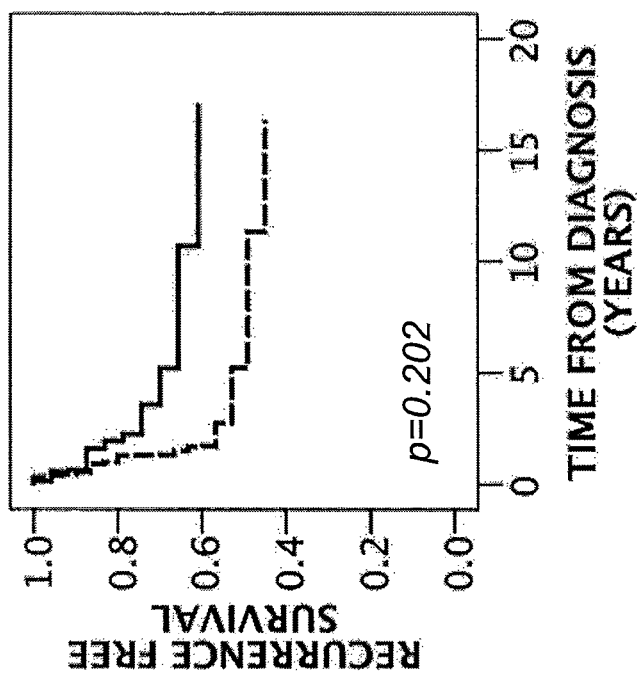
Figure 9B:
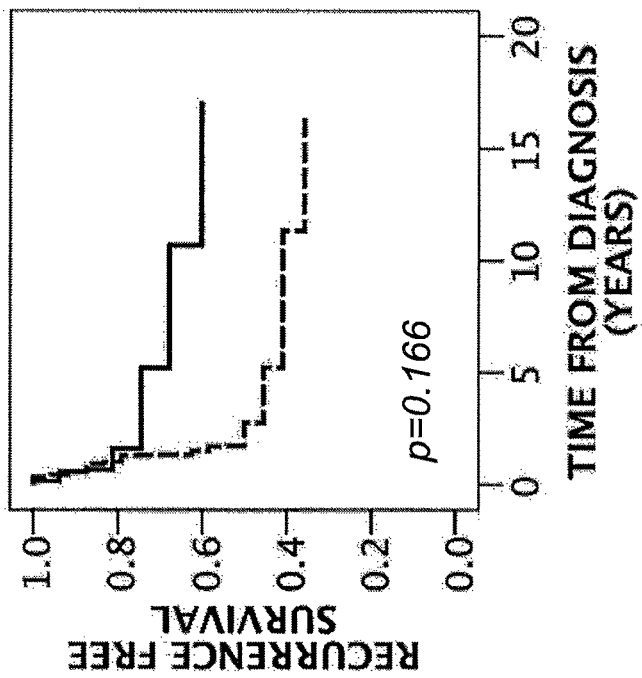

FIGS. 9A and 9B show the results of a survival analysis based on immunohistochemical staining of HMGCR positive and ER negative subjects diagnosed with invasive breast carcinoma. A fraction score of ER expression >10% was considered positive. FIG. 9A shows recurrence free survival. FIG. 9B shows recurrence free survival in node positive patients.

Figure 10A:
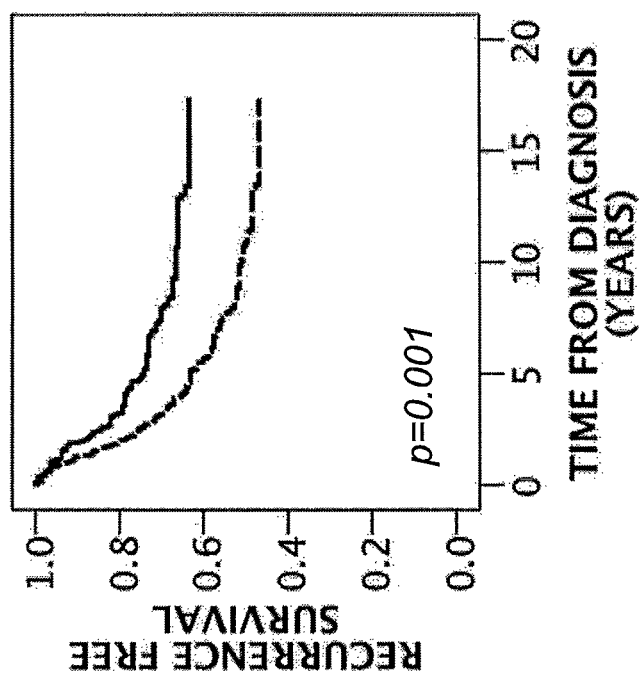
Figure 10B:
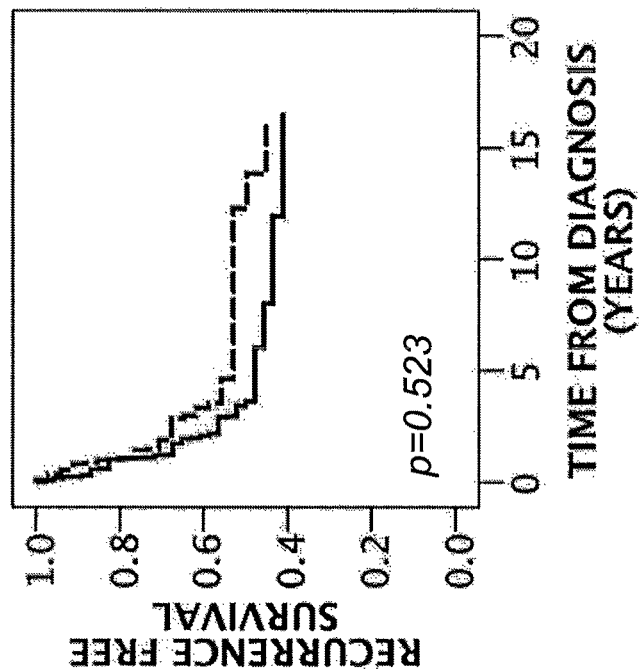

FIGS. 10A and 10B show the results of a survival analysis based on immunohistochemical staining of subjects diagnosed with invasive breast carcinoma. The subjects were classified as ER positive or ER negative, wherein a fraction score of >10% was considered positive and a fraction score of <10% was considered negative. FIG. 10A shows recurrence free survival in HMGCR positive or ER positive subjects. FIG. 10B shows recurrence free survival in HMGCR negative and ER negative subjects.

Figure 11B:
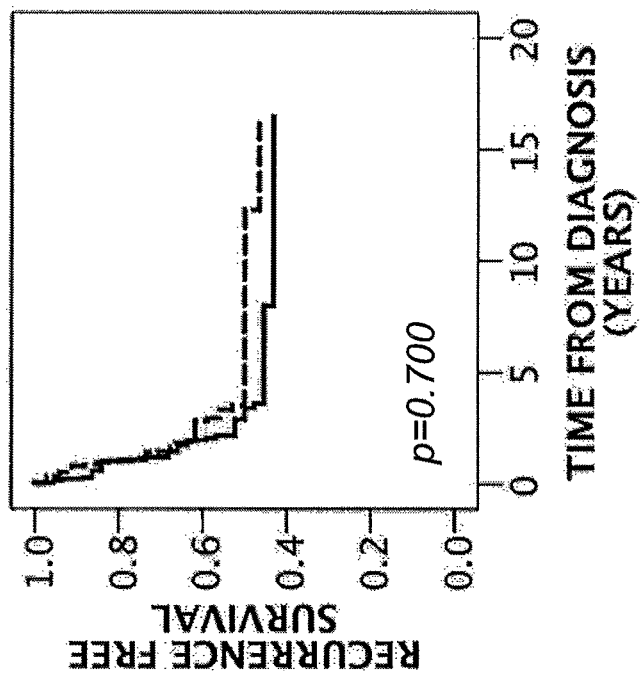
Figure 11A:
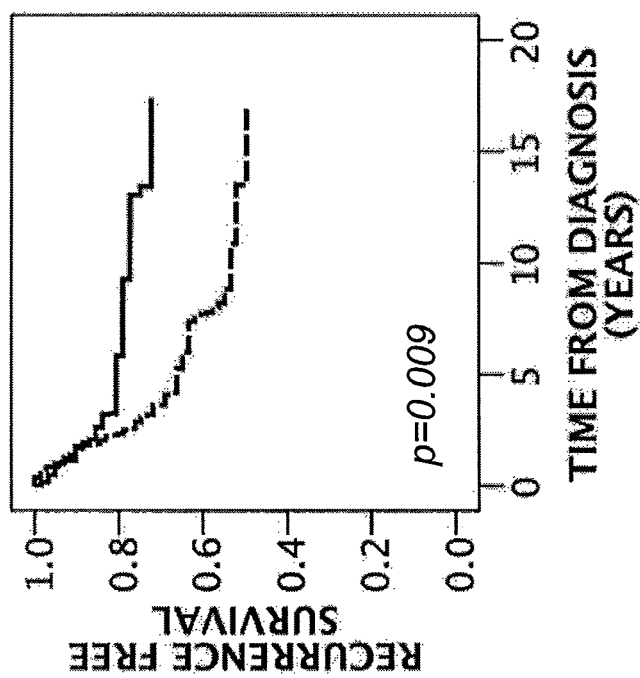

FIGS. 11A and 11B show the results of a survival analysis based on immunohistochemical staining of subjects diagnosed with invasive breast carcinoma. The subjects were classified as PR positive or PR negative, wherein a fraction score of >10% was considered positive and a fraction score of <10% was considered negative. FIG. 11A shows recurrence free survival in HMGCR positive or PR positive subjects. FIG. 11B shows recurrence free survival in HMGCR negative and PR negative subjects.

Figure 12:
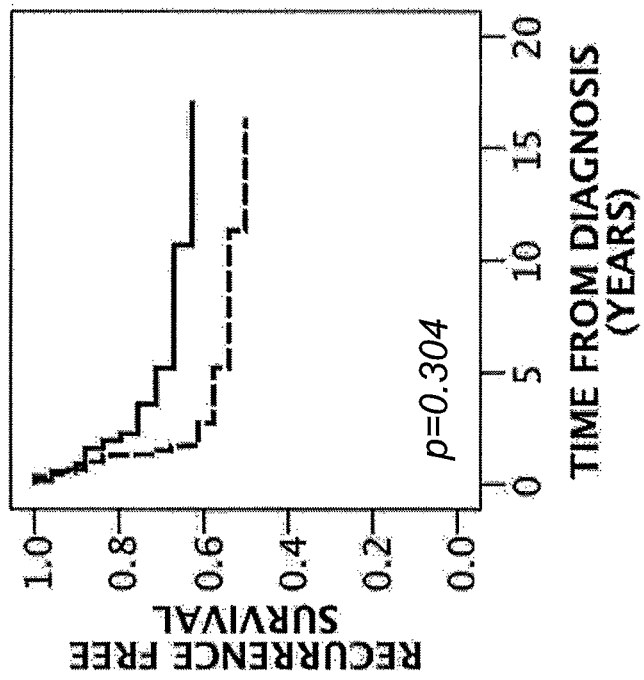

FIG. 12 shows the recurrence free survival of HMGCR positive and PR negative subjects diagnosed with invasive breast carcinoma. A fraction score of PR expression >10% was considered positive.

Figure 13A:
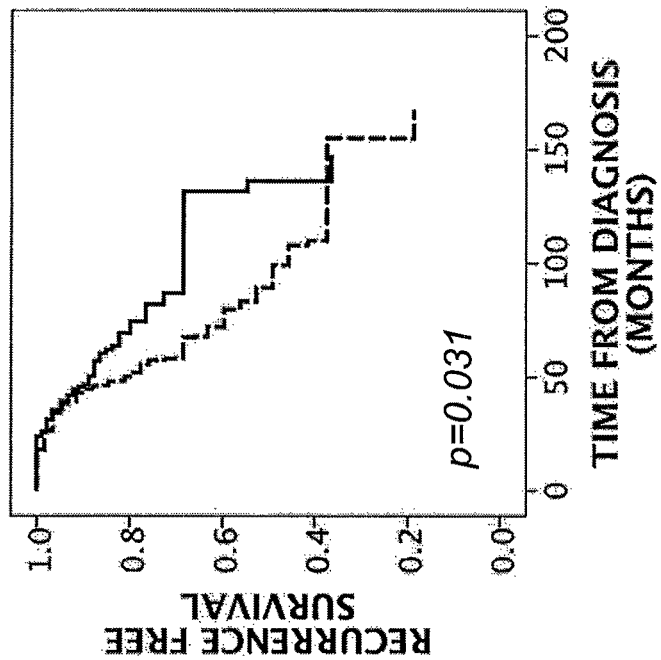
Figure 13B:
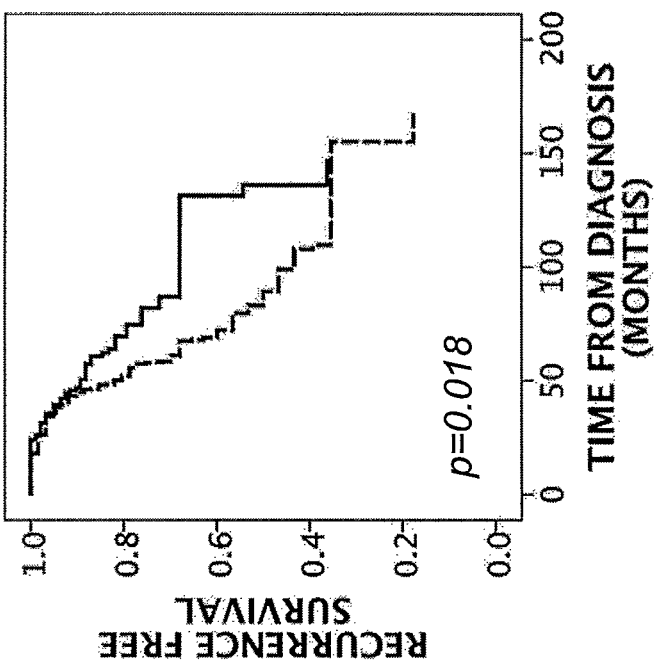

FIGS. 13A and 13B show the results of a survival analysis based on micro array analysis of 155 subjects diagnosed with invasive breast carcinoma. All subjects were treated with adjuvant tamoxifen. The solid line represents HMGCR high subjects, and the dotted line represents HMGCR low subjects. FIG. 13A shows recurrence free survival. FIG. 13B shows recurrence free survival in ER positive subjects only.

EXAMPLES

Generation of Mono-Specific Antibodies Against HMGCR and Use Thereof to Detect HMGCR in Normal and Cancerous Samples 1. Generation of Antigen
a) Materials and Methods A suitable fragment of the target protein encoded by the EnsEMBL Gene ID ENSG00000113161 was selected using bioinformatic tools with the human genome sequence as template (Lindskog M et al. (2005) Biotechniques 38:723-727, EnsEMBL, www.ensembl.org). The fragment was used as template for the production of a 140 amino acid long fragment corresponding to amino acids 742-881 (SEQ ID NO:1) of the HMGCR protein (SEQ ID NO:2; EnsEMBL entry no. ENSP00000287936).

A fragment of the HMGCR gene transcript containing nucleotides 2274-2693 of EnsEMBL entry number ENST00000287936 (SEQ ID NO:3), was isolated by a Superscript™ One-Step RT-PCR amplification kit with Platinum® Taq (Invitrogen) and a human total RNA pool panel as template (Human Total RNA Panel IV, BD Biosciences Clontech). Flanking restriction sites NotI and AscI were introduced into the fragment through the PCR amplification primers, to allow in-frame cloning into the expression vector (forward primer: ATGGCTGGGAGCATAGGAG, reverse primer: TCCTTGGAGGTCTTGTAAATTG). Then, the downstream primer was biotinylated to allow solid-phase cloning as previously described, and the resulting biotinylated PCR product was immobilized onto Dynabeads M280 Streptavidin (Dynal Biotech) (Larsson M et al. (2000) J. Biotechnol. 80:143-157). The fragment was released from the solid support by NotI-AscI digestion (New England Biolabs), ligated into the pAff8c vector (Larsson M et al, supra) in frame with a dual affinity tag consisting of a hexahistidyl tag for immobilized metal ion chromatography (IMAC) purification and an immunopotentiating albumin binding protein (ABP) from streptococcal protein G (Sjölander A et al. (1997) J. Immunol. Methods 201:115-123; Ståhl S et al. (1999) Encyclopedia of Bioprocess Technology: Fermentation, Biocatalysis and Bioseparation (Fleckinger M C and Drew S W, eds) John Wiley and Sons Inc., New York, pp 49-63), and transformed into E. coli BL21(DE3) cells (Novagen). The sequences of the clones were verified by dye-terminator cycle sequencing of plasmid DNA amplified using TempliPhi DNA sequencing amplification kit (GE Healthcare, Uppsala, Sweden) according to the manufacturer's recommendations.

BL21(DE3) cells harboring the expression vector were inoculated in 100 ml 30 g/l tryptic soy broth (Merck KGaA) supplemented with 5 g/l yeast extract (Merck KGaA) and 50 mg/l kanamycin (Sigma-Aldrich) by addition of 1 ml of an overnight culture in the same culture medium. The cell culture was incubated in a 1 liter shake flask at 37° C. and 150 rpm until the optical density at 600 nm reached 0.5-1.5. Protein expression was then induced by addition of isopropyl-β-D-thiogalactopyranoside (Apollo Scientific) to a final concentration of 1 mM, and the incubation was continued overnight at 25° C. and 150 rpm. The cells were harvested by centrifugation at 2400 g, and the pellet was re-suspended in 5 ml lysis buffer (7 M guanidine hydrochloride, 47 mM $Na_2HPO_4$, 2.65 mM $NaH_2PO_4$, 10 mM Tris-HCl, 100 mM NaCl, 20 mM β-mercaptoethanol; pH=8.0) and incubated for 2 hours at 37° C. and 150 rpm. After centrifugation at 35300 g, the supernatant containing the denatured and solubilized protein was collected.

The $His_6$-tagged fusion protein was purified by immobilized metal ion affinity chromatography (IMAC) on columns with 1 ml Talon® metal ($Co^{2+}$) affinity resin (BD Biosciences Clontech) using an automated protein purification procedure (Steen J et al. (2006) Protein Expr. Purif. 46:173-178) on an ASPEC XL4™ (Gilson). The resin was equilibrated with 20 ml denaturing washing buffer (6 M guanidine hydrochloride, 46.6 mM $Na_2HPO_4$, 3.4 mM $NaH_2PO_4$, 300 mM NaCl, pH 8.0-8.2). Clarified cell lysates were then added to the column. Thereafter, the resin was washed with a minimum of 31.5 ml washing buffer prior to elution in 2.5 ml elution buffer (6 M urea, 50 mM $NaH_2PO_4$, 100 mM NaCl, 30 mM acetic acid, 70 mM Na-acetate, pH 5.0). The eluted material was fractioned in three pools of 500, 700 and 1300 µl. The 700 µl fraction, containing the antigen, and the pooled 500 and 1300 µl fractions were stored for further use.

The antigen fraction was diluted to a final concentration of 1 M urea with phosphate buffered saline (PBS; 1.9 mM $NaH_2PO_4$, 8.1 mM $Na_2HPO_4$, 154 mM NaCl) followed by a concentration step to increase the protein concentration using Vivapore 10/20 ml concentrator with molecular weight cut off at 7500 Da (Vivascience AG). The protein concentration was determined using a bicinchoninic acid (BCA) micro assay protocol (Pierce) with a bovine serum albumin standard according to the manufacturer's recommendations. The protein quality was analyzed on a Bioanalyzer instrument using the Protein 50 or 200 assay (Agilent Technologies).

b) Results

A gene fragment corresponding to nucleotides 2274-2693 of the long transcript (SEQ ID NO:3) of the HMGCR gene and encoding a peptide (SEQ ID NO:1) consisting of amino acids 742 to 881 of the target protein HMGCR (SEQ ID NO:2) was successfully isolated by RT-PCR from a human RNA pool using primers specific for the protein fragment. The 140 amino acid fragment (SEQ ID NO:1) of the target protein (SEQ ID NO:2) was designed to lack transmembrane regions to ensure efficient expression in E. coli, and to lack any signal peptide, since those are cleaved off in the mature protein. In addition, the protein fragment was designed to consist of a unique sequence with low homology with other human proteins, to minimize cross reactivity of generated affinity reagents, and to be of a suitable size to allow the formation of conformational epitopes and still allow efficient cloning and expression in bacterial systems.

A clone encoding the correct amino acid sequence was identified, and, upon expression in E. coli, a single protein of the correct size was produced and subsequently purified using immobilized metal ion chromatography. After dilution of the eluted sample to a final concentration of 1 M urea and concentration of the sample to 1 ml, the concentration of the protein fragment was determined to be 11.7 mg/ml and was 84.2% pure according to purity analysis.

2. Generation of Antibodies a) Materials and Methods

The purified HMGCR fragment as obtained above was used as antigen to immunize a rabbit in accordance with the national guidelines (Swedish permit no. A 84-02). The rabbit was immunized intramuscularly with 200 µg of antigen in Freund's complete adjuvant as the primary immunization, and boosted three times in four week intervals with 100 µg antigen in Freund's incomplete adjuvant.

Antiserum from the immunized animal was purified by a three-step immunoaffinity based protocol (Agaton C et al. (2004) J. Chromatogr. A 1043:33-40; Nilsson P et al. (2005) Proteomics 5:4327-4337). In the first step, 7 ml of total antiserum was buffered with 10×PBS to a final concentration of 1×PBS (1.9 mM $NaH_2PO_4$, 8.1 mM $Na_2HPO_4$, 154 mM NaCl), filtered using a 0.45 µm pore-size filter (Acrodisc®, Life Science) and applied to an affinity column containing 5 ml N-hydroxysuccinimide-activated Sepharose™ 4 Fast Flow (GE Healthcare) coupled to the dual affinity tag protein $His_6$-ABP (a hexahistidyl tag and an albumin binding protein tag) expressed from the pAff8c vector and purified in the same way as described above for the antigen protein fragment. In the second step, the flow-through, depleted of antibodies against the dual affinity tag $His_6$-ABP, was loaded at a flow rate of 0.5 ml/min on a 1 ml Hi-Trap NHS-activated HP column (GE Healthcare) coupled with the HMGCR protein fragment used as antigen for immunization (SEQ ID NO:1). The $His_6$-ABP protein and the protein fragment antigen were coupled to the NHS activated matrix as recommended by the manufacturer. Unbound material was washed away with 1×PBST (1×PBS, 0.1% Tween20, pH 7.25), and captured antibodies were eluted using a low pH glycine buffer (0.2 M glycine, 1 mM EGTA, pH 2.5). The eluted antibody fraction was collected automatically, and loaded onto two 5 ml HiTrap™ desalting columns (GE Healthcare) connected in series for efficient buffer exchange in the third step. The second and third purification steps were run on the ÄKTAxpress™ platform (GE Healthcare). The antigen selective (mono-specific) antibodies (msAbs) were eluted with PBS buffer, supplemented with glycerol and $NaN_3$ to final concentrations of 40% and 0.02%, respectively, for long term storage at −20° C. (Nilsson P et al. (2005) Proteomics 5:4327-4337).

The specificity and selectivity of the affinity purified antibody fraction were analyzed by binding analysis against the antigen itself and against 383 other human protein fragments in a protein array set-up (Nilsson P et al. (2005) Proteomics 5:4327-4337). The protein fragments were diluted to 40 µg/ml in 0.1 M urea and 1×PBS (pH 7.4) and 50 µl of each were transferred to the wells of a 96-well spotting plate. The protein fragments were spotted in duplicate and immobilized onto epoxy slides (SuperEpoxy, TeleChem) using a pin-and-ring arrayer (Affymetrix 427). The slide was washed in 1×PBS (5 min) and the surface was then blocked (SuperBlock®, Pierce) for 30 minutes. An adhesive 16-well silicone mask (Schleicher & Schuell) was applied to the glass before the mono-specific antibodies were added (diluted 1:2000 in 1×PBST to appr. 50 ng/ml) and incubated on a shaker for 60 min. Affinity tag-specific IgY antibodies were co-incubated with the mono-specific antibodies in order to quantify the amount of protein in each spot. The slide was washed with 1×PBST and 1×PBS twice for 10 min each. Secondary antibodies (goat anti-rabbit antibody conjugated with Alexa 647 and goat anti-chicken antibody conjugated with Alexa 555, Molecular Probes) were diluted 1:60000 to 30 ng/ml in 1×PBST and incubated for 60 min. After the same washing procedure, as for the first incubation, the slide was spun dry and scanned (G2565BA array scanner, Agilent), thereafter images were quantified using image analysis software (GenePix 5.1, Axon Instruments).

b) Results

The quality of polyclonal antibody preparations has proven to be dependent on the degree of stringency in the antibody purifications, and it has previously been shown that depletion of antibodies directed against epitopes not originated from the target protein is necessary to avoid cross-reactivity to other proteins and background binding (Agaton C et al.

(2004) J. Chromatogr. A 1043:33-40). Thus, a protein microarray analysis was performed to ensure that mono-specific polyclonal antibodies of high specificity had been generated by depletion of antibodies directed against the $His_6$-tag as well as of antibodies against the ABP-tag.

To quantify the amount of protein in each spot of the protein array, a two-color dye labeling system was used, with a combination of primary and secondary antibodies. Tag-specific IgY antibodies generated in hen were detected with a secondary goat anti-hen antibody labeled with Alexa 555 fluorescent dye. The specific binding of the rabbit msAb to its antigen on the array was detected with a fluorescently Alexa 647 labeled goat anti-rabbit antibody. The protein array analysis showed that the affinity purified mono-specific antibody against HMGCR is highly selective to the correct protein fragment and has a very low background to all other protein fragments analyzed on the array.

3. Tissue Profiling by Immunohistochemistry a) Material and Methods

In total, 576 paraffin cores containing human tissues were analyzed using the mono-specific antibody sample obtained in Examples, section 2. All tissues used as donor blocks for tissue microarray (TMA) production were selected from the archives at the Department of Pathology, University Hospital, Uppsala, in agreement with approval from the local ethical committee. All tissue sections used for TMA analysis were examined to determine diagnosis and to select representative areas in donor blocks. Normal tissue was defined as microscopically normal (non-neoplastic) and was most often selected from specimens collected from the vicinity of surgically removed tumors. Cancer tissue was reviewed for diagnosis and classification. All tissues were formalin fixated, paraffin embedded, and sectioned for diagnostic purposes.

The TMA production was performed essentially as previously described (Kononen J et al. (1998) Nature Med. 4:844-847; Kallioniemi O P et al. (2001) Hum. Mol. Genet. 10:657-662). Briefly, a hole was made in the recipient TMA block and a cylindrical core tissue sample from the donor block was acquired and deposited in the recipient TMA block. This was repeated in an automated tissue arrayer from Beecher Instrument (ATA-27, Beecher Instruments, Sun Prairie, Calif., USA) until a complete TMA design was produced. TMA recipient blocks were baked at 42° C. for 2 h prior to sectioning.

The design of TMA:s was focused on obtaining samples from a large range of representative normal tissues, and on including representative cancer tissues. This has previously been described in detail in Kampf C et al. (2004) Clin. Proteomics 1:285-300. In brief, samples from 48 normal tissues and from 20 of the most common cancer types affecting humans were selected. In total, eight different designs of TMA blocks, each containing 72 cores of tissue with 1 mm diameter, were produced. Two of the TMA:s represented normal tissues, corresponding to 48 different normal tissues in triplicates from different individuals. The remaining 6 TMA:s represented cancer tissue from 20 different types of cancer. For 17 of the 20 cancer types, 12 individually different tumors were sampled, and for the remaining 3 cancer types, 4 individually different tumors were sampled, all in duplicates from the same tumor. The TMA blocks were sectioned with 4 µm thickness using a waterfall microtome (Leica), and placed onto SuperFrost® (Roche Applied Science) glass slides for IHC analysis.

Automated IHC was performed as previously described (Kampf C et al. (2004) Clin. Proteomics 1:285-300). In brief, the glass slides were incubated for 45 min in 60° C., de-paraffinized in xylene (2×15 min) and hydrated in graded alcohols. For antigen retrieval, slides were immersed in TRS (Target Retrieval Solution, pH 6.0, DakoCytomation) and boiled for 4 min at 125° C. in a Decloaking Chamber® (Biocare Medical). Slides were placed in the Autostainer® (DakoCytomation) and endogenous peroxidase was initially blocked with $H_2O_2$ (DakoCytomation). The slides were incubated for 30 min at room temperature with the primary antibody obtained as in Examples, Section 2, followed by incubation for 30 min at room temperature with goat anti-rabbit peroxidase conjugated Envision®. Between all steps, slides were rinsed in wash buffer (DakoCytomation). Finally, diaminobenzidine (DakoCytomation) was used as chromogen and Harris hematoxylin (Sigma-Aldrich) was used for counterstaining. The slides were mounted with Pertex® (Histolab).

All immunohistochemically stained sections from the eight different TMA:s were scanned using a ScanScope T2 automated slide-scanning systems (Aperio Technologies). In order to represent the total content of the eight TMA:s, 576 digital images were generated. Scanning was performed at 20 times magnification. Digital images were separated and extracted as individual tagged image file format (TIFF) files for storage of original data. In order to be able to handle the images in a web-based annotation system, the individual images were compressed from TIFF format into JPEG format. All images of immunohistochemically stained tissue were manually evaluated under the microscope and annotated by a certified pathologist or by specially educated personnel, subsequently verified by a pathologist.

Annotation of each different normal and cancer tissue was performed using a simplified scheme for classification of IHC outcome. Each tissue was examined for representativity and immunoreactivity. The different tissue specific cell types included in each normal tissue type were annotated. For each cancer, tumor cells and stroma were annotated. Basic annotation parameters included an evaluation of i) subcellular localization (nuclear and/or cytoplasmic/membranous), ii) staining intensity (SI) and iii) fraction of stained cells (FSC). Staining intensity was subjectively evaluated in accordance to standards used in clinical histo-pathological diagnostics and outcome was classified as: absent=no immunoreactivity, weak=faint immunoreactivity, moderate=medium immunoreactivity or strong=distinct and strong immunoreactivity. The fraction of stained cells was estimated and classified as <2%, 2-25%, >25-75% or >75% immunoreactive cells of the relevant cell population. Based on both the intensity and fraction of immunoreactive cells, a "staining score" was given for each tissue sample: 0=negative, 1=weak, 2=moderate and 3=strong. N.R. means that no representative tissues were present. In detail, the staining score was given according to the following criteria: 0 was given if SI=absent or weak and FSC ≤25%; 1 was given if SI=weak and FSC >25% or if SI=moderate and FSC ≤25%; 2 was given if SI=moderate and FSC >25% or if SI=strong and FSC ≤25% and SI=moderate;

and finally 3 was given if SI=strong and FSC >25%. See also table 1. The skilled artisan should recognize that this procedure is similar to a calculation of an Allred score, see e.g., Allred et al. (1998) Mod Pathol 11(2), 155.

TABLE 1

Staining score

| Staining score | Staining intensity | Fraction of stained cells |
|---|---|---|
| 0 | absent | <2% |
| 0 | absent | 2-25% |
| 0 | absent | >25-75% |
| 0 | absent | >75% |
| 0 | weak | <2% |
| 0 | weak | 2-25% |
| 1 | weak | >25-75% |
| 1 | weak | >75% |
| 1 | moderate | <2% |
| 1 | moderate | 2-25% |
| 2 | moderate | >25-75% |
| 2 | moderate | >75% |
| 2 | strong | <2% |
| 2 | strong | 2-25% |
| 3 | strong | >25-75% |
| 3 | strong | >75% | b) Results

The results from tissue profiling with the mono-specific antibody generated towards a recombinant protein fragment of the human target protein HMGCR obtained as in Examples, Section 2 showed a particular immunoreactivity in several normal tissues. Table 2 shows the HMGCR protein expression pattern in normal human tissues. Using IHC and TMA technology, 144 spots (1 mm in diameter) representing 48 different types of normal tissue were screened for expression of HMGCR. Immunoreactivity was observed mainly in cytoplasm of most tissues. Some cases showed additional nuclear or membranous positivity. Strongest staining was found in glandular epithelia. In a few cases no representative tissue (N.R.) were observed.

TABLE 2

Expression pattern of HMGCR in normal tissues

| Tissue type | Cell type | Staining score |
|---|---|---|
| Adrenal gland | cortical cells | 3 |
| Appendix | glandular cells | 3 |
|  | lymphoid tissue | 1 |
| Bone marrow | bone marrow poietic cells | 3 |
| Breast | glandular cells | 2 |
| Bronchus | respiratory epithelial cells | 2 |
| Cerebellum | cells in granular layer | 2 |
|  | cells in molecular layer | 3 |
|  | purkinje cells | 3 |
| Cerebral cortex | glial cells | 0 |
|  | neuronal cells | 3 |
| Cervix, uterine | glandular cells | 3 |
|  | squamous epithelial cells | 1 |
| Colon | glandular cells | 3 |
| Corpus, uterine 1 | cells in endometrial stroma | 1 |
|  | glandular cells | 3 |
| Corpus, uterine 2 | cells in endometrial stroma | 1 |
|  | glandular cells | 3 |
| Duodenum | glandular cells | 3 |
| Epididymis | glandular cells | 3 |
| Esophagus | squamous epithelial cells | 2 |
| Fallopian tube | glandular cells | 2 |
| Gall bladder | glandular cells | 3 |
| Heart muscle | myocytes | 2 |

TABLE 2-continued

Expression pattern of HMGCR in normal tissues

| Tissue type | Cell type | Staining score |
|---|---|---|
| Hippocampus | glial cells | 0 |
|  | neuronal cells | 2 |
| Kidney | cells in glomeruli | 0 |
|  | cells in tubules | 2 |
| Lateral ventricle | glial cells | 0 |
|  | neuronal cells | 1 |
| Liver | bile duct cells | 1 |
|  | hepatocytes | 1 |
| Lung | alveolar cells | 2 |
|  | macrophages | 1 |
| Lymph node | lymphoid cells outside reaction centra | 2 |
|  | reaction center cells | 2 |
| Nasopharynx | respiratory epithelial cells | 2 |
| Oral mucosa | squamous epithelial cells | 2 |
| Ovary | follicle cells | N.R. |
|  | ovarian stromal cells | 1 |
| Pancreas | exocrine glandular cells | 3 |
|  | islet cells | 1 |
| Parathyroid gland | glandular cells | 3 |
| Placenta | decidual cells | 1 |
|  | trophoblastic cells | 2 |
| Prostate | glandular cells | 2 |
| Rectum | glandular cells | 3 |
| Salivary gland | glandular cells | 2 |
| Seminal vesicle | glandular cells | 2 |
| Skeletal muscle | myocytes | 2 |
| Skin | adnexal cells | N.R. |
|  | epidermal cells | 2 |
| Small intestine | glandular cells | 3 |
| Smooth muscle | smooth muscle cells | 0 |
| Soft tissue 1 | mesenchymal cells | 2 |
| Soft tissue 2 | mesenchymal cells | 2 |
| Spleen | cells in red pulp | 2 |
|  | cells in white pulp | 2 |
| Stomach 1 | glandular cells | 3 |
| Stomach 2 | glandular cells | 3 |
| Testis | cells in seminiferus ducts | 1 |
|  | leydig cells | 3 |
| Thyroid gland | glandular cells | 2 |
| Tonsil | lymphoid cells outside reaction centra | 2 |
|  | reaction center cells | 1 |
|  | squamous epithelial cells | 2 |
| Urinary bladder | urothelial cells | 2 |
| Vagina | squamous epithelial cells | 1 |
| Vulva/anal skin | squamous epithelial cells | 2 |

HMGCR protein expression was further evaluated in tissue samples from various cancer types. Table 3 shows the level of HMGCR expression in 12 different breast carcinoma tissues samples. All of these samples showed representative tissue and ten showed positivity, i.e., a staining score of higher than zero. HMGCR expression was observed in cytoplasm.

TABLE 3

Expression pattern of HMGCR

| | Tissue sample | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Staining score | 3 | 2 | 2 | 1 | 1 | 1 | 1 | 1 | 1 | 1 | 0 | 0 |

4. Randomized Premenopausal Cohort TMA a) Material and Methods

Between 1984 and 1991, 564 pre-menopausal women with primary breast cancer in the South and Southeast regions of Sweden were enrolled in a multi-centre clinical trial and randomly assigned to either two years of adjuvant tamoxifen (n=276) or a control group (n=288). The control group did not receive adjuvant endocrine treatment, i.e. tamoxifen. The inclusion criteria were pre-menopausal patients, or patients younger than 50 years, with stage II (pT2 N0 M0, pT1-2 N1 M0) invasive breast cancer treated by modified mastectomy or breast conserving surgery with axillary lymph node dissection. Post-operative radiotherapy (50 Gy) was administered after breastconserving surgery and all lymph node-positive patients received locoregional radiotherapy. Less than 2% of the patients received adjuvant systemic chemotherapy. The median follow-up time for patients without breast cancer events was 13.9 years. Median age at diagnosis was 45 (25-57) years. The study design is described in detail elsewhere (Rydén L et al, Eur J Cancer, 2005, 41(2): 256-64). Ethical permission was obtained from the Local Ethics Committees at Lund and Linköping Universities.

Tissue blocks from 500 of the 564 patients could be retrieved for TMA-construction. All cases had been histopathologically re-evaluated on hematoxylin and eosin stained slides. TMA:s were constructed by sampling 2×0.6 mm cores per case from areas representative of invasive cancer, using an manual arraying device (MTA-1, Beecher Inc, WI, USA). Four μm sections were dried, deparaffinized an pretreated using the PT-link system (DAKO, Copenhagen, Denmark), then stained in a Techmate 500 (DAKO, Copenhagen, Denmark) with a polyclonal anti-HMGCR antibody (Catalog #07-457, Upstate) diluted 1:250, which antibody selectively interacts with a peptide consisting of the sequence SEQ ID NO:4. IHC staining of ER and PR had been performed previously. In line with current clinical praxis, a cut-off at 10% positive nuclei was used to define hormone receptor positivity.

For statistical analyses, the cytoplasmic intensity (CI) level was evaluated, in line with what is described in Examples, Section 3 above. The level of staining intensity of the cytoplasm was subjectively evaluated in accordance to standards used in clinical histo-pathological diagnostics and outcome was classified as: absent=no immunoreactivity, weak=faint immunoreactivity, moderate=medium immunoreactivity or strong=distinct and strong immunoreactivity. Based on the survival trends for all different strata, a dichotomized variable were constructed for further statistical analyses. Two categories were defined: "HMGCR high" corresponding to CI=weak, moderate and strong and "HMGCR low" corresponding to CI=absent This classification of samples was used for RFS analysis according to the Kaplan-Meier estimator, and the log-rank test was used to compare survival in different strata. ER and PR negativity was defined as <10% positively staining nuclei, according to current clinical guidelines in Sweden. All statistical tests were two-sided, and p-values of <0.05 were considered significant. All calculations were made with the statistical package SPSS 17.0 (SPSS Inc. Illinois, USA).

b) Results

In this results section, "HMGCR" refers to HMGCR protein. For the present study, immunohistochemical analysis of HMGCR expression could be performed on 423 tumors. The remaining cores either did not contain invasive cancer or had been lost during histoprocessing. Of the 423 analyzed tumors, 324 were ER positive (i.e. ERα+), defined as >10% ER nuclear fraction, which is in line with the clinically established cut-off used for hormone receptor assessment.

Figure 1B:
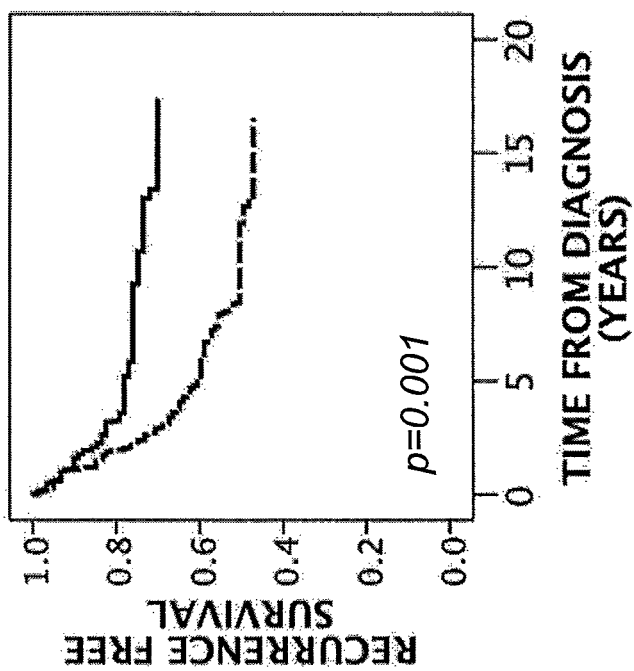
Figure 1A:
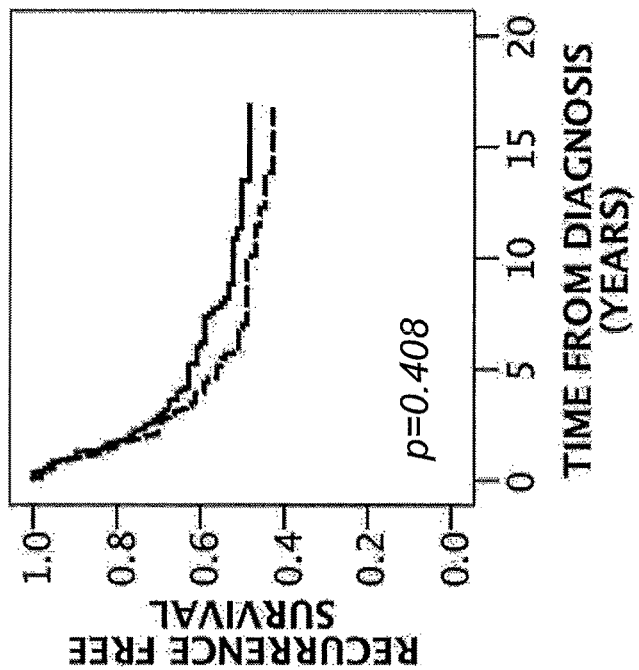

Analysis of recurrence free survival (RFS) based on high or low HMGCR protein levels in patients treated with tamoxifen and a control group of patients that received no adjuvant endocrine therapy are presented in FIGS. 1a and 1b, respectively. This analysis reveals a significantly better RFS for the HMGCR high category than for the HMGCR low category as seen in FIG. 1a (p=0.001).

Figure 2B:
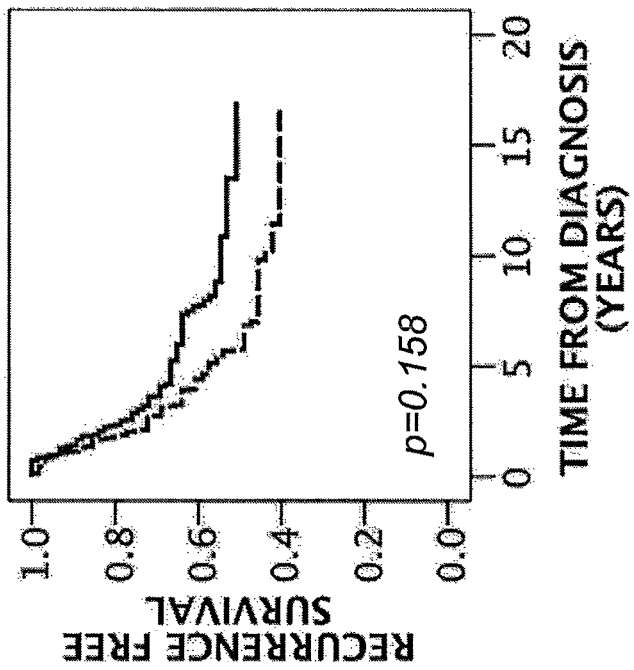
Figure 2A:
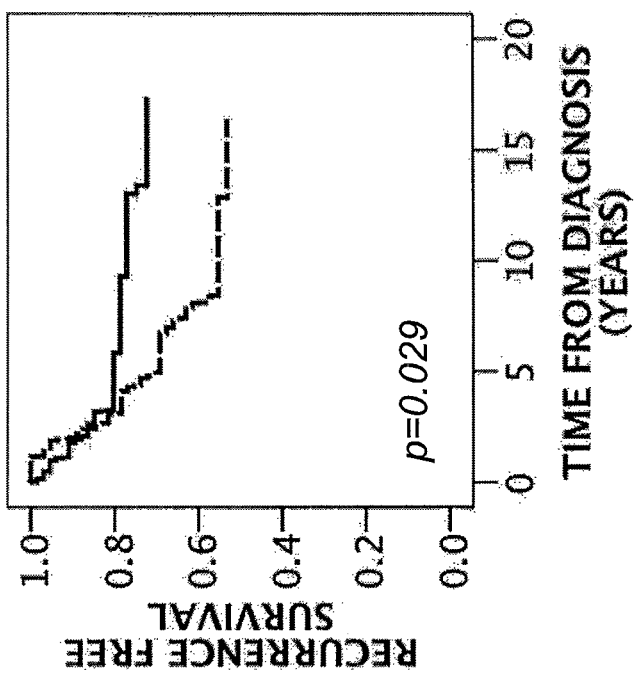

Analysis of RFS based on high or low HMGCR levels in ER positive patients of the tamoxifen treated patients and the control group are presented in FIGS. 2a and 2b, respectively. This analysis reveals a significantly better RFS for the HMGCR high category of the tamoxifen treated subjects as seen in FIG. 2a.

Figures 3A, 3B:
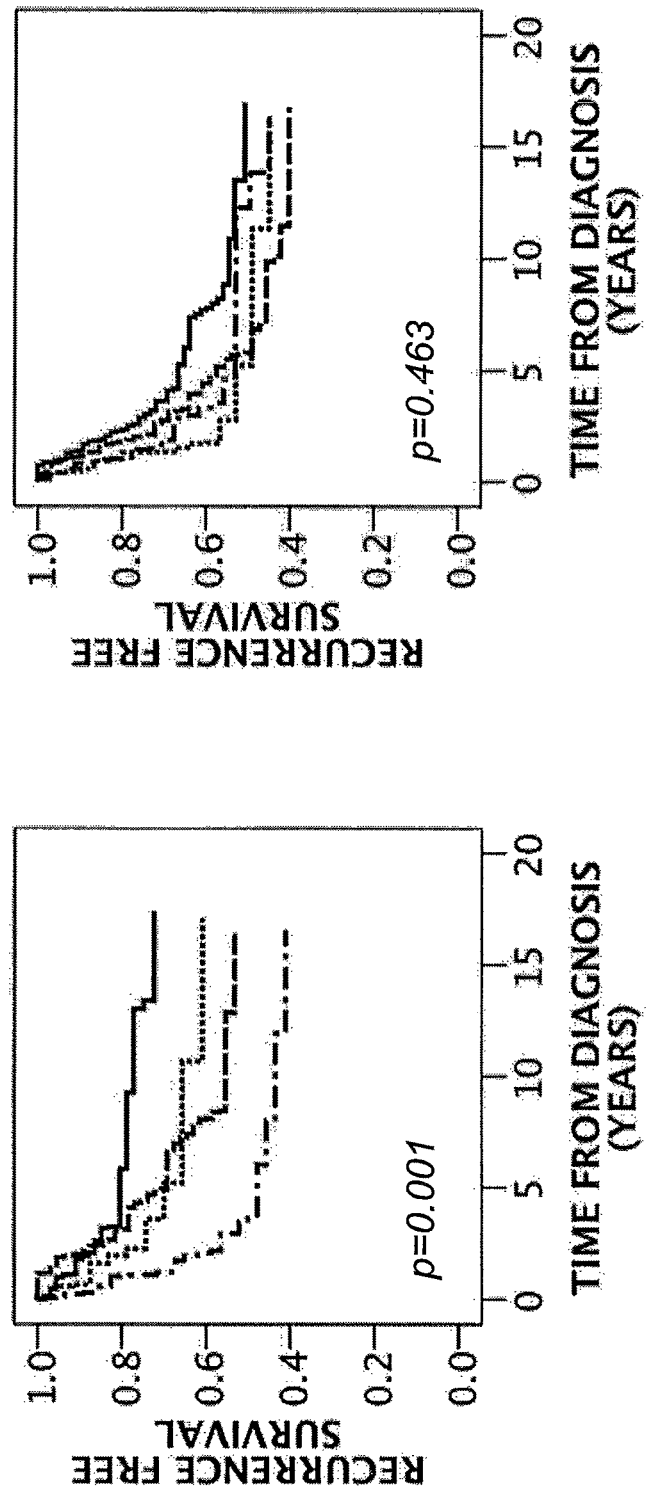
FIGS. 3A and 3B show the impact on survival if splitting subjects into groups with different combinations of HMGCR protein expression status and ER status. Briefly, all subjects were split into four groups based on HMGCR status and ER status, i.e. subjects that are HMGCR positive and ER positive, subjects that are HMGCR positive and ER negative, subjects that are HMGCR negative and ER positive or subjects that are HMGCR negative and ER negative. ER positive=fraction score of >10% and ER negative=fraction score of <10%.

In light of the apparent influence of HMGCR on tamoxifen response in this cohort, the impact on RFS in strata with different combinations of HMGCR protein expression status and ER status were analyzed. Briefly, all subjects were split into four groups based on HMGCR and ER status, i.e. subjects that are HMGCR positive and ER positive, subjects that are HMGCR positive and ER negative, subjects that are HMGCR negative and ER positive and subjects that are HMGCR negative and ER negative. The analysis revealed that these strata were associated with differences in RFS in the tamoxifen treated cohort (p=0.001) (FIG. 3a). However very small differences between the strata in the untreated cohort were observed (FIG. 3b). Surprisingly as illustrated in FIG. 3a, HMGCR positive and ER negative patients have a better outcome than HMGCR negative and ER positive patients in the treated cohort.

Thus, a favorable effect of HMGCR expression on tamoxifen response has been demonstrated. Further, a group of ER negative patients who may respond to tamoxifen is identified. Consequently, HMGCR protein is an endocrine treatment marker which may be an alternative or complement to ER.

Figure 4B:
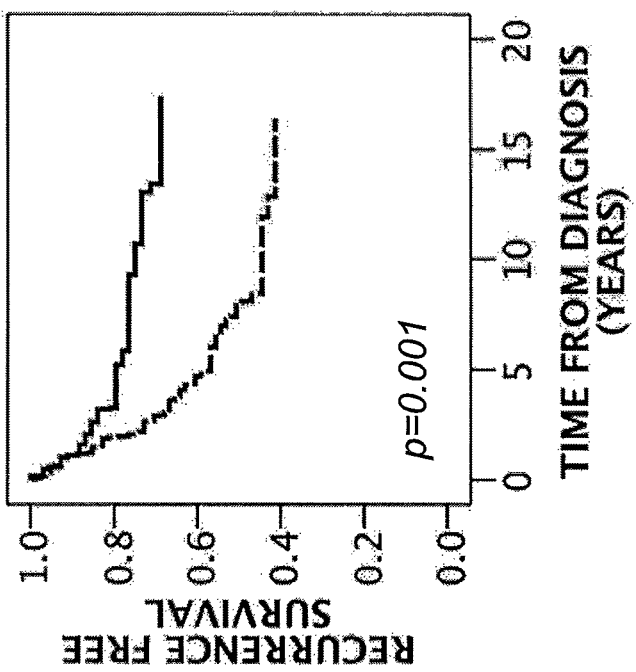
Figure 4A:
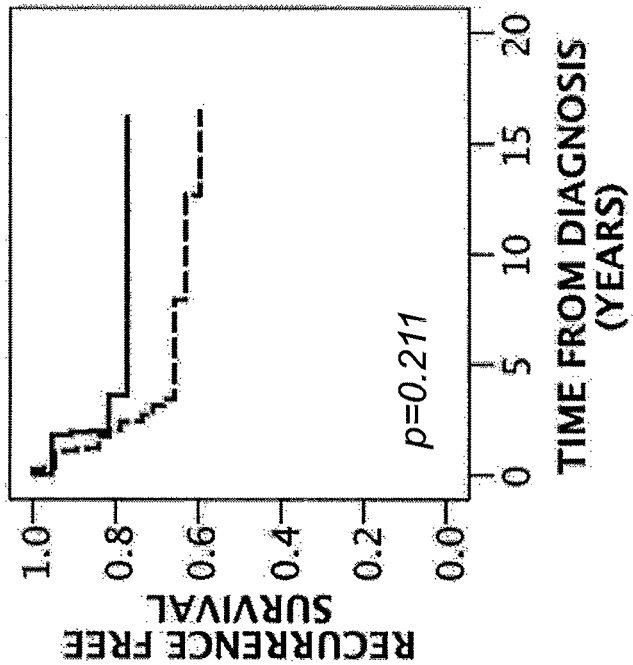
Figure 5B:
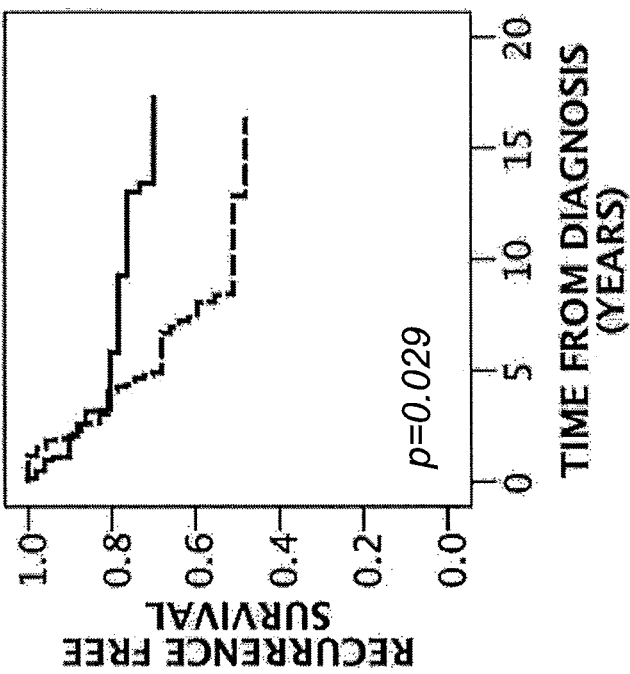
Figure 5A:
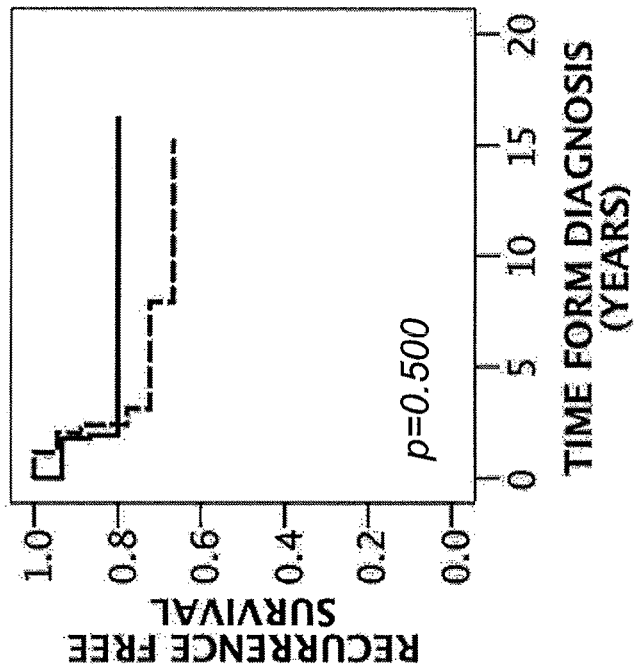
Figures 6A, 6B:
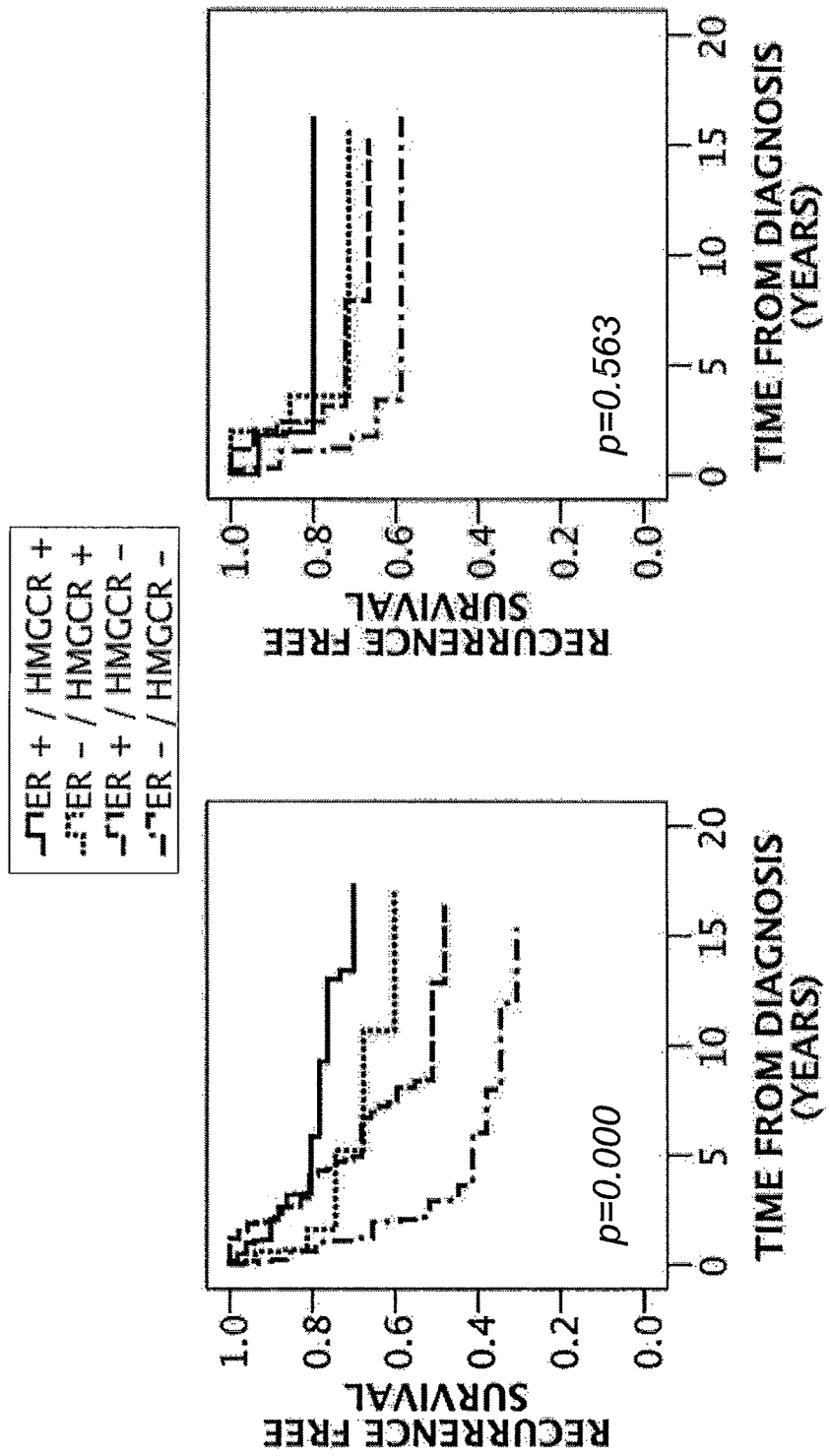
FIGS. 6A and 6B show the impact on survival if splitting subjects into groups with different combinations of HMGCR protein expression status and ER status. Briefly, all subjects were split into four groups based on HMGCR status and ER status, i.e. subjects that are HMGCR positive and ER positive, subjects that are HMGCR positive and ER negative, subjects that are HMGCR negative and ER positive or subjects that are HMGCR negative and ER negative. ER positive=fraction score of >10% and ER negative=fraction score of >10%.

Next, the relationship between HMGCR expression and RFS in lymph node positive patients treated with tamoxifen was investigated. This revealed that HMGCR expression was associated with an improved RFS (p=0.001) in lymph node positive patients who received tamoxifen (FIG. 4a). Similar results were obtained when analyzing the ER positive subjects of the same subgroup (FIG. 5a). A trend of better survival for the HMGCR positive subjects of the node negative subgroups was also observed (FIGS. 4b and 5b), but these subgroups contained too few patients to yield statistically significant results. The impact on RFS based on node status in strata with different combinations of HMGCR expression and ER status in tamoxifen treated subjects was analyzed. In node positive, tamoxifen treated subjects, HMGCR/ER status had a highly significant impact on RFS (p=0.000) (FIG. 6a), compared to lymph node negative tamoxifen treated patients (FIG. 6b). Regarding the node positive subjects, HMGCR positive and ER negative patients had a better outcome than HMGCR negative and ER positive patients in the treated cohort (FIG. 6a).

Figure 7B:
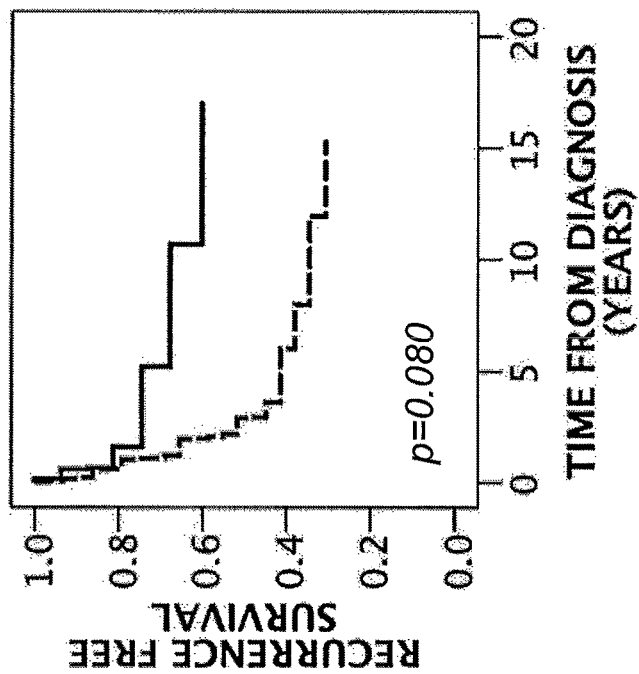
Figure 7A:
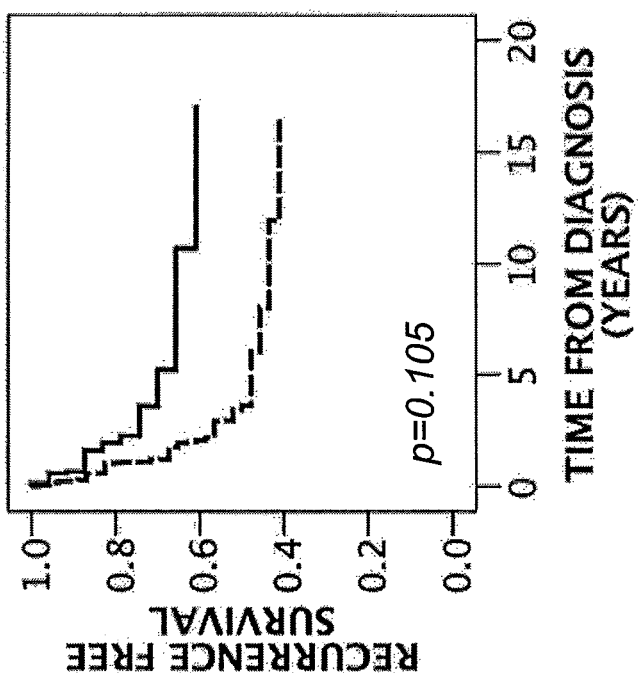

The impact on survival for tamoxifen treated subjects that are HMGCR positive and ER negative subjects is seen in more detail in FIGS. 7A and 7B. The positive effect on RFS based on the HMGCR level in ER negative subjects is seen in FIG. 7a, and that effect appears to be further enhanced in lymph node positive patients is seen in FIG. 7b.

If the parameters were changed, and the RFS analysis was based on tamoxifen treatment of HMGCR high or low subjects, irrespective of ER status, the results revealed a significantly improved survival upon tamoxifen treatment for patients with HMGCR high tumors (FIG. 8a) in contrast to patients with HMGCR low tumors, where tamoxifen treatment had no impact on survival (FIG. 8b).

An improved survival upon tamoxifen treatment was also observed when analyzing HMGCR positive and ER negative subjects as seen in FIG. 9a. That trend appears to be further enhanced in lymph node positive patients is seen in FIG. 9b. The results of FIGS. 8A-9B further support that HMGCR positive subjects benefit from tamoxifen treatment and that such benefit also exists in HMGCR positive subjects in the subgroup of ER negative patients, which have previously been considered non-responsive to tamoxifen.

When the breast cancer subjects were divided into HMGCR positive or ER positive and HMGCR negative and ER negative, respectively, a significantly positive effect of tamoxifen treatment was observed in the former group, while no positive effect was observed in the latter (10a and 10b, respectively).

In the literature, PR has been proposed as an alternative or complement to ER in endocrine treatment prediction. Accordingly, its relation to HMGCR status has been investigated. PR positive and HMGCR positive subjects showed significant response to tamoxifen treatment, while no response was observed in the group of PR negative and HMGCR negative subjects (11a and 11b, respectively). In the group of HMGCR positive and PR negative subjects a trend of tamoxifen impact on survival may be observed (FIG. 12). Probably due to too few patients in this group the trend is not statistically significant.

5. Gene Expression Analysis of Breast Cancer a) Material and Methods

Data was collected from a previously performed microarray study, Chanrion et al, based on a patient cohort of 155 primary breast tumors obtained from patients who had undergone initial surgery between 1989 and 2001 at the Cancer Research Center of Val d'Aurelle in Montpellier, the Bergonie' Institute in Bordeaux, or the Department of Obstetrics and Gynecology of Turin.

The median follow-up time for all patients was 5.5 years. Eight tumors were ER negative, and six of these tumors were progesterone receptor (PR) positive. No patient received neoadjuvant systemic chemotherapy. All patients were treated with adjuvant tamoxifen (20 mg daily) for 5 years. 121 patients also received adjuvant radiotherapy. Raw gene expression data and clinical data were downloaded from Gene Expression Omnibus (http://www.ncbi.nlm.nih.gov/GEO/) (accession number GSE 9893). The log ratio of gene expression values was used without further transformation. For statistical analysis HMGCR mRNA expression levels were analysed as a continuous variable.

b) Results

The HMGCR mRNA expression could be analyzed in all of the 155 tumor samples. Dichotomized variables were constructed for statistical analysis. As can be seen in FIG. 13a, patients having tumors with high expression levels of HMGCR mRNA had a significantly better RFS than patients with low HMGCR mRNA expression levels. An improved RFS for subjects with high expression levels of HMGCR mRNA was also observed when analyzing ER positive subjects only, as seen in FIG. 13b.

Determination of Whether a Breast Cancer Patient is Likely to Benefit from an Endocrine Treatment and Treatment of Said Patient 6. A Non-Limiting Example A breast cancer patient can present symptoms or signs such as a palpable lump/tumor, secretion from the mammilla or skin deformities. A proportion of breast cancers, generally without symptoms, are also detected by screening mammography. If those tests are not conclusive for diagnosis, a breast biopsy may be performed i.e. removal of a selected physical piece of tissue from the suspected tumor.

Following the diagnosis of breast cancer, the tumor is normally removed by surgery (e.g. by mastectomy or partial mastectomy).

To perform the treatment predictive method, a tumor tissue sample is obtained. The tumor tissue sample may be obtained from a specimen from an earlier surgical removal of the tumor or from a biopsy performed earlier during the diagnosis of the cancer.

For the provision of a reference sample showing a negative HMGCR staining (negative reference), a material is taken from a tissue having no HMGCR expression, e.g. archival material comprising tissue lacking detectable HMGCR protein expression. The negative reference may show an absent cytoplasmic intensity.

For the provision of a reference sample showing a high HMGCR staining (positive reference), a material is taken from a tissue having high HMGCR expression, e.g. breast cancer tissue having a pre-established high HMGCR protein expression. The positive reference may show a strong cytoplasmic intensity.

The materials (the tumor tissue sample and the reference samples) are fixated in buffered formalin and histo-processed in order to obtain thin sections (4 μm). Alternatively, the reference samples may be preprepared, e.g. already fixated in buffered formalin or already mounted on slides (see below).

Immunohistochemistry is performed as described in Examples, section 3. One or more sample sections from each sample are mounted on glass slides that are incubated for 45 min in 60° C., de-paraffinized in xylene (2×15 min) and hydrated in graded alcohols. For antigen retrieval, the slides are immersed in TRS (Target Retrieval Solution, pH 6.0, DakoCytomation) and boiled for 4 min at 125° C. in a Decloaking Chamber® (Biocare Medical). Then, the slides are placed in the Autostainer® (DakoCytomation) and endogenous peroxidase is initially blocked with H2O2 (DakoCytomation). The reason for mounting multiple sample sections may be to increase the accuracy of the results.

A primary HMGCR specific antibody (e.g. the anti-HMGCR antibody of Examples, section 2 or 4) is added to the slides, which are then incubated for 30 min in room temperature, followed incubation for 30 min in room temperature with the labeled secondary antibody (e.g. goat-anti-rabbit peroxidase conjugated Envision®). To detect the secondary antibody, diaminobenzidine (DakoCytomation) is used as chromogen, contrasted with a Harris hematoxylin (Sigma-Aldrich) counterstaining. Between all steps, slides are rinsed in wash buffer (DakoCytomation). The slides are then mounted with Pertex® (Histolab).

As a tool to validate the staining procedure, two control cell-lines may be used; e.g. one slide with cells expressing HMGCR (positive cell line) and one slide with cells without HMGCR expression (negative cell line). The skilled artisan understands how to provide such cell lines, for example guided by the disclosure of Rhodes et al. (2006) The biomedical scientist, p 515-520. The control-line slides may be simultaneously stained in the same procedure as the breast cancer slides, i.e. incubated with the same primary and secondary antibodies.

To obtain digital images, the breast cancer tumor slides, the reference slides, and optionally, the slides with control cell-lines, may be scanned in a light microscope using a ScanScope T2 automated slide scanning system (Aperio Technologies) at ×20 magnification. However, this scanning step is not necessary, but may make the procedure easier if, for example, the preparation and staining of the slides and the evaluation of the cytoplasmic intensity (see below) are performed at different locations or by different persons.

If control cell-lines are used, these are inspected to validate the staining procedure. If the cell-lines display staining results outside acceptable criteria, e.g. staining artifacts recognized by the skilled artisan, the staining of the slides is considered as invalid and the whole staining procedure is repeated with new slides. If the positive and negative cell-lines display strong staining intensity and no staining intensity, respectively, the staining is considered as valid.

The stained sample slide(s) from the tumor sample is/are evaluated manually by visual inspection, and the cytoplasmic intensity (CI) of the breast cancer slide(s) is/are graded as described in Examples, Section 3. In the grading, the cytoplasmic intensity (CI) is subjectively classified as: absent=no immunoreactivity, weak=faint immunoreactivity, moderate=medium immunoreactivity or strong=distinct and strong immunoreactivity. The person performing the evaluation and grading is aided by visual inspection of the stained positive and negative reference slides.

The reference value may be an absent CI, and in such case it is concluded that the patient in question is likely to benefit from an endocrine treatment if the sample value derived from the subject is higher than an absent CI, i.e. if the sample value is a weak, moderate or strong CI.

The above conclusion may lead a physician to apply an endocrine treatment. However, in some cases, such decision may depend on several parameters. Anyhow, the fact that the patient is HMGCR positive is in favor of a decision to treat the patient with an endocrine treatment, especially a tamoxifen treatment.

All cited material, including but not limited to publications, DNA or protein data entries, and patents, referred to in this application are herein incorporated by reference.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. Method of treatment of a mammalian subject in need thereof, wherein said subject has a breast cancer, comprising the steps of:
   a) providing a sample earlier obtained from said subject;
   b) evaluating the amount of 3-hydroxy-3-methylglutaryl-coenzyme A reductase (HMGCR) protein or HMGCR mRNA present in at least part of said sample, and determining a sample value corresponding to said amount;
   c) comparing the sample value obtained in step b) with a reference value; and, if said sample value is higher than said reference value,
   d) treating said subject with an endocrine treatment regimen,
   wherein said endocrine treatment is a selective estrogen receptor modulator (SERM) treatment.

2. Method according to claim 1, wherein said breast cancer is estrogen receptor (ER) negative or progesterone receptor (PR) negative.

3. Method of treatment of a mammalian subject in need thereof, wherein said subject has a breast cancer, comprising the steps of:
   a) providing a sample from said subject;
   b) evaluating the amount of 3-hydroxy-3-methylglutaryl-coenzyme A reductase (HMGCR) protein or HMGCR mRNA present in at least part of said sample, and determining a sample value corresponding to said amount;
   c) comparing the sample value obtained in step b) with a reference value and thereby determining the HMGCR status of said subject;
   d) obtaining the estrogen receptor (ER) status for said subject; and if said ER status or said HMGCR status is positive,
   e1) treating said subject with an endocrine treatment regimen, or if said ER status and said HMGCR status are negative,
   e2) treating said subject with a non-endocrine treatment regimen,
   wherein said endocrine treatment is a selective estrogen receptor modulator (SERM) treatment.

4. Method according to claim 3, wherein the ER status is obtained from the sample of step a).

5. Method according to claim 1, wherein said SERM treatment is selected from the group consisting of toremifene, raloxifene, droloxifene, arzoxifene and tamoxifen.

6. Method according to claim 1, wherein said sample comprises tumor cells from said subject.

7. Method according to claim 1, wherein said sample is a tissue sample.

8. Method according to claim 7, wherein said tissue sample is a breast cancer tissue sample.

9. Method according to claim 1, wherein said subject is a human female.

10. Method according to claim 1, wherein said subject is a premenopausal female.

11. Method according to claim 1, wherein said breast cancer is a stage II breast cancer.

12. Method according to claim 1, wherein said breast cancer is a node positive breast cancer.

13. Method of treatment of a mammalian subject in need thereof according to claim 1, wherein the evaluation of step b) is limited to the cytoplasms of cells of said sample.

14. Method of treatment of a mammalian subject in need thereof according to claim 1, wherein step b) comprises:
   b1) applying to said sample a quantifiable affinity ligand capable of selective interaction with the HMGCR protein to be evaluated, said application being performed under conditions that enable binding of said affinity ligand to any HMGCR protein present in said sample;
   b2) removing non-bound affinity ligand; and
   b3) quantifying the affinity ligand remaining in association with said sample to evaluate said amount.

15. Method of treatment of a mammalian subject in need thereof according to claim 3, wherein the evaluation of step b) is limited to the cytoplasm in cells of said sample.

16. Method of treatment of a mammalian subject in need thereof according to claim 3, wherein step b) comprises:
   b1) applying to said sample a quantifiable affinity ligand capable of selective interaction with the HMGCR protein to be evaluated, said application being performed under conditions that enable binding of said affinity ligand to any HMGCR protein present in said sample;
   b2) removing non-bound affinity ligand; and
   b3) quantifying the affinity ligand remaining in association with said sample to evaluate said amount.

* * * * *